US010767207B2

United States Patent
Ge et al.

(10) Patent No.: US 10,767,207 B2
(45) Date of Patent: *Sep. 8, 2020

(54) TRICHODERMA REESEI HOST CELLS EXPRESSING A GLUCOAMYLASE FROM ASPERGILLUS FUMIGATUS AND METHODS OF USE THEREOF

(71) Applicant: DANISCO US INC, Palo Alto, CA (US)

(72) Inventors: Jing Ge, Palo Alto, CA (US); Ling Hua, Hockessin, DE (US); Sung Ho Lee, Palo Alto, CA (US); Jalsen Li, Palo Alto, CA (US); Jayarama K Shetty, Palo Alto, CA (US); Zhongmei Tang, Shanghai (CN); Bo Zhang, Shanghai (CN); Kun Zhong, Shanghai (CN)

(73) Assignee: Danisco US INC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/281,989

(22) Filed: Feb. 21, 2019

(65) Prior Publication Data

US 2019/0177757 A1 Jun. 13, 2019

Related U.S. Application Data

(63) Continuation of application No. 14/649,167, filed as application No. PCT/US2013/071154 on Nov. 21, 2013, now abandoned.

(30) Foreign Application Priority Data

Dec. 11, 2012 (WO) ................ PCT/CN2012/086349

(51) Int. Cl.
| *C12P 19/14* | (2006.01) |
| *C12P 19/02* | (2006.01) |
| *C12N 9/30* | (2006.01) |
| *C12C 5/00* | (2006.01) |
| *C11D 3/386* | (2006.01) |
| *A21D 8/04* | (2006.01) |
| *C12N 9/34* | (2006.01) |

(52) U.S. Cl.
CPC ............ *C12P 19/14* (2013.01); *C12N 9/2428* (2013.01); *C12P 19/02* (2013.01); *C12Y 302/01003* (2013.01); *Y02E 50/17* (2013.01)

(58) Field of Classification Search
CPC .. C12P 19/14; C12P 19/02; C12P 7/06; C12N 9/242; C12N 9/246; C12C 5/004; C11D 3/386; D06L 1/06
See application file for complete search history.

(56) References Cited

U.S. PATENT DOCUMENTS

| 5,665,585 | A | 9/1997 | Torkeli |
| 9,428,780 | B2 | 8/2016 | Baldwin |
| 2003/0082595 | A1* | 5/2003 | Jiang .................... C12N 9/0006 435/6.13 |
| 2015/0218606 | A1* | 8/2015 | van Brussel-Zwijnen ................. C12P 19/16 435/96 |

FOREIGN PATENT DOCUMENTS

| WO | 2003012071 A2 | 2/2003 |
| WO | 2005/001036 A2 | 1/2005 |
| WO | 2005/052148 A2 | 6/2005 |

OTHER PUBLICATIONS

Database UniProt [Online], Jul. 5, 2005 (Jul. 5, 2005), Glucan 1,4-alpha-glucosidase, retrieved from EBI accession No. Uniprot: Q4WIT7.
T.N. Nwagu Asian Journal of Biotechnology, Jul. 8, 2010, vol. 3, No. 1, pp. 46-57.
International Search Report dated Nov. 21, 2013.

* cited by examiner

*Primary Examiner* — Maryam Monshipouri

(57) ABSTRACT

Fungal glucoamylases from *Aspergillus fumigatus*—expressed in *Trichoderma reesei* host cells (AfGATR) are provided. *Trichoderma reesei* host cells express AfGATRs at higher, or at least comparable, levels to natively expressed AfGA *Aspergillus fumigatus*. AfGATRs, including AfGA1TR and AfGA2TR, exhibit high activity at elevated temperatures and at low pH, so AfGATRs can be used efficiently in a process of saccharification in the presence of alpha-amylase, such as *Aspergillus kawachii* alpha-amylase (AkAA). AfGATRs advantageously catalyze starch saccharification to an oligosaccharide composition significantly enriched in DP1 (i.e., glucose) compared to the products of saccharification catalyzed by *Aspergillus niger* glucoamylase (AnGA) or native AfGA expressed in *Aspergillus fumigatus*. AfGATRs such as AfGA1TR, AfGA2TR or a variant thereof can be used at a lower dosage than AnGA and natively expressed AfGAs to produce comparable levels of glucose.

29 Claims, 10 Drawing Sheets

Specification includes a Sequence Listing.

FIG. 1A

```
SEQ ID NO 1    ATGSLDSWLGTETTVALNGILANIGADGAYAKSAKPGIIIASPSTSEPDYYYTWTRDAAL  60
SEQ ID NO 2    ATGSLDSWLGTETTVALNGILANIGADGAYAKSAKPGIIIASPSTSEPDYYYTWTRDAAL  60
SEQ ID NO 3    ATGSLDSWLATESTVSLNGILANIGADGAYAKSAKPGIIIASPSTSDPDYYYTWTRDAAL  60
SEQ ID NO 4    ASTSLDAWLATETTVSLSGILANIGADGAYSKSAKPGVVIASPSTDNPNYYYTWTRDSAL  60
SEQ ID NO 5    ATVGLDAWLASETTFSLNGILANIGSSGAYSASAKPGVVIASPSTNNPNYYYTWTRDSAL  60
SEQ ID NO 6    ATASLNTWLSTEASFALDGILTNIGANGAYAKTAKAG----------ADYYTWTRDAAL  49
                 *   *  **  *     *  *** ***   ***  **  *              ******  **

SEQ ID NO 1    VTKVLVDLFRNGNLGLQKVITEYVNSQAYLQTVSNPSGGLASG-GLAEPKYNVDMTAFTG 119
SEQ ID NO 2    VTKVLVDLFRNGNLGLQKVITEYVNSQAYLQTVSNPSGGLASG-GLAEPKYNVDMTAFTG 119
SEQ ID NO 3    VTKVLVDLFRNGNLGLQKVITEYVNSQAYLQTVSTPSGGLSSG-GLAEPKYNVDMTAFTG 119
SEQ ID NO 4    TLKVLIDLFRNGNLGLQTVIEEYVNAQAYLQTVSNPSGDLSSGAGLAEPKFNVDMSAFTG 120
SEQ ID NO 5    TLKVLIDLFGNGNLSLQTVIEEYINAQAYLQTVSNPSGDLSSGAGLAEPKYNVDMSPFTG 120
SEQ ID NO 6    TVKVLVDLFHNGDLSLQTILEEYTNSQAYLQTVSNPSGGLASG-GLAEPKFYVDMTAFTG 108
                ***  *** ** *  **       ** * ********  ***  *  **  ******   ***    ***

SEQ ID NO 1    AWGRPQRDGPALRATALIDFGNWLIDNGYSSYAVNNIWPIVRNDLSYVSQYWSQSGFDLW 179
SEQ ID NO 2    AWGRPQRDGPALRATALIDFGNWLIDNGYSSYAVNNIWPIVRNDLSYVSQYWSQSGFDLW 179
SEQ ID NO 3    AWGRPQRDGPALRATALIDFGNWLIDNGYSSYAVNNIWPIVRNDLSYVSQYWSQSGFDLW 179
SEQ ID NO 4    SWGRPQRDGPALRAIALIDFGNWLIENGYTSLAANNIWPIVRNDLSYVAQYWSQSGFDLW 180
SEQ ID NO 5    GWGRPQRDGPALRAIALIEFGNWLIDNGYSSYAVNNIWPIVRNDLSYVSQYWSQSGFDLW 180
SEQ ID NO 6    SWGRPQRDGPALRATTLIGFGNWLIDNGYSSYASNNIWPIVRNDLTYVAQYWSKSGYDLW 168
                *************   ** ****** ***  *  *  *********** **  **** **  ***

SEQ ID NO 1    EEVNSMSFFTVAVQHRALVEGSTFAKRVGASCSWCDSQAPQILCYMQSFWTGSYINANTG 239
SEQ ID NO 2    EEVNSMSFFTVAVQHRALVEGSTFAKRVGASCSWCDSQAPQILCYMQSFWTGSYINANTG 239
SEQ ID NO 3    EEVNSMSFFTVAVQHRALVEGSTFAKRVGASCSWCDSQAPQILCYMQSFWTGSYINANTG 239
SEQ ID NO 4    EEVNSMSFFTVANQHRSLVEGSTFAAKVGASCSWCDSQAPQILCYMQTFWTGSYMNANTG 240
SEQ ID NO 5    EEVNSMSFFTVANQHRALVQGSTFAARVGASCSWCDSQAPQILCYMQTFWTGSYINANTG 240
SEQ ID NO 6    EEVNSMSFFTVAVQHRALVEGSTFAHRVGASCPWCDSQAPQILCYMQNFWTGSYINANTG 228
                ************  ***  **   *****   *****  **************  ****** ****

SEQ ID NO 1    GGRSGKDANTVLASIHTFDPEAGCDDTTFQPCSPRALANHKVYTDSFRSVYAINSGIPQG 299
SEQ ID NO 2    GGRSGKDANTVLASIHTFDPEAGCDDTTFQPCSPRALANHKVYTDSFRSVYAINSGIPQG 299
SEQ ID NO 3    GGRSGKDANTVLASIHTFDPEAGCDDTTFQPCSPRALANHKVYTDSFRSVYAINSGIPQG 299
SEQ ID NO 4    GGRSGKDANTVLTSIATFDPEATCDDVTFQPCSPRALANHKVYTDSFRSVYGLNSGIAEG 300
SEQ ID NO 5    GGRSGKDSNTVLTTIHTFDPEATCDDVTFQPCSPRALANHKVYTDSFRSIYGVNSGIAQG 300
SEQ ID NO 6    GGRSGKDANTVLASIHTFDPDAACDDTTFQPCSSRALANHKVYTDSFRSVYSLNTGIAQG 288
                ******  ****     *  ****  *  *********** *  **  **   ***   *

SEQ ID NO 1    AAVSAGRYPEDVYYNGNPWFLTTLAAAEQLYDAIYQWKKIGSISITSTSLAFFKDIYSSA 359
SEQ ID NO 2    AAVSAGRYPEDVYYNGNPWFLTTLAAAEQLYDAIYQWKKIGSISITSTSLAFFKDIYSSA 359
```

FIG 1B

```
SEQ ID NO 3    VAVSAGRYPEDVYYNGNPWFLTTLAAAEQLYDAIYQWKKIGSISITSTSLAFFKDIYSSV 359
SEQ ID NO 4    VAVAVGRYPEDSYYNGNPWFLSNLAAAEQLYDAIYQWNKIGSITITSTSLAFFKDVYSSA 360
SEQ ID NO 5    VAVSVGRYPEDSYYGGNPWFLSNLAAAEQLYDAIYQWNKIGSITITSTSLAFFKDVYSSA 360
SEQ ID NO 6    VAVAAGRYPEDSYYNGNPWFLTTLAAAEQLYDAIYQWQKARSISITSTSLAFFKDIYSSA 348
               **  ****** ** ****** ************** *  ** ********** ***

SEQ ID NO 1    AVGTYASSTSTFTDIINAVKTYADGYVSIVQAHAMNNGSLSEQFDKSSGLSLSARDLTWS 419
SEQ ID NO 2    AVGTYASSTSTFTDIINAVKTYADGYVSIVQAHAMNNGSLSEQFDKSSGLSLSARDLTWS 419
SEQ ID NO 3    AVGTYASSSSTFTAIIDAVKTYADGYVSIVEAHAMTNGSLSEQFDKSSGMSLSARDLTWS 419
SEQ ID NO 4    AVGTYASGSSAFTSIINAVKTYADGYISVVQSHAMNNGSLSEQFDKNTGAELSARDLTWS 420
SEQ ID NO 5    AVGTYASGSTAFTSIISAVKTYADGYVSIVQGHAAANGSLSEQFDRNSGVEISARDLTWS 420
SEQ ID NO 6    AVGTYASGSSAFTAIIDAVKTYADGYVSIVKAHAMANGSLSEQFDKTYGTCVSARDLTWS 408
               *******    ** ** ********* * *   ** ********    *  *******

SEQ ID NO 1    YAAFLTANMRRNGVVPAPWGAASANSVPSSCSMGSATGTYSTATATSWPSTLTSGSPGST 479
SEQ ID NO 2    YAAFLTANMRRNGVVPAPWGAASANSVPSSCSMGSATGTYSTATATSWPSTLTSGSPGST 479
SEQ ID NO 3    YAALLTANMRRNGVVPAPWGAASANSVPSSCSMGSATGTYSTATATSWPSTLTSGSP-SD 478
SEQ ID NO 4    YAALLTANMRRNGVVPPSWGAASATSIPSSCTTGSAIGTYSTPTATSWPSTLTSGTGSPG 480
SEQ ID NO 5    YAALLTANLRRNGVMPPSWGAASANSVPSSCSMGSATGTYSTPTATAWPSTLTSATGIP- 479
SEQ ID NO 6    YAALLTASMRRNGVVPPSWDAASANTLPSSCSTGSATGTYSTATVTTWPSTLTSGSASAT 468
               *** ***  ***** * * ****    **** *** ***** * * *******

SEQ ID NO 1    TTVGT------TTSTTSGTAAETACATPTAVAVTFNEIATTTYGENVYIVGSISELGNWD 533
SEQ ID NO 2    TTVGT------TTSTTSGTATETACATPTAVAVTFNEIATTTYGENVYIVGSISELGNWD 533
SEQ ID NO 3    TTSGT------TPGTTT---TTSACTTPTSVAVTFDEIATTTYGENVYIIGSISQLGSWD 529
SEQ ID NO 4    STTSATGSVS--TSVSATTTSAGSCTTPTSVAVTFDEIATTSYGENVYIVGSISQLGSWN 538
SEQ ID NO 5    VTTSATASVTKATSATSTTTSATTCTTPTSVAVTFDEIATTTYGENVFIVGSISQLGSWD 539
SEQ ID NO 6    TTIMATST---ATSSSTTTSTTTACTTPSTVAVTFNVIATTTYGENVYIVGSISQLGNWD 525
                  *                   *  ** ***** **** ***** * **** ** *

SEQ ID NO 1    TSKAVALSASKYTSSNNLWYVSVTLPAGTTFEYKYIRKESDGSIVWESDPNRSYTVPAAC 593
SEQ ID NO 2    TSKAVALSASKYTSSNNLWYVSVTLPAGTTFEYKYIRKESDGSIVWESDPNRSYTVPAAC 593
SEQ ID NO 3    TSKAVPLSSSKYTSSNNLWYVTINLPAGTTFEYKYIRKESDGSIEWESDPNRSYTVPSAC 589
SEQ ID NO 4    TANAIALSASKYTTSNNLWYVTINLPAGTTFQYKYIRKESDGTVKWESDPNRSYTVPSAC 598
SEQ ID NO 5    TSKAIALSASQYTSSNHLWFATLSLPAGTTFQYKYIRKESNGSIVWESDPNRSYTVPSGC 599
SEQ ID NO 6    TGSAVALSASKNTSSNNLWYVDINLPGGTAFEYKYIRKETDGSIVWESDPNRSYTVPSSC 585
               *  *  ** *  ** * ** **         ** ** * *******  * *********  *

SEQ ID NO 1    GVSTATENDTWQ---------- 605
SEQ ID NO 2    GVSTATENDTWR---------- 605
SEQ ID NO 3    GVSTATEKDTWR---------- 601
SEQ ID NO 4    GVSTATENDTWR---------- 610
SEQ ID NO 5    GVSTATENDTWR---------- 611
SEQ ID NO 6    GVSTATESDTWRCTLETQSVRN 607
```

TRICHODERMA REESEI HOST CELLS EXPRESSING A GLUCOAMYLASE FROM ASPERGILLUS FUMIGATUS AND METHODS OF USE THEREOF

CROSS REFERENCE TO RELATED APPLICATIONS

The present application is a continuation of U.S. patent application Ser. No. 14/649,167, filed Jun. 2, 2015, which is a 35 U.S.C. § 371 national phase filing of International Patent Application No. PCT/US13/71154, filed Nov. 21, 2013, which claims benefit of priority from International Patent Application No. PCT/CN2012/086349 filed on Dec. 11, 2012, the disclosures of each of which are incorporated herein by reference.

INCORPORATION BY REFERENCE

The content of the following submission on ASCII text file is incorporated herein by reference in its entirety: a computer readable form (CRF) of the Sequence Listing (file name: 40165USPCT_SEQ_LIST.txt, date recorded: Feb. 21, 2019, size: 53,248 bytes).

FIELD OF THE INVENTION

*Trichoderma reesei* host cells expressing a glucoamylase from *Aspergillus fumigatus*, (AfGATR) or a variant thereof, and methods of use thereof.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with glucoamylase (also called amyloglucosidase or GA). The resulting syrup has a high glucose content. Much of the glucose syrup that is commercially produced is subsequently enzymatically isomerized to a dextrose/fructose mixture known as isosyrup. The resulting syrup also may be fermented with microorganisms, such as yeast, to produce commercial products including ethanol, citric acid, lactic acid, succinic acid, itaconic acid, monosodium glutamate, gluconates, lysine, other organic acids, other amino acids, and other biochemicals, for example. Fermentation and saccharification can be conducted simultaneously (i.e., an SSF process) to achieve greater economy and efficiency.

Glucoamylases (glucan 1,4-α-glucohydrolases, EC 3.2.1.3) are starch hydrolyzing exo-acting carbohydrases, which catalyze the removal of successive glucose units from the non-reducing ends of starch or related oligo and polysaccharide molecules. Glucoamylases can hydrolyze both the linear and branched glucosidic linkages of starch (e.g., amylose and amylopectin). α-Amylases, on the other hand, hydrolyze starch, glycogen, and related polysaccharides by cleaving internal α-1,4-glucosidic bonds at random. Glucoamylases have been used for a variety of different purposes, including starch saccharification, brewing, baking, production of syrups for the food industry, production of feedstocks for fermentation processes, and in animal feed to increase digestability.

Glucoamylases are produced by numerous strains of bacteria, fungi, and plants. For example, a glucoamylase is produced by strains of *Aspergillus fumigatus*. Luo et al. (2008) "Production of acid proof raw starch-digesting glucoamylase from a newly isolated strain of *Aspergillus fumigatus* MS-09," *Sci. Tech. Food Indus.* 29(5): 151-154; Sellars et al. (1976) "Degradation of barley by *Aspergillus fumigatus* Fres," *Proc. Int. Biodegradation Symp.*, 3rd, S. J. Miles et al., eds., *Appl. Sci., Barking, UK*, pp. 635-43; Domingues et al. (1993) "Production of amylase by soil fungi and partial biochemical characterization of amylase of a selected strain (*Aspergillus fumigatus* Fresenius)," *Can. J. Microbiol.* 39(7): 681-85; Cherry et al. (2004) "Extracellular glucoamylase from the isolate *Aspergillus fumigatus*," *Pakistan J. Biol. Sci.* 7(11): 1988-92. However, *Aspergillus fumigatus* is highly allergenic and pathogenic to humans and plants. Thus, *Aspergillus fumigatus* is not a viable production host for glucoamylases used in industrial processes for manufacturing products for human consumption. There is a need to produce *A. fumigatus* glucoamylases from a suitable host.

SUMMARY

Glucoamylases from *Aspergillus fumigatus* that are expressed in *Trichoderma reesei* (AfGATRs) catalyze saccharification for extended periods at high temperatures and an acidic pH. Examples of known glucoamylases from *Aspergillus fumigatus* (SEQ ID NO: 1 and 2), encoding nucleic acids, and *Trichoderma reesei* host cells that express the polynucleotides are provided. *Trichoderma reesei* host cells express AfGATRs at higher, or at least comparable, levels to natively expressed AfGA *Aspergillus fumigatus*. AfGATRs, including AfGA1TR and AfGA2TR, exhibit high activity at elevated temperatures and at low pH, so AfGATRs can be used efficiently in a process of saccharification in the presence of α-amylase, such as *Aspergillus kawachii* α-amylase (AkAA). AfGATRs advantageously catalyze starch saccharification to an oligosaccharide composition significantly enriched in DP1 (i.e., glucose) compared to the products of saccharification catalyzed by *Aspergillus niger* glucoamylase (AnGA) or native AfGA expressed in *Aspergillus fumigatus*. AfGATRs such as AfGA1TR, AfGA2TR or a variant thereof can be used at a lower dosage than AnGA and natively expressed AfGAs to produce comparable levels of glucose. AfGATRs or variants thereof can be used in combination with enzymes derived from plants (e.g., cereals and grains). AfGATRs or variants thereof also can be used in combination with enzymes secreted by, or endogenous to, a host cell. For example, an AfGATR or a variant thereof can be added to a saccharification reaction, or SSF process during which one or more amylases, additional glucoamylases, proteases, lipases, phytases, esterases, redox enzymes, transferases, or other enzymes are secreted by the production host. An AfGATR or a variant thereof may also work in combination with endogenous non-secreted production host enzymes. In another example, an AfGATR or a variant thereof can be secreted by a production host cell with other enzymes during saccharification or SSF. The AfGATR glucoamylase, or a variant thereof, may be used in a process involving direct hydrolysis of starch for syrup and/or biochemicals (e.g., alcohols, organic acids, amino acids, other biochemicals and biomaterials) where the reaction temperature is below the gelatinization temperature of substrate. An AfGATR or a variant thereof can be secreted by a *Trichoderma reesei* host cell with other enzymes during saccharification or SSF.

Accordingly, provided is a recombinant *Trichoderma reesei* host cell expressing an AfGATR or variant thereof having at least 80% sequence identity to SEQ ID NO: 12 or 13, wherein said *Trichoderma reesei* host cell expresses the AfGATR or variant at a comparable level to a *Aspergillus fumigatus* host cell, which expresses an AfGA or variant thereof having the same amino acid sequence of the AfGATR or variant thereof, under identical conditions.

Also provided is a recombinant *Trichoderma reesei* host cell expressing an AfGATR or variant thereof having at least 80% sequence identity to SEQ ID NO: 12 or 13, wherein the AfGATR or variant thereof is more thermostable than an AfGA or variant thereof having the same amino acid sequence of AfGATR or variant thereof, and wherein the AfGA or variant thereof is expressed in an *A. fumigatus* host cell.

Also provided is a method for producing a recombinant AfGATR or variant thereof, comprising: (a) providing a *T. reesei* host cell that expresses a recombinant AfGATR or variant thereof having at least 80% sequence identity to SEQ ID NO: 12 or 13; (b) culturing said host cell under conditions which permit the production of said recombinant AfGATR or variant thereof; and (c) isolating said recombinant AfGATR, or variant thereof, wherein the AfGATR or variant thereof is more thermostable than an AfGA or variant thereof having the same amino acid sequence of AfGATR or variant thereof, and wherein the AfGA or variant thereof is expressed in an *A. fumigatus* host cell.

Also provided is a recombinant AfGATR, or variant thereof, produced by the disclosed host cells. The recombinant AfGATR or variant thereof may have at least 70% activity at 74° C. at pH 5.0 over 10 min. The recombinant AfGATR or variant thereof may be AfGA1TR. The AfGA1TR may have at least 70% activity over a temperature range of 55°–74° C. at pH 5.0 over 10 min. The AfGA1TR may have an optimum temperature of about 68° C. The recombinant AfGATR or variant thereof may also be AfGA2TR. The AfGA2TR may have at least 70% activity over a temperature range of 61° to 74° C. at pH 5.0 over 10 min. The AfGA2TR may have an optimum temperature of about 69° C. The recombinant AfGATR or variant thereof may comprise an amino acid sequence with at least 90%, 95%, or 99% amino acid sequence identity to sequence identity to SEQ ID NO: 12. The recombinant AfGATR or variant thereof may comprise SEQ ID NO: 12. The recombinant AfGATR or variant thereof may also consist of an amino acid sequence with at least 90%, 95%, or 99% amino acid sequence identity to SEQ ID NO: 13. The recombinant AfGATR or variant thereof may consist of SEQ ID NO: 12. The recombinant AfGATR or variant thereof may also comprise an amino acid sequence with at least 90%, 95%, or 99% amino acid sequence identity to sequence identity to SEQ ID NO: 13. The recombinant AfGATR or variant thereof may comprise SEQ ID NO: 13. The recombinant AfGATR or variant thereof may also consist of an amino acid sequence with at least 90%, 95%, or 99% amino acid sequence identity to SEQ ID NO: 13. The recombinant AfGATR or variant thereof may consist of SEQ ID NO: 13.

Also provided is a method of saccharifying a composition comprising starch to produce a composition comprising glucose, wherein said method comprises: (i) contacting a starch composition with the isolated AfGATR or variant thereof of any of claims 4-15; and (ii) saccharifying the starch composition to produce said glucose composition; wherein said AfGA1TR or variant thereof catalyzes the saccharification of the composition comprising starch to a composition comprising glucose. The composition comprising glucose may be enriched in DP1 compared to a second composition comprising DP1 produced by AnGA under the same conditions. The composition comprising glucose may also be enriched in DP1 compared to a second composition comprising DP1 produced by a wild-type AfGA under the same conditions. The AfGATR or variant thereof may be an AfGATR2, and the composition comprising glucose may be enriched in DP1 compared to a second composition comprising DP1 produced by AfGA1TR under the same conditions. The AfGA1TR or variant thereof may be dosed at about 40%-50% the dose of AnGA, to produce the same DP1 yield under the same conditions.

It is also provided that the composition comprising starch comprises liquefied starch, gelatinized starch, or granular starch. Saccharification may be conducted at a temperature range of about 30° C. to about 65° C. The temperature range may be 47° C.-60° C. Saccharification may be conducted over a pH range of pH 2.0-pH 6.0. The pH range may be pH 3.5-pH 5.5. The pH range may also be pH 4.0-pH 5.0.

It is also provided that the method of saccharification may further comprise contacting a starch composition with an alpha-amylase. The alpha-amylase may be AkAA. The method of saccharification may further comprise contacting a starch composition with a pullulinase.

It is also provided that the method of saccharification may further comprise fermenting the glucose composition to produce an End of Fermentation (EOF) product. The fermentation may also be a simultaneous saccharification and fermentation (SSF) reaction. The fermentation may be conducted for 24-70 hours at pH 2-8 and in a temperature range of 25° C.-70° C. The EOF product may comprise ethanol. The EOF product may comprise 8%-18% (v/v) ethanol. The method may further comprise contacting a mash and/or a wort with a pullulanase, an alpha-amylase and the AfGA1TR or variant thereof. The method may also comprise (a) preparing a mash; (b) filtering the mash to obtain a wort; and (c) fermenting the wort to obtain a fermented beverage, wherein the pullulanase, the alpha-amylase and the AfGA1TR or variant thereof are added to: (i) the mash of step (a) and/or (ii) the wort of step (b) and/or (iii) the fermented wort of step (c). The EOF product may comprise a metabolite. The metabolite may be citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, an amino acid, lysine, itaconic acid, 1,3-propanediol, or isoprene.

It is also provided that the method of saccharification may further comprise adding an additional glucoamylase, hexokinase, xylanase, glucose isomerase, xylose isomerase, phosphatase, phytase, protease, pullulanase, β-amylase, an additional α-amylase, protease, cellulase, hemicellulase, lipase, cutinase, trehalase, isoamylase, redox enzyme, esterase, transferase, pectinase, alpha-glucosidase, beta-glucosidase, lyase, hydrolase, or a combination thereof, to said starch composition. The AfGATR, or variant thereof, may be added at a dosage of 0.1 to 2 glucoamylase units (GAU)/g ds. The AfGATR, or variant thereof, may be added at a dosage of about 49.5 μg prot/g solid. The pullulanase may also be added. The isolated AfGATR or a variant thereof may be secreted by said *Trichoderma reesei* host cell. The host cell may further express and secrete an alpha-amylase. The host cell may further express and secrete a pullulanase.

It is also provided that the method of saccharification may further contacting said composition comprising starch with said host cell. The host cell is capable of fermenting the glucose composition.

Also contemplated is a composition comprising glucose produced by the disclosed methods of saccharification. Also contemplated is a liquefied starch produced by the disclosed methods of saccharification. Also contemplated is a fermented beverage produced by the disclosed methods of saccharification.

Also contemplated is the use of saccharifying a composition comprising starch, comprising an isolated AfGA1TR or variant thereof. The composition may be a cultured cell material. The composition may further comprise a glucoamylase. The AfGA1TR or variant thereof may be purified. The AfGA1TR or variant thereof may be secreted by the host cell.

Also contemplated is the use of an AfGA1TR or variant thereof in the production of a composition comprising glucose. Also contemplated is the use of an AfGA1TR or variant thereof in the production of a liquefied starch. Also contemplated is the use of an AfGA1TR or variant thereof in the production of a fermented beverage. Also contemplated are methods of saccharification the disclosed fermented beverage, or the disclosed uses of the end of fermentation product, wherein the fermented beverage or end fermentation product is selected from the group consisting of i) a beer selected from the group consisting of full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, and non-alcoholic malt liquor; and ii) cereal or malt beverages selected from the group consisting of fruit flavoured malt beverages, liquor flavoured malt beverages, and coffee flavoured malt beverages.

Also contemplated is a method of producing a food composition, comprising combining (i) one or more food ingredients, and (ii) an isolated AfGA1TR or variant thereof of claims 4-15, wherein said pullulanase and said isolated AfGA1TR or variant thereof catalyze the hydrolysis of starch components present in the food ingredients to produce glucose. The food composition may be selected from the group consisting of a food product, a baking composition, a food additive, an animal food product, a feed product, a feed additive, an oil, a meat, and a lard. The food ingredients may comprise a baking ingredient or an additive. The one or more food ingredients may be selected from the group consisting of flour; an anti-staling amylase; a phospholipase; a phospholipid; a maltogenic alpha-amylase or a variant, homologue, or mutants thereof which has maltogenic alpha-amylase activity; a bakery xylanase (EC 3.2.1.8); and a lipase. The one or more food ingredients may be selected from the group consisting of (i) a maltogenic alpha-amylase from *Bacillus stearothermophilus*, (ii) a bakery xylanase is from *Bacillus, Aspergillus, Thermomyces* or *Trichoderma*, (iii) a glycolipase from *Fusarium heterosporum*. The food composition may comprise a dough or a dough product, preferably a processed dough product. The method may comprise baking the food composition to produce a baked good. The method may further comprise (i) providing a starch medium; (ii) adding to the starch medium the pullulanase and the AfGA1TR or variant thereof; and (iii) applying heat to the starch medium during or after step (b) to produce a baked good.

Also contemplated is a composition for use in producing a food composition, comprising an AfGA1TR or variant thereof. Also contemplated is a use of AfGA1TR or variant thereof in preparing a food composition. The food composition may comprise a dough or a dough product, preferably a processed dough product. The food composition may be a bakery composition. Also contemplated is use of AfGA1TR or variant thereof in a dough product to retard or reduce staling, preferably detrimental retrogradation, of the dough product.

BRIEF DESCRIPTION OF THE DRAWINGS

The accompanying drawings are incorporated in, and constitute a part of, this specification and illustrate various methods and compositions disclosed herein. In the drawings:

FIGS. 1A-B depict a ClustalW alignment of the AfGA1 catalytic core and carbohydrate binding domain (residues 27-476 and 524-631 of SEQ ID NO: 1, respectively or the full length, with the corresponding residues of glucoamylases from: *Aspergillus fumigatus* A1163 (AfGA2)(residues 27-476 and 524-631 of SEQ ID NO: 2, respectively); *Neosartorya fisheri* NRRL 181 (residues 28-476 and 520-627 of SEQ ID NO: 3, respectively); *Talaromyces stipitatus* ATCC 10500 (residues 28-478 and 530-637 of SEQ ID NO: 4, respectively); *Penicillium marneffei* ATCC 18224 (residues 31-481 and 534-641 of SEQ ID NO: 5, respectively); and *Aspergillus nidulans* FGSC A4 (residues 55-493 and 544-661 of SEQ ID NO: 6, respectively). Residues designated by an asterisk in FIG. 1 are AfGA1 residues corresponding to conserved residues in SEQ ID NOS: 1-6.

DETAILED DESCRIPTION

Figure 2:
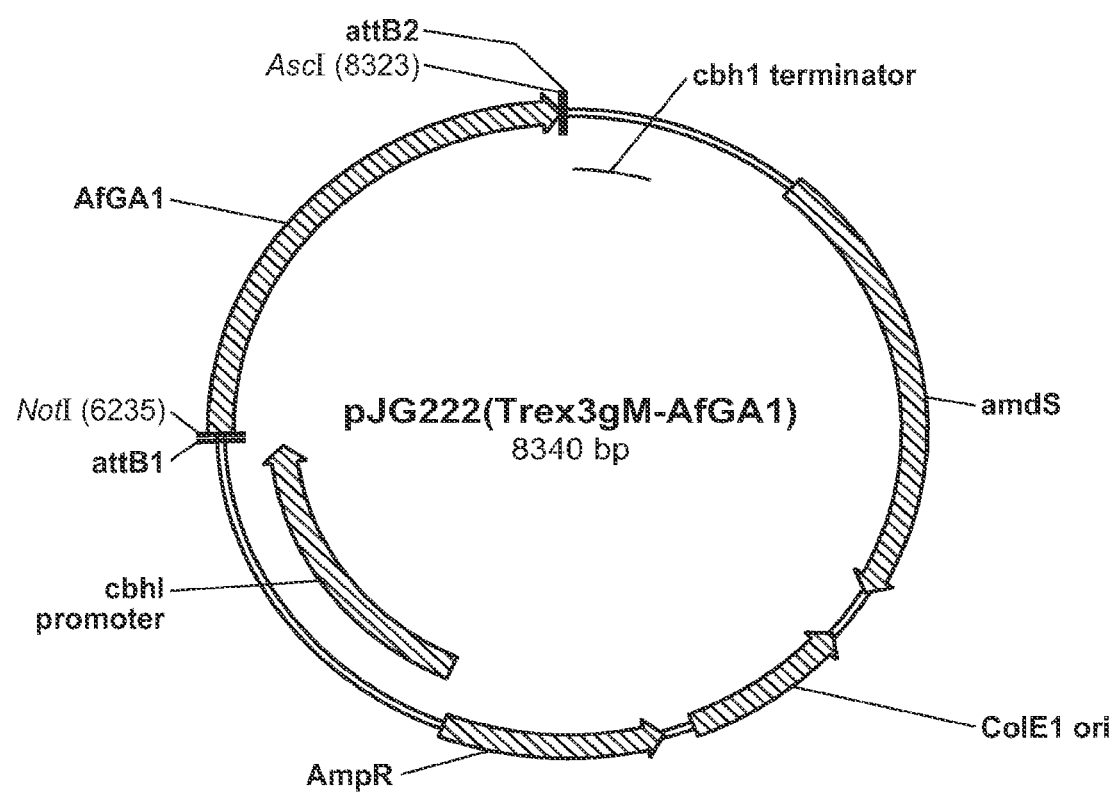
FIG. 2 depicts a map of a pJG222 expression vector comprising a polynucleotide that encodes an AfGA1 polypeptide, pJG222 (Trex3gM-AfGA1).

Fungal glucoamylases from *Aspergillus fumigatus* (AfGA1TR or AfGA2TR) and variants thereof are provided. AfGA1TR or a variant thereof has a pH optimum of pH 5.0 and at least 70% activity over a range of pH 3.5 to pH 7.5. The enzyme has an optimum temperature of 68° C. and at least 70% activity over a temperature range of 55°–74° C., when tested at pH 5.0. AfGA2TR or a variant thereof has a pH optimum of pH 5.3 and at least 70% activity over a range of pH 3.3 to pH 7.3. The enzyme has an optimum temperature of 69° C. and at least 70% activity over a temperature range of 61°–74° C., when tested at pH 5.0. These properties allow these enzymes to be used in combination with a α-amylase under the same reaction conditions. This obviates the necessity of running a saccharification reaction as a batch process, where the pH and temperature should be adjusted for optimal use of the α-amylase or glucoamylase.

Exemplary applications for glucoamylases such as AfGATRs (including AfGA1TR and AfGA2TR) or variants thereof can be used in a process of starch saccharification, e.g., SSF, the preparation of food compositions, the preparation of cleaning compositions, such as detergent compositions for cleaning laundry, dishes, and other surfaces, for textile processing (e.g., desizing). AfGATRs advantageously catalyze starch saccharification to an oligosaccharide composition significantly enriched in DP1 (i.e., glucose) compared to the products of saccharification catalyzed by *Aspergillus niger* glucoamylase (AnGA). AfGATRs can be secreted by a host cell with other enzymes during fermentation or SSF. For example, AfGATRs demonstrate a greater rate of saccharification over AnGA, producing more than 96% glucose in 24 hours. AfGATRs can also be used at a lower dosage than AnGA to produce comparable levels of DP1. At least a 50% dose saving can be expected. AfGATRs are also statistically significantly more thermostable than AnGA during saccharification. AfGATRs can be used in combination with enzymes derived from plants (e.g., cereals and grains). AfGATRs also can be used in combination with enzymes secreted by, or endogenous to, a host cell such as *T. reesei*. For example, AfGATRs can be added to a saccharification, fermentation or SSF process during which one or more amylases, glucoamylases, proteases, lipases, phytases, esterases, redox enzymes, transferases, or other enzymes that are secreted by the production host. AfGATRs may be combined with an accessory alpha-amylase to further improve the rate of saccharification. For example, the addition of 0.1 SSU/gds of AkAA improves the rate of saccharification. When combined with AkAA and a pullulanase, AfGATRs were found to have lower DP3 by 0.1% than AnGA at the same glucose yield in a single pH process. AfGATRs may also work in combination with endogenous non-secreted production host enzymes. In another example, AfGATRs can be secreted by a production host cell with other enzymes during fermentation or SSF. The AfGATRs may also be effective in direct hydrolysis of starch for syrup and/or biochemicals (e.g., alcohols, organic acids, amino acids, other biochemicals and biomaterials) where the reaction temperature is below the gelatinization temperature of substrate.

1. Definitions & Abbreviations

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following terms are provided below.

1.1. Abbreviations and Acronyms

The following abbreviations/acronyms have the following meanings unless otherwise specified:

ABTS 2,2-azino-bis-3-ethylbenzothiazoline-6-sulfonic acid
AcAmyl *Aspergillus clavatus* α-amylase
AE alcohol ethoxylate
AEO alcohol ethoxylate
AEOS alcohol ethoxysulfate
AES alcohol ethoxysulfate
AfGA *Aspergillus fumigatus* glucoamylase
AfGA1 *Aspergillus fumigatus* glucoamylase 1
AfGA2 *Aspergillus fumigatus* glucoamylase 2
AfGATR *Aspergillus fumigatus* glucoamylase expressed in *Trichoderma reesei*
AfGA1TR *Aspergillus fumigatus* glucoamylase 1 expressed in *Trichoderma reesei*
AfGA2TR *Aspergillus fumigatus* glucoamylase 2 expressed in *Trichoderma reesei*
AkAA *Aspergillus kawachii* α-amylase
AnGA *Aspergillus niger* glucoamylase
AOS α-olefinsulfonate
AS alkyl sulfate
cDNA complementary DNA
CMC carboxymethylcellulose
DE dextrose equivalent
DNA deoxyribonucleic acid
DPn degree of saccharide polymerization having n subunits
ds or DS dry solids
DTMPA diethylenetriaminepentaacetic acid
EC Enzyme Commission
EDTA ethylenediaminetetraacetic acid
EO ethylene oxide (polymer fragment)
EOF End of Fermentation
FGSC Fungal Genetics Stock Center GA glucoamylase
GAU/g ds glucoamylase activity unit/gram dry solids
HFCS high fructose corn syrup
HgGA *Humicola grisea* glucoamylase
HS higher sugar
IPTG isopropyl β-D-thiogalactoside
IRS insoluble residual starch
kDa kiloDalton
LAS linear alkylbenzenesulfonate
MW molecular weight
MWU modified Wohlgemuth unit; $1.6 \times 10^{-5}$ mg/MWU=unit of activity
NCBI National Center for Biotechnology Information
NOB S nonanoyloxybenzenesulfonate
NTA nitriloacetic acid
OxAm Purastar HPAM 5000L (Danisco US Inc.)
PAHBAH p-hydroxybenzoic acid hydrazide
PEG polyethyleneglycol
PI isoelectric point
ppm parts per million
PVA poly(vinyl alcohol)
PVP poly(vinylpyrrolidone)
RNA ribonucleic acid
SAS alkanesulfonate
SDS-PAGE sodium dodecyl sulfate polyacrylamide gel electrophoresis
SSF simultaneous saccharification and fermentation
SSU/g solid soluble starch unit/gram dry solids
sp. species
TAED tetraacetylethylenediamine
TrGA *Trichoderma reesei* glucoamylase
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm grams
micrograms
mg milligrams
kg kilograms
μL and μl microliters
mL and ml milliliters
mm millimeters
μm micrometer
M molar
mM millimolar
μM micromolar
U units
sec seconds
min(s) minute/minutes
hr(s) hour/hours
DO dissolved oxygen
Ncm Newton centimeter
ETOH ethanol
eq. equivalents
N normal

1.2. Definitions

The terms "amylase" or "amylolytic enzyme" refer to an enzyme that is, among other things, capable of catalyzing the degradation of starch. α-Amylases are hydrolases that cleave the α-D-(1→4) O-glycosidic linkages in starch. Generally, α-amylases (EC 3.2.1.1; α-D-(1→4)-glucan glucano-hydrolase) are described as endo-acting enzymes cleaving α-D-(1→4) O-glycosidic linkages within the starch molecule in a random fashion yielding polysaccharides containing three or more (1-4)-α-linked D-glucose units. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the polysaccharide molecule from the non-reducing end of the substrate. β-amylases, α-glucosidases (EC 3.2.1.20; α-D-glucoside glucohydrolase), glucoamylase (EC 3.2.1.3; α-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

As used herein, the term "glucoamylase" (EC 3.2.1.3) (otherwise known as glucan 1,4-α-glucosidase; glucoamylase; amyloglucosidase; γ-amylase; lysosomal α-glucosidase; acid maltase; exo-1,4-α-glucosidase; glucose amylase; γ-1,4-glucan glucohydrolase; acid maltase; 1,4-α-D-glucan glucohydrolase; or 4-α-D-glucan glucohydrolase) refers to a class of enzymes that catalyze the release of D-glucose from the non-reducing ends of starch and related oligo- and polysaccharides. These are exo-acting enzymes, which release glucosyl residues from the non-reducing ends of amylose and amylopectin molecules. The enzymes also hydrolyze alpha-1, 6 and alpha-1, 3 linkages although at much slower rates than alpha-1, 4 linkages. The term "hydrolysis of starch" refers to the cleavage of glucosidic bonds with the addition of water molecules.

The term "pullulanase" (E.C. 3.2.1.41, pullulan 6-glucanohydrolase) refers to a class of enzymes that are capable of hydrolyzing alpha 1-6 glucosidic linkages in an amylopectin molecule.

"Enzyme units" herein refer to the amount of product formed per time under the specified conditions of the assay. For example, a "glucoamylase activity unit" (GAU) is defined as the amount of enzyme that produces 1 g of glucose per hour from soluble starch substrate (4% DS) at 60° C., pH 4.2. A "soluble starch unit" (SSU) is the amount of enzyme that produces 1 mg of glucose per minute from soluble starch substrate (4% DS) at pH 4.5, 50° C. DS refers to "dry solids."

As used herein "dry solids" content refers to the total solids of a slurry in a dry weight percent basis. The term "slurry" refers to an aqueous mixture containing insoluble solids. The term "high ds" refers to an aqueous starch slurry containing dry solids greater than 38%.

The term "Brix" refers to a well-known hydrometer scale for measuring the sugar content of a solution at a given temperature. The Brix scale measures the number of grams of sucrose present per 100 grams of aqueous sugar solution (the total solubilized solid content). Brix measurements are frequently performed using a hydrometer or refractometer.

The term "degree of polymerization" (DP) refers to the number (n) of anhydro-glucopyranose units in a given saccharide. Examples of DP1 are monosaccharides, such as glucose and fructose. Examples of DP2 are disaccharides, such as maltose and sucrose. HS or DP4+(>DP3) denotes polymers with a degree of polymerization of greater than 3. The term "DE," or "dextrose equivalent," is defined as the percentage of reducing sugar, i.e., D-glucose, as a fraction of total carbohydrate in a syrup. It is an industry standard for the concentration of total reducing sugars, and is expressed as % D-glucose on a dry weight basis. Unhydrolyzed granular starch has a DE that is essentially 0 and D-glucose has a DE of 100.

As used herein the term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, grasses, tubers and roots, and more specifically materials obtained from wheat, barley, corn, rye, rice, sorghum, brans, cassava, millet, potato, sweet potato, and tapioca. The term "starch" includes granular starch. The term "granular starch" refers to raw, i.e., uncooked starch, e.g., starch that has not been subject to gelatinization.

The term "glucose syrup" refers to an aqueous composition containing glucose solids. Glucose syrup will have a DE of at least 20. In some embodiments, glucose syrup will not contain more than 21% water and will not contain less than 25% reducing sugar calculated as dextrose. The glucose syrup will include at least 90% D-glucose, perhaps at least 95% D-glucose. In some embodiments, the terms glucose and glucose syrup are used interchangeably.

The term "total sugar content" refers to the total sugar content present in a starch composition.

The term "Refractive Index Dry Substance" (RIDS) is defined as the determination of the refractive index of a starch solution at a known DE at a controlled temperature then converting the RI to dry substance using an appropriate relationship, such as the Critical Data Tables of the Corn Refiners Association.

The term "contacting" refers to the placing of the respective enzymes in sufficiently close proximity to the respective substrate to enable the enzymes to convert the substrate to the end-product. Those skilled in the art will recognize that mixing solutions of the enzyme with the respective substrates can effect contacting.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide. Further, as used herein and as will be clear from the context, it will be appreciated that referring to a particular sequence as "wild-type" is not meant to imply that other sequences in the example that are not affixed with the pre-fix "wild-type" aren't wild type as well.

As used herein, the term "comparable" in reference to expression level refers to no more than 20% variance between the samples of interest, unless the context clearly dictates otherwise.

Reference to the wild-type protein is understood to include the mature form of the protein. A "mature" polypeptide means a polypeptide or variant thereof from which a signal sequence is absent. For example, the signal sequence may be cleaved during expression of the polypeptide. The mature AfGA1 or AfGA2 is 612 amino acids in length covering positions 1-612 of SEQ ID NO: 1 and SEQ ID NO: 2 respectively, where positions are counted from the N-terminus. The signal sequence of the wild-type AfGA1 or AfGA2 is 19 amino acids in length and has the sequence set forth in SEQ ID NO: 11. Mature AfGA1, AfGA2, or variant thereof may comprise a signal sequence taken from different proteins. The mature protein can be a fusion protein between the mature polypeptide and a signal sequence polypeptide.

The putative "catalytic core" of AfGA1, AfGA2 or a variant thereof spans residues 41-453 of SEQ ID NO: 1. Amino acid residues 534-630 constitute the putative "carbohydrate binding domain" of AfGA1, AfGA2 or a variant thereof. The "linker" or "linker region" of AfGA1, AfGA2, or a variant thereof spans a region between the "catalytic core" and "carbohydrate binding domain."

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

In the case of the present enzymes, such as a glucoamylase, "activity" refers to enzymatic activity, which can be measured as described, herein.

The term "recombinant," when used in reference to a subject cell, nucleic acid, protein or vector, indicates that the subject has been modified from its native state. Thus, for example, recombinant cells express genes that are not found within the native (non-recombinant) form of the cell, or express native genes at different levels or under different conditions than found in nature. Recombinant nucleic acids differ from a native sequence by one or more nucleotides and/or are operably-linked to heterologous sequences, e.g., a heterologous promoter in an expression vector. Recombinant proteins may differ from a native sequence by one or more amino acids and/or are fused with heterologous sequences. A vector comprising a nucleic acid encoding an AfGA1, AfGA2 or variant thereof is a recombinant vector.

The terms "recovered," "isolated," and "separated," refer to a compound, protein (polypeptides), cell, nucleic acid, amino acid, or other specified material or component that is removed from at least one other material or component with which it is naturally associated as found in nature, e.g., an AfGATR isolated from a recombinant host cell. An "isolated" AfGATR, or variant thereof includes, but is not limited to, a culture broth containing secreted AfGATR expressed in a heterologous host cell (i.e., a host cell this not *A. fumigatus*).

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability," with reference to an enzyme, refer to the ability of the enzyme to retain activity after exposure to an elevated temperature. The thermostability of an enzyme, such as an amylase enzyme, can be measured by its $T_m$, at which half the enzyme activity is lost under defined conditions. The $T_m$ may be calculated by measuring residual glucoamylase activity following exposure to (i.e., challenge by) an elevated temperature.

A "pH range," with reference to an enzyme, refers to the range of pH values under which the enzyme exhibits catalytic activity.

As used herein, the terms "pH stable" and "pH stability," with reference to an enzyme, relate to the ability of the enzyme to retain activity over a wide range of pH values for a predetermined period of time (e.g., 15 min., 30 min., and 1 hour).

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

As used herein, "hybridization" refers to the process by which one strand of nucleic acid forms a duplex with, i.e., base pairs with, a complementary strand, as occurs during blot hybridization techniques and PCR techniques. Stringent hybridization conditions are exemplified by hybridization under the following conditions: 65° C. and 0.1×SSC (where 1×SSC=0.15 M NaCl, 0.015 M Na$_3$ citrate, pH 7.0). Hybridized, duplex nucleic acids are characterized by a melting temperature ($T_m$), where one-half of the hybridized nucleic acids are unpaired with the complementary strand. Mismatched nucleotides within the duplex lower the $T_m$. A nucleic acid encoding a variant glucoamylase may have a $T_m$ reduced by 1° C. to 3° C. or more compared to a duplex formed between the nucleotide of SEQ ID NO: 8 and its identical complement.

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection," "transformation" or "transduction," as known in the art.

A "host strain" or "host cell" is an organism into which an expression vector, phage, virus, or other DNA construct, including a polynucleotide encoding a polypeptide of interest (e.g., an AfGATR or variant thereof) has been introduced. Exemplary host strains are microorganism cells (e.g., bacteria, filamentous fungi, and yeast, such as *T. reesei*) capable of expressing the polypeptide of interest and/or fermenting saccharides. The term "host cell" includes protoplasts created from cells.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes, and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers, and sequences that control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

As used herein, a "swatch" is a piece of material such as a fabric that has a stain applied thereto. The material can be, for example, fabrics made of cotton, polyester, or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

As used herein, a "smaller swatch" is a section of the swatch that has been cut with a single-hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The smaller swatch can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of metal, plastic, glass, ceramic, or another suitable material that is coated with the soil substrate. The one or more coated beads are then placed into wells of 96-, 48-, or 24-well plates or larger formats, containing suitable buffer and enzyme.

As used herein, "a cultured cell material comprising an AfGATR," or similar language, refers to a cell lysate or supernatant (including media) that includes an AfGATR or a variant thereof as a component. The cell material may be from a heterologous host that is grown in culture for the purpose of producing the AfGATR or variant thereof.

"Percent sequence identity" means that a variant has at least a certain percentage of amino acid residues identical to a wild-type AfGA1 or AfGA2, when aligned using the CLUSTAL W algorithm with default parameters. See Thompson et al. (1994) Nucleic Acids Res. 22:4673-4680. Default parameters for the CLUSTAL W algorithm are:
  Gap opening penalty: 10.0
  Gap extension penalty: 0.05
  Protein weight matrix: BLOSUM series
  DNA weight matrix: IUB
  Delay divergent sequences %: 40
  Gap separation distance: 8
  DNA transitions weight: 0.50
  List hydrophilic residues: GPSNDQEKR
  Use negative matrix: OFF
  Toggle Residue specific penalties: ON
  Toggle hydrophilic penalties: ON
  Toggle end gap separation penalty OFF.

Deletions are counted as non-identical residues, compared to a reference sequence. Deletions occurring at either terminus are included. For example, a variant with six amino acid deletions of the C-terminus of the mature AfGA1 polypeptide of SEQ ID NO: 12 would have a percent sequence identity of 99% (606/612 identical residues×100, rounded to the nearest whole number) relative to the mature polypeptide. Such a variant would be encompassed by a variant having "at least 99% sequence identity" to a mature AfGA1 polypeptide.

"Fused" polypeptide sequences are connected, i.e., operably linked, via a peptide bond between the two polypeptide sequences.

The term "filamentous fungi" refers to all filamentous forms of the subdivision Eumycotina.

The phrase "simultaneous saccharification and fermentation (SSF)" refers to a process in the production of biochemicals in which a microbial organism, such as an ethanologenic microorganism, and at least one enzyme, such as AfGA or a variant thereof, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

As used herein "ethanologenic microorganism" refers to a microorganism with the ability to convert a sugar or oligosaccharide to ethanol.

The term "fermented beverage" refers to any beverage produced by a method comprising a fermentation process, such as a microbial fermentation, e.g., a bacterial and/or yeast fermentation.

"Beer" is an example of such a fermented beverage, and the term "beer" is meant to comprise any fermented wort produced by fermentation/brewing of a starch-containing plant material. Often, beer is produced exclusively from malt or adjunct, or any combination of malt and adjunct. Examples of beers include: full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e.g., citrus flavored, such as lemon-, orange-, lime-, or berry-flavored malt beverages, liquor flavored malt beverages, e.g., vodka-, rum-, or tequila-flavored malt liquor, or coffee flavored malt beverages, such as caffeine-flavored malt liquor, and the like.

The term "malt" refers to any malted cereal grain, such as malted barley or wheat.

The term "adjunct" refers to any starch and/or sugar containing plant material which is not malt, such as barley or wheat malt. Examples of adjuncts include common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like.

The term "mash" refers to an aqueous slurry of any starch and/or sugar containing plant material, such as grist, e.g., comprising crushed barley malt, crushed barley, and/or other adjunct or a combination thereof, mixed with water later to be separated into wort and spent grains.

The term "wort" refers to the unfermented liquor run-off following extracting the grist during mashing.

"Iodine-positive starch" or "IPS" refers to (1) amylose that is not hydrolyzed after liquefaction and saccharification, or (2) a retrograded starch polymer. When saccharified starch or saccharide liquor is tested with iodine, the high DPn amylose or the retrograded starch polymer binds iodine and produces a characteristic blue color. The saccharide liquor is thus termed "iodine-positive saccharide," "blue saccharide," or "blue sac."

The terms "retrograded starch" or "starch retrogradation" refer to changes that occur spontaneously in a starch paste or gel on ageing.

The term "about" refers to ±15% to the referenced value.

2. *Aspergillus fumigatus* Glucoamylases (AfGA1 and AfGA2)

An isolated and/or purified AfGA1, or a variant thereof, polypeptide from *A. fumigatus* sp., which has glucoamylase activity is provided. The glucoamylase consists of three distinct structural domains, including a catalytic domain, followed by a linker region, that are in turn connected to a starch binding domain. The AfGA1 polypeptide can be the mature AfGA1 polypeptide depicted in SEQ ID NO: 12. The polypeptides may be fused to additional amino acid sequences at the N-terminus and/or C-terminus. Additional N-terminal sequences can be a signal peptide, which may have the sequence shown in SEQ ID NO:11, for example. Other amino acid sequences fused at either termini include fusion partner polypeptides useful for labeling or purifying the protein.

For example, the AfGA1 precursor includes the sequence below (SEQ ID NO: 1):

```
MPRLSYALCALSLGHAAIAAPQLSARATGSLDSWLGTETTVALNGILANI

GADGAYAKSAKPGIIASPSTSEPDYYYTWTRDAALVTKVLVDLFRNGNL

GLQKVITEYVNSQAYLQTVSNPSGGLASGGLAEPKYNVDMTAFTGAWGRP

QRDGPALRATALIDFGNWLIDNGYSSYAVNNIWPIVRNDLSYVSQYWSQS

GFDLWEEVNSMSFFTVAVQHRALVEGSTFAKRVGASCSWCDSQAPQILCY

MQSFWTGSYINANTGGGRSGKDANTVLASIHTFDPEAGCDDTTFQPCSPR

ALANHKVYTDSFRSVYAINSGIPQGAAVSAGRYPEDVYYNGNPWFLTTLA

AAEQLYSAIYQWKKIGSISITSTSLAFFKDIYSSAAVGTYASSTSTFTDI

INAVKTYADGYVSIVQAHAMNNGSLSEQFDKSSGLSLSARDLTWSYAAFL

TANMRRNGVVPAPWGAASANSVPSSCSMGSATGTYSTATATSWPSTLTSG

SPGSTTTVGTTTSTTSGTAAETACATPTAVAVTFNEIATTTYGENVYIVG

SISELGNWDTSKAVALSASKYTSSNNLWYVSVTLPAGTTFEYKYIRKESD

GSIVWESDPNRSYTVPAACGVSTATENDTWQ
```

```
SISELGNWDTSKAVALSASKYTSSNNLWYVSVTLPAGTTFEYKYIRKESD

GSIVWESDPNRSYTVPAACGVSTATENDTWR
```

The bolded amino acids above constitute a C-terminal carbohydrate binding (CBM) domain (SEQ ID NO: 7) for both AfGA1 and AfGA2. A glycosylated linker region connects the N-terminal catalytic core with the CBM domain. The CBM domain in AfGA1 and AfGA2 is conserved with a CBM20 domain found in a large number of starch degrading enzymes, including alpha-amylases, beta-amylases, glucoamylases, and cyclodextrin glucanotransferases. CBM20 folds as an antiparallel beta-barrel structure with two starch-binding sites 1 and 2. These two sites are thought to differ functionally: site 1 may act as the initial starch recognition site, whereas site 2 may be involved in specific recognition of appropriate regions of starch. See Sorimachi et al. (1997) "Solution structure of the granular starch binding domain of *Aspergillus niger* glucoamylase bound to beta-cyclodextrin," Structure 5(5): 647-61. Residues in the AfGA1 and AfGA2 CBM domain that are conserved with starch binding sites 1 and 2 indicated in the sequence below by the numbers 1 and 2, respectively:

```
                                                            (SEQ ID NO: 7)
FNEIATTTYGENVYIVGSISELGNWDTSKAVALSASKYTSSNNLWYVSVTLPAGTTFEYKYIRKESDGSI
    222222            1    1 1111      2 2222   22

VWESDPNRSYTVPAACGVSTATENDTW.
1
```

An isolated and/or purified AfGA2, or a variant thereof, polypeptide from *A. fumigatus* sp., which has glucoamylase activity is also provided. The glucoamylase consists of three distinct structural domains, including a catalytic domain, followed by a linker region, that are in turn connected to a starch binding domain. The AfGA2 polypeptide can be the mature AfGA2 polypeptide depicted in SEQ ID NO: 13. The polypeptides may be fused to additional amino acid sequences at the N-terminus and/or C-terminus. Additional N-terminal sequences can be a signal peptide, which may have the sequence shown in SEQ ID NO: 11, for example. Other amino acid sequences fused at either termini include fusion protein polypeptides useful for labeling or purifying the protein.

For example, the AfGA2 precursor includes the sequence below (SEQ ID NO: 2):

```
MPRLSYALCALSLGHAAIAAPQLSARATGSLDSWLGTETTVALNGILANI

GADGAYAKSAKPGIIASPSTSEPDYYYTWTRDAALVTKVLVDLFRNGNL

GLQKVITEYVNSQAYLQTVSNPSGGLASGGLAEPKYNVDMTAFTGAWGRP

QRDGPALRATALIDFGNWLIDNGYSSYAVNNIWPIVRNDLSYVSQYWSQS

GFDLWEEVNSMSFFTVAVQHRALVEGSTFAKRVGASCSWCDSQAPQILCY

MQSFWTGSYINANTGGGRSGKDANTVLASIHTFDPEAGCDDTTFQPCSPR

ALANHKVYTDSFRSVYAINSGIPQGAAVSAGRYPEDVYYNGNPWFLTTLA

AAEQLYDAIYQWKKIGSISITSTSLAFFKDIYSSAAVGTYASSTSTFTDI

INAVKTYADGYVSIVQAHAMNNGSLSEQFDKSSGLSLSARDLTWSYAAFL

TANMRRNGVVPAPWGAASANSVPSSCSMGSATGTYSTATATSWPSTLTSG

SPGSTTTVGTTTSTTSGTATETACATPTAVAVTFNEIATTTYGENVYIVG
```

A variant AfGA1 or AfGA2 may comprise some or no amino acid residues of the CBM domain of SEQ ID NO: 7. A variant alternatively may comprise a CBM domain with at least 80%, 85%, 90%, 95%, or 98% sequence identity to the CBM domain of SEQ ID NO: 7. A variant may comprise a heterologous or an engineered CBM20 domain.

The AfGA or variant thereof may be expressed in a eukaryotic host cell, e.g., a filamentous fungal cell that allows proper glycosylation of the linker sequence, for example.

A representative polynucleotide encoding AfGA1 is the polynucleotide sequence set forth in SEQ ID NO: 8. A representative polynucleotide encoding AfGA2 is the polynucleotide sequence set forth in SEQ ID NO: 14. (*NCBI Reference Sequence* NC 007195, the *A. fumigatus* genome.) The polypeptide sequence, MPRLSYALCALSLGHAAIA (SEQ ID NO: 11), shown in italics in the AfGA1 and AfGA2 precursor sequences above, is an N-terminal signal peptide that is cleaved when the protein is expressed in an appropriate host cell.

The polypeptide sequence of AfGA1 is similar to other fungal glucoamylases, including AfGA2. For example, AfGA1 has the high sequence identity to the following fungal glucoamylases:
  99% sequence identity to the glycosyl hydrolase from *Aspergillus fumigatus* A1163 (SEQ ID NO: 2)(AfGA2);
  92% sequence identity to the glycosyl hydrolase from *Neosartorya fisheri* NRRL 181 (SEQ ID NO: 3); and
  82% sequence identity to the putative glucoamylase from *Talaromyces stipitatus* ATCC 10500 (SEQ ID NO: 4);
  81% sequence identity to the putative glucoamylase from *Penicillium marneffei* ATCC 18224 (SEQ ID NO: 5);
  81% sequence identity to the hypothetical glucoamylase from *Aspergillus nidulans* FGSC A4 (SEQ ID NO: 6);

Sequence identity was determined by a BLAST alignment, using the precursor form of the AfGA1 of SEQ ID NO: 1 as the query sequence. See Altschul et al. (1990) *J. Mol. Biol.* 215: 403-410. Sequence identity may also optionally be based on the mature form of the enzyme.

A variant of an AfGA1 polypeptide is provided. The variant can consist of or comprise a polypeptide with at least 80%, at least 90%, at least 95%, at least 98%, or at least 99% amino acid sequence identity to the polypeptide of residues 1-631 of SEQ ID NO: 1, wherein the variant comprises one or more amino acid modifications selected from a substitution, insertion, or deletion of one or more corresponding amino acids in SEQ ID NO: 2-6. A variant of an AfGA2 polypeptide is also provided. The variant can consist of, or comprise, a polypeptide with at least 80%, at least 90%, at least 95%, at least 98%, or at least 99% amino acid sequence identity to the polypeptide of residues 1-631 of SEQ ID NO: 2, wherein the variant comprises one or more amino acid modifications selected from a substitution, insertion, or deletion of one or more corresponding amino acids in SEQ ID NO: 1 and/or 3-6. For example, a variant consisting of a polypeptide with at least 99% sequence identity to the polypeptide of residues 1-612 of SEQ ID NO:1 may have one to six amino acid substitutions, insertions, or deletions, compared to the AfGA1 of SEQ ID NO: 1. The insertions or deletions may be may at either termini of the polypeptide, for example. Alternatively, the variant can "comprise" a polypeptide consisting of a polypeptide with at least 80%, at least 90%, at least 95%, at least 98%, or at least 99% amino acid sequence identity to the polypeptide of 1-631 of SEQ ID NO: 1 or 2. In a variant, additional amino acid residues may be fused to either termini of the polypeptide. The variant may be glycosylated, regardless of whether the variant "comprises" or "consists" of a given amino acid sequence.

A ClustalW alignment between AfGA1 (SEQ ID NO: 1); AfGA2 (SEQ ID NO: 2); the glucoamylase from *Neosartorya fisheri* NRRL 181 (SEQ ID NO: 3); the glucoamylase from *Talaromyces stipitatus* ATCC 10500 (SEQ ID NO: 4); the glucoamylase from *Penicillium marneffei* ATCC 18224 (SEQ ID NO: 5); and the glucoamylase *Aspergillus nidulans* FGSC A4 (SEQ ID NO: 6) is shown in FIG. 1. See Thompson et al. (1994) *Nucleic Acids Res.* 22:4673-4680. As a general rule, the degree to which an amino acid is conserved in an alignment of related protein sequences is proportional to the relative importance of the amino acid position to the function of the protein. That is, amino acids that are common in all related sequences likely play an important functional role, and cannot be easily substituted. Likewise, positions that vary between the sequences likely can be substituted with other amino acids or otherwise modified, while maintaining the activity of the protein.

The alignments shown in FIG. 1, for example, can guide the construction of variant AfGA polypeptides having glucoamylase activity. Variants of the AfGA1 polypeptide of SEQ ID NO: 1 can include, but are not limited to, those with an amino acid modification selected from a substitution, insertion, or deletion of a corresponding amino acid in a polypeptide selected from the group consisting of SEQ ID NOs: 2 (AfGA2), 3, 4, 5, and 6. Correspondence between positions in the AfGA1 of SEQ ID NO: 1 and the glucoamylases of SEQ ID NOs: 2, 3, 4, 5 and 6 is determined with reference to the alignment shown in FIG. 1. For example, a variant AfGA1 polypeptide can have the substitution D23N, where Asn is the corresponding amino acid in SEQ ID NO: 6, referring to the alignment in FIG. 1. Variant AfGA1 polypeptides also include, but are not limited to, those with 1, 2, 3, or 4 randomly selected amino acid modifications. Amino acid modifications can be made using well-known methodologies, such as oligo-directed mutagenesis. Similarly, variants of the AfGA2 polypeptide of SEQ ID NO: 2 can include, but are not limited to, those with an amino acid modification selected from a substitution, insertion, or deletion of a corresponding amino acid in a polypeptide selected from the group consisting of SEQ ID NOS: 1 (AfGA1), 3, 4, 5, and 6.

Nucleic acids encoding the AfGA1 polypeptide or variant thereof also are provided. A nucleic acid encoding AfGA1 can be genomic DNA. Or, the nucleic acid can be a cDNA comprising SEQ ID NO: 8. Similarly, nucleic acids encoding the AfGA2 polypeptide or variant thereof also are provided. A nucleic acid encoding AfGA2 can also be genomic DNA. Or, the nucleic acid can be a cDNA comprising SEQ ID NO: 14. As is well understood by one skilled in the art, the genetic code is degenerate, meaning that multiple codons in some cases may encode the same amino acid. Nucleic acids include all genomic DNA, mRNA, and cDNA sequences that encode an AfGA1, AfGA2 or variant thereof.

The AfGA1, AfGA2 or variants thereof may be "precursor," "immature," or "full-length," in which case they include a signal sequence, or "mature," in which case they lack a signal sequence. The variant glucoamylases may also be truncated at the N- or C-termini, so long as the resulting polypeptides retain glucoamylases activity

2.1. AfGA Variant Characterization

Variant AfGA polypeptides retain glucoamylase activity. They may have a specific activity higher or lower than the wild-type AfGA polypeptide. Additional characteristics of the AfGA variant include stability, pH range, temperature profile, oxidation stability, and thermostability, for example. For example, the variant may be pH stable for 24-60 hours from pH 3 to about pH 8, e.g., pH 3.0-7.8; e.g., pH 3.0-7.5; pH 3.5-7.0; pH 4.0-6.7; or pH 5.0. An AfGA variant can be expressed at higher levels than the wild-type AfGA, while retaining the performance characteristics of the wild-type AfGA. AfGA variants also may have altered oxidation stability in comparison to the parent glucoamylase. For example, decreased oxidation stability may be advantageous in compositions for starch liquefaction. The variant AfGA, have altered temperature profile compared to the wild-type glucoamylase. Such AfGA variants are advantageous for use in baking or other processes that require elevated temperatures. Levels of expression and enzyme activity can be assessed using standard assays known to the artisan skilled in this field, including those disclosed below

3. Production of AfGA and Variants Thereof

The AfGA or variant thereof can be isolated from a host cell, for example by secretion of the AfGA or variant from the host cell. A cultured cell material comprising AfGA, or variant thereof, can be obtained following secretion of the AfGA or variant from the host cell. The AfGA, or variant thereof, is optionally purified prior to use. The AfGA gene can be cloned and expressed according to methods well known in the art. Suitable host cells include bacterial, plant, or yeast cells, e.g., filamentous fungal cells. Particularly useful host cells include *Trichoderma reesei*. *Trichoderma reesei* host cells express AfGATRs at higher, or at least comparable, levels to natively expressed AfGA *Aspergillus fumigatus*.

In some embodiments, the AfGA is heterologously expressed in a host at at least 10 g/liter. In some embodiments, the AfGA is heterologously expressed at least 15, 20, 25, 30, 35, 40, 45, 50, 55, 60, 65, 70, 75, 80, 90, 100, or 110 g/liter. In some embodiments, the AfGA is heterologously expressed in a *Trichoderma reesei* host, wherein the expression is at least 15, 20, 25, 30, 35, 40, 45, 50, 55, 60, 65, 70, 75, 80, 90, 100, or 110 g/liter. In some embodiments, the AfGA is heterologously expressed in an *Aspergillus* host, wherein the expression is at least 15, 20, 25, 30, 35, 40, 45, 50, 55, 60, 65, 70, 75, 80, 90, 100, or 110 g/liter.

The host cell may further express a nucleic acid encoding a homologous or heterologous amylase, i.e., an amylase that is not the same species as the host cell, or one or more other enzymes. The amylase may be a variant amylase. Additionally, the host may express one or more accessory enzymes, proteins, peptides. These may benefit liquefaction, saccharification, fermentation, SSF, etc. processes. Furthermore, the host cell may produce biochemicals in addition to enzymes used to digest the carbon feedstock(s). Such host cells may be useful for fermentation or simultaneous saccharification and fermentation processes to reduce or eliminate the need to add enzymes.

3.1. Vectors

A DNA construct comprising a nucleic acid encoding an AfGA or variant thereof can be constructed to be expressed in a host cell. Representative nucleic acids that encode AfGA1 include SEQ ID NO: 8. Representative nucleic acids that encode AfGA2 include SEQ ID NO: 14. Because of the well-known degeneracy in the genetic code, variant polynucleotides that encode an identical amino acid sequence can be designed and made with routine skill. It is also well-known in the art to optimize codon use for a particular host cell. Nucleic acids encoding an AfGA or variant thereof can be incorporated into a vector. Vectors can be transferred to a host cell using well-known transformation techniques, such as those disclosed below.

The vector may be any vector that can be transformed into and replicated within a host cell. For example, a vector comprising a nucleic acid encoding an AfGA or variant thereof can be transformed and replicated in a bacterial host cell as a means of propagating and amplifying the vector. The vector also may be transformed into an expression host, so that the encoding nucleic acids can be expressed as a functional AfGA or variant thereof. Host cells that serve as expression hosts can include filamentous fungi, for example. The Fungal Genetics Stock Center (FGSC) Catalogue of Strains lists suitable vectors for expression in fungal host cells. See FGSC, Catalogue of Strains, University of Missouri, at www.fgsc.net (last modified Jan. 17, 2007). Representative vectors include pJG222 (Trex3gM-AfGA1) (FIG. 2) and pJG313 (Trex3gM-AfGA2) (FIG. 10), each of which comprises a pTrex3gM expression vector (U.S. Published Application No. 2011/0136197 A1), and allows expression a nucleic acid encoding AfGA under the control of the cbh1 promoter in a fungal host. Both pJG222 and pJG313 can be modified with routine skill to comprise and express a nucleic acid encoding an AfGA variant.

A nucleic acid encoding an AfGA or a variant thereof can be operably linked to a suitable promoter, which allows transcription in the host cell. The promoter may be any DNA sequence that shows transcriptional activity in the host cell of choice and may be derived from genes encoding proteins either homologous or heterologous to the host cell. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an AfGA or variant thereof is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. The pJG222 vector depicted in FIG. 2, for example, contains a cbh1 promoter operably linked to AfGA1. The pJG313 vector depicted in FIG. 10, contains a cbh1 promoter operably linked to AfGA2. cbh1 is an endogenous, inducible promoter from *T. reesei*. See Liu et al. (2008) "Improved heterologous gene expression in *Trichoderma reesei* by cellobiohydrolase I gene (cbh1) promoter optimization," *Acta Biochim. Biophys. Sin* (*Shanghai*) 40(2): 158-65.

The coding sequence can be operably linked to a signal sequence. The DNA encoding the signal sequence may be the DNA sequence naturally associated with the AfGA gene to be expressed. For example, the DNA may encode the AfGA1 and AfGA2 signal sequence of SEQ ID NO: 11 operably linked to a nucleic acid encoding an AfGA or a variant thereof. The DNA encodes a signal sequence from a species other than *A. fumigatus*. A signal sequence and a promoter sequence comprising a DNA construct or vector can be introduced into a fungal host cell and can be derived from the same source. For example, the signal sequence is the cbh1 signal sequence that is operably linked to a cbh1 promoter.

An expression vector may also comprise a suitable transcription terminator and, in eukaryotes, polyadenylation sequences operably linked to the DNA sequence encoding an AfGA or variant thereof. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD, and sC, a marker giving rise to hygromycin resistance, or the selection may be accomplished by co-transformation, such as known in the art. See e.g., International PCT Application WO 91/17243.

Intracellular expression may be advantageous in some respects, e.g., when using certain bacteria or fungi as host cells to produce large amounts of an AfGA or variant thereof for subsequent purification. Extracellular secretion of the AfGA or variant thereof into the culture medium can also be used to make a cultured cell material comprising the isolated AfGA or variant thereof.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the AfGA or variant thereof to a host cell organelle such as a peroxisome, or to a particular host cell compartment. Such a targeting sequence includes but is not limited to the sequence serine-lysine-leucine (SKL), which is a known peroxisome target signal. For expression under the direction of control sequences, the nucleic acid sequence of the AfGA or variant thereof is operably linked to the control sequences in proper manner with respect to expression.

The procedures used to ligate the DNA construct encoding an AfGA or variant thereof, the promoter, terminator and other elements, respectively, and to insert them into suitable vectors containing the information necessary for replication, are well known to persons skilled in the art (see, e.g., Sambrook et al., MOLECULAR CLONING: A LABORATORY MANUAL, $2^{nd}$ ed., Cold Spring Harbor, 1989, and 3rd ed., 2001).

3.2. Transformation and Culture of Host Cells

A *Trichoderma reesei* host cell, comprising either a DNA construct or an expression vector, is advantageously used as a host cell in the recombinant production of an AfGATR or variant thereof. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

It is advantageous to delete genes from expression hosts, where the gene deficiency can be cured by the transformed expression vector. Known methods may be used to obtain a fungal host cell having one or more inactivated genes. Gene inactivation may be accomplished by complete or partial deletion, by insertional inactivation or by any other means that renders a gene nonfunctional for its intended purpose, such that the gene is prevented from expression of a functional protein. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding an AfGA or variant thereof is stably integrated into a host cell chromosome. Transformants are then selected and purified by known techniques.

The preparation of *Trichoderma* sp. for transformation, for example, may involve the preparation of protoplasts from fungal mycelia. See Campbell et al. (1989) *Curr. Genet.* 16: 53-56. The mycelia can be obtained from germinated vegetative spores. The mycelia are treated with an enzyme that digests the cell wall, resulting in protoplasts. The protoplasts are protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M, e.g., a 1.2 M solution of sorbitol can be used in the suspension medium.

Uptake of DNA into the host *Trichoderma* sp. strain depends upon the calcium ion concentration. Generally, between about 10-50 mM $CaCl_2$ is used in an uptake solution. Additional suitable compounds include a buffering system, such as TE buffer (10 mM Tris, pH 7.4; 1 mM EDTA) or 10 mM MOPS, pH 6.0 and polyethylene glycol. The polyethylene glycol is believed to fuse the cell membranes, thus permitting the contents of the medium to be delivered into the cytoplasm of the *Trichoderma* sp. strain. This fusion frequently leaves multiple copies of the plasmid DNA integrated into the host chromosome.

Usually transformation of *Trichoderma* sp. uses protoplasts or cells that have been subjected to a permeability treatment, typically at a density of $10^5$ to $10^7$/mL, particularly $2\times10^6$/mL. A volume of 100 µL of these protoplasts or cells in an appropriate solution (e.g., 1.2 M sorbitol and 50 mM $CaCl_2$) may be mixed with the desired DNA. Generally, a high concentration of PEG is added to the uptake solution. From 0.1 to 1 volume of 25% PEG 4000 can be added to the protoplast suspension; however, it is useful to add about 0.25 volumes to the protoplast suspension. Additives, such as dimethyl sulfoxide, heparin, spermidine, potassium chloride and the like, may also be added to the uptake solution to facilitate transformation. Similar procedures are available for other fungal host cells. See, e.g., U.S. Pat. No. 6,022,725.

3.3. Expression

A method of producing an AfGATR or variant thereof may comprise cultivating a *Trichoderma reesei* host cell as described above under conditions conducive to the production of the enzyme and recovering the enzyme from the cells and/or culture medium. *Trichoderma reesei* host cells express AfGATRs at higher, or at least comparable, levels to natively expressed AfGA *Aspergillus fumigatus*.

The medium used to cultivate the cells may be any conventional medium suitable for growing the host cell in question and obtaining expression of an AfGATR or variant thereof. Suitable media and media components are available from commercial suppliers or may be prepared according to published recipes (e.g., as described in catalogues of the American Type Culture Collection).

An enzyme secreted from the host cells can be used in a whole broth preparation. In the present methods, the preparation of a spent whole fermentation broth of a recombinant microorganism can be achieved using any cultivation method known in the art resulting in the expression of a glucoamylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the glucoamylase to be expressed or isolated. The term "spent whole fermentation broth" is defined herein as the unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

The polynucleotide encoding AfGA or a variant thereof in a vector can be operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of the AfGATR or variant thereof. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sepharose. Polypeptides can also be produced recombinantly in an in vitro cell-free system, such as the TNT™ (Promega) rabbit reticulocyte system.

An expression host also can be cultured in the appropriate medium for the host, under aerobic conditions. Shaking or a combination of agitation and aeration can be provided, with production occurring at the appropriate temperature for that host, e.g., from about 25° C. to about 78° C. (e.g., 30° C. to 45° C.), depending on the needs of the host and production of the desired AfGATR or variant thereof. Culturing can occur from about 12 to about 100 hours or greater (and any hour value there between, e.g., from 24 to 72 hours). Typically, the culture broth is at a pH of about 4.0 to about 8.0, again depending on the culture conditions needed for the host relative to production of an AfGATR or variant thereof.

3.4. Identification of AfGATR Activity

To evaluate the expression of an AfGATR or variant thereof in a host cell, assays can measure the expressed protein, corresponding mRNA, or glucoamylase activity. For example, suitable assays include Northern blotting, reverse transcriptase polymerase chain reaction, and in situ hybridization, using an appropriately labeled hybridizing probe. Suitable assays also include measuring AfGATR activity in a sample, for example, by assays directly measuring reducing sugars such as glucose in the culture media. For example, glucose concentration may be determined using glucose reagent kit No. 15-UV (Sigma Chemical Co.) or an instrument, such as Technicon Autoanalyzer. Glucoamylase activity also may be measured by any known method, such as the PAHBAH or ABTS assays, described below.

3.5. Methods for Purifying an AfGATR and Variants Thereof

Fermentation, separation, and concentration techniques are well known in the art and conventional methods can be used in order to prepare a concentrated AfGATR or variant glucoamylase polypeptide-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate an AfGATR or variant glucoamylase polypeptide-containing solution in order to optimize recovery. Use of unconcentrated solutions can require increased incubation time in order to collect the purified enzyme precipitate.

The enzyme containing solution is concentrated using conventional concentration techniques until the desired enzyme level is obtained. Concentration of the enzyme containing solution may be achieved by any of the techniques discussed herein. Exemplary methods of purification include but are not limited to rotary vacuum filtration and/or ultrafiltration.

The enzyme solution is concentrated into a concentrated enzyme solution until the enzyme activity of the concentrated AfGATR or variant glucoamylase polypeptide-containing solution is at a desired level.

Concentration may be performed using, e.g., a precipitation agent, such as a metal halide precipitation agent. Metal halide precipitation agents include but are not limited to alkali metal chlorides, alkali metal bromides, and blends of two or more of these metal halides. Exemplary metal halides include sodium chloride, potassium chloride, sodium bromide, potassium bromide, and blends of two or more of these metal halides. The metal halide precipitation agent, sodium chloride, can also be used as a preservative.

The metal halide precipitation agent is used in an amount effective to precipitate the AfGATR or variant thereof. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific AfGATR or variant glucoamylase polypeptide and on its concentration in the concentrated enzyme solution.

Another alternative way to precipitate the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, AfGATR or variant glucoamylase polypeptide concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated enzyme solution and usually at least about 0.02% w/v. Generally, no more than about 0.3% w/v of organic compound precipitation agent is added to the concentrated enzyme solution and usually no more than about 0.2% w/v.

The concentrated polypeptide solution, containing the metal halide precipitation agent, and the organic compound precipitation agent, can be adjusted to a pH, which will, of necessity, depend on the enzyme to be purified. Generally, the pH is adjusted at a level near the isoelectric point of the glucoamylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent (s) and its (their) concentration. Generally, the time effective to precipitate the enzyme is between about 1 to about 30 hours; usually it does not exceed about 25 hours. In the presence of the organic compound precipitation agent, the time of incubation can still be reduced to less than about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme can be then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like.

Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, an AfGATR or variant glucoamylase polypeptide accumulates in the culture broth. For the isolation and purification of the desired AfGATR or variant glucoamylase, the culture broth can be centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in Sumitani et al. (2000) "New type of starch-binding domain: the direct repeat motif in the C-terminal region of *Bacillus* sp. 195 glucoamylase contributes to starch binding and raw starch degrading," *Biochem. J.* 350: 477-484, and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 min. and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$), and eluted at a linear flow rate of 7 mL/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$) and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$). The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$), at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See Sumitani et al. (2000) *Biochem. J.* 350: 477-484, for general discussion of the method and variations thereon.

For production scale recovery, an AfGATR or variant glucoamylase polypeptide can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Compositions and Uses of AfGATR and Variants Thereof

AfGATR and its variants are useful for a variety of industrial applications. For example, AfGATR and its variants are useful in a starch conversion process, particularly in a saccharification process of a starch that has undergone liquefaction. The desired end-product may be any product that may be produced by the enzymatic conversion of the starch substrate. For example, the desired product may be a syrup rich in glucose, which can be used in other processes, such as the preparation of HFCS, or which can be converted into a number of other useful products, such as ascorbic acid intermediates (e.g., gluconate; 2-keto-L-gulonic acid; 5-keto-gluconate; and 2,5-diketogluconate); 1,3-propanediol; aromatic amino acids (e.g., tyrosine, phenylalanine and tryptophan); organic acids (e.g., lactate, pyruvate, succinate, isocitrate, and oxaloacetate); amino acids (e.g., serine and glycine); antibiotics; antimicrobials; enzymes; vitamins; and hormones.

The starch conversion process may be a precursor to, or simultaneous with, a fermentation process designed to produce alcohol for fuel or drinking (i.e., potable alcohol). One skilled in the art is aware of various fermentation conditions that may be used in the production of these end-products. AfGATR and variants thereof also are useful in compositions and methods of food preparation. These various uses of AfGATR and its variants are described in more detail below.

4.1. Preparation of Starch Substrates

Those of general skill in the art are well aware of available methods that may be used to prepare starch substrates for use in the processes disclosed herein. For example, a useful starch substrate may be obtained from tubers, roots, stems, legumes, cereals or whole grain. More specifically, the granular starch may be obtained from corn, cobs, wheat, barley, rye, triticale, milo, sago, millet, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains 70-72% starch. Specifically contemplated starch substrates are corn starch and wheat starch. The starch from a grain may be ground or whole and includes corn solids, such as kernels, bran and/or cobs. The starch may be highly refined raw starch or feedstock from starch refinery processes. Various starches also are commercially available. For example, corn starch is available from Cerestar, Sigma, and Katayama Chemical Industry Co. (Japan); wheat starch is available from Sigma; sweet potato starch is available from Wako Pure Chemical Industry Co. (Japan); and potato starch is available from Nakaari Chemical Pharmaceutical Co. (Japan).

The starch substrate can be a crude starch from milled whole grain, which contains non-starch fractions, e.g., germ residues and fibers. Milling may comprise either wet milling or dry milling or grinding. In wet milling, whole grain is soaked in water or dilute acid to separate the grain into its component parts, e.g., starch, protein, germ, oil, kernel fibers. Wet milling efficiently separates the germ and meal (i.e., starch granules and protein) and is especially suitable for production of syrups. In dry milling or grinding, whole kernels are ground into a fine powder, and often processed without fractionating the grain into its component parts. In some cases, oils from the kernels are recovered. Dry ground grain generally will comprise significant amounts of non-starch carbohydrate compounds, in addition to starch. Dry grinding of the starch substrate can be used for production of ethanol and other biochemicals. The starch to be processed may be a highly refined starch quality, for example, at least 90%, at least 95%, at least 97%, or at least 99.5% pure.

4.2. Gelatinization and Liquefaction of Starch

As used herein, the term "liquefaction" or "liquefy" means a process by which starch is converted to less viscous and shorter chain dextrins. Generally, this process involves gelatinization of starch simultaneously with or followed by the addition of an α-amylase, although additional liquefaction-inducing enzymes optionally may be added. In some embodiments, the starch substrate prepared as described above is slurried with water. The starch slurry may contain starch as a weight percent of dry solids of about 10-55%, about 20-45%, about 30-45%, about 30-40%, or about 30-35%. α-Amylase (EC 3.2.1.1) may be added to the slurry, with a metering pump, for example. The α-amylase typically used for this application is a thermally stable, bacterial α-amylase, such as a *Geobacillus stearothermophilus* α-amylase. The α-amylase is usually supplied, for example, at about 1500 units per kg dry matter of starch. To optimize α-amylase stability and activity, the pH of the slurry typically is adjusted to about pH 5.5-6.5 and about 1 mM of calcium (about 40 ppm free calcium ions) typically is added. *Geobacillus stearothermophilus* variants or other α-amylases may require different conditions. Bacterial α-amylase remaining in the slurry following liquefaction may be deactivated via a number of methods, including lowering the pH in a subsequent reaction step or by removing calcium from the slurry in cases where the enzyme is dependent upon calcium.

The slurry of starch plus the α-amylases may be pumped continuously through a jet cooker, which is steam heated to 105° C. Gelatinization occurs rapidly under these conditions, and the enzymatic activity, combined with the shear forces, begins the hydrolysis of the starch substrate. The residence time in the jet cooker is brief. The partly gelatinized starch may be passed into a series of holding tubes maintained at 105-110° C. and held for 5-8 min. to complete the gelatinization process ("primary liquefaction"). Hydrolysis to the required DE is completed in holding tanks at 85-95° C. or higher temperatures for about 1 to 2 hours ("secondary liquefaction"). These tanks may contain baffles to discourage back mixing. As used herein, the term "minutes of secondary liquefaction" refers to the time that has elapsed from the start of secondary liquefaction to the time that the Dextrose Equivalent (DE) is measured. The slurry is then allowed to cool to room temperature. This cooling step can be 30 minutes to 180 minutes, e.g. 90 minutes to 120 minutes.

The liquefied starch resulting from the process above typically contains about 98% oligosaccharides and about 2% maltose and 0.3% D-glucose. The liquefied starch typically is in the form of a slurry having a dry solids content (w/w) of about 10-50%; about 10-45%; about 15-40%; about 20-40%; about 25-40%; or about 25-35%.

AkAA, AtAmyl, AfAmyl, and AcAmyl and variants thereof can be used in a process of liquefaction instead of bacterial α-amylases. Liquefaction with these α-amylase and variants thereof advantageously can be conducted at low pH, eliminating the requirement to adjust the pH to about pH 5.5-6.5. Theses α-amylases variants thereof can be used for liquefaction at a pH range of 2 to 7, e.g., pH 3.0-7.5, pH 4.0-6.0, or pH 4.5-5.8. They can maintain liquefying activity at a temperature range of about 85° C.-95° C., e.g., 85° C., 90° C., or 95° C. For example, liquefaction can be conducted with 800 μg AcAmyl or a variant thereof in a solution of 25% DS corn starch for 10 min at pH 5.8 and 85° C., or pH 4.5 and 95° C., for example. Liquefying activity can be assayed using any of a number of known viscosity assays in the art.

4.3. Saccharification

The liquefied starch can be saccharified into a syrup rich in lower DP, especially DP1 saccharides, using the AfGATR and variants thereof, optionally in the presence of another enzyme(s). The exact composition of the products of saccharification depends on the combination of enzymes used, as well as the type of granular starch processed. Advantageously, the syrup obtainable using the provided AfGATR and variants thereof may contain a weight percent of DP1 of the total oligosaccharides in the saccharified starch exceeding about 65%, e.g., 70%, 80%, 85%, 90%, 95%, or 96%.

Whereas liquefaction is generally run as a continuous process, saccharification is often conducted as a batch process. Saccharification typically is most effective at temperatures of about 55°–75° C. and a pH of about 4.0-6.7, e.g., pH 5.0, necessitating cooling and adjusting the pH of the liquefied starch. Saccharification may be performed, for example, at a temperature between about 40° C., about 55° C., or about 65° C. to about 70° C., about 75° C., or about 80° C. Saccharification is normally conducted in stirred tanks, which may take several hours to fill or empty. Enzymes typically are added either at a fixed ratio to dried solids as the tanks are filled or added as a single dose at the commencement of the filling stage. A saccharification reaction to make a syrup typically is run over about 24-72 hours, for example, 24-48 hours. When a maximum or desired DE has been attained, the reaction is stopped by heating to 85° C. for 5 min., for example. Further incubation will result in a lower DE, eventually to about 90 DE, as accumulated glucose re-polymerizes to isomaltose and/or other reversion products via an enzymatic reversion reaction and/or with the approach of thermodynamic equilibrium. When using an AfGATR polypeptide or variants thereof, saccharification optimally is conducted at a temperature range of about 40° C. to about 80° C., e.g., about 55° C. to about 75° C. or about 65° C. to about 70° C. The saccharifying may be conducted over a pH range of about pH 3.0 to about pH 7.5, e.g., pH 3.5-pH 7.0, pH 4.0-pH 6.7, or pH 5.0.

AfGATR or a variant thereof may be added to the slurry in the form of a composition. AfGATR or a variant thereof can be added to a slurry of a granular starch substrate in an amount of about 0.6-10 ppm ds, e.g., 2 ppm ds. The AfGATR or variant thereof can be added as a whole broth, clarified, partially purified, or purified enzyme. The specific activity of the purified AfGA1TR or variant thereof may be about 187.7 U/mg, for example, measured with the ABTS assay. The specific activity of the purified AfGA2TR or variant thereof may be about 213.7 U/mg, for example, measured with the ABTS assay. The AfGATR or variant thereof also can be added as a whole broth product.

AfGATR or a variant thereof may be added to the slurry as an isolated enzyme solution. For example, AfGATR or a variant thereof can be added in the form of a cultured cell material produced by host cells expressing the AfGATR or variant thereof. AfGATR or a variant thereof also may be secreted by a host cell into the reaction medium during the fermentation or SSF process, such that the enzyme is provided continuously into the reaction. The host cell producing and secreting the AfGATR or a variant may also express an additional enzyme, such as a glucoamylase. For example, U.S. Pat. No. 5,422,267 discloses the use of a glucoamylase in yeast for production of alcoholic beverages. For example, a host cell, e.g., *Trichoderma reesei* may be engineered to co-express AfGATR or a variant thereof and an α-amylase, including, but not limited to AkAA, AcAmyl, native *Trichoderma reesei* α-amylase, or variants thereof during saccharification. The host cell can be genetically modified so as not to express its endogenous glucoamylase and/or other enzymes, proteins or other materials. The host cell can be engineered to express a broad spectrum of various saccharolytic enzymes. For example, the recombinant yeast host cell can comprise nucleic acids encoding a glucoamylase, an alpha-glucosidase, an enzyme that utilizes pentose sugar, an α-amylase, a pullulanase, an isoamylase, and/or an isopullulanase. See, e.g., WO 2011/153516 A2.

4.4. Isomerization

The soluble starch hydrolysate produced by treatment with AfGATR or variants thereof can be converted into high fructose starch-based syrup (HFSS), such as high fructose corn syrup (HFCS). This conversion can be achieved using a glucose isomerase, particularly a glucose isomerase immobilized on a solid support. The pH is increased to about 6.0 to about 8.0, e.g., pH 7.5, and Ca' is removed by ion exchange. Suitable isomerases include Sweetzyme®, IT (Novozymes A/S); G-zyme® IMGI, and G-zyme® G993, Ketomax®, G-zyme® G993, G-zyme® G993 liquid, and GenSweet® IGI. Following isomerization, the mixture typically contains about 40-45% fructose, e.g., 42% fructose.

4.5. Fermentation

The soluble starch hydrolysate, particularly a glucose rich syrup, can be fermented by contacting the starch hydrolysate with a fermenting organism typically at a temperature around 32° C., such as from 30° C. to 35° C. EOF products include metabolites, such as citric acid, lactic acid, succinic acid, monosodium glutamate, gluconic acid, sodium gluconate, calcium gluconate, potassium gluconate, itaconic acid and other carboxylic acids, glucono delta-lactone, sodium erythorbate, lysine and other amino acids, omega 3 fatty acid, butanol, isoprene, 1,3-propanediol and other biomaterials.

Ethanologenic microorganisms include yeast, such as *Saccharomyces cerevisiae* and bacteria, e.g., *Zymomonas moblis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27(7): 1049-56. Commercial sources of yeast include ETHANOL RED® (LeSaffre); Thermosacc® (Lallemand); RED STAR® (Red Star); FERMIOL® (DSM Specialties); and SUPERSTART® (Alltech). Microorganisms that produce other metabolites, such as citric acid and lactic acid, by fermentation are also known in the art. See, e.g., Papagianni (2007) "Advances in citric acid fermentation by *Aspergillus niger*: biochemical aspects, membrane transport and modeling," *Biotechnol. Adv.* 25(3): 244-63; John et al. (2009) "Direct lactic acid fermentation: focus on simultaneous saccharification and lactic acid production," *Biotechnol. Adv.* 27(2): 145-52.

The saccharification and fermentation processes may be carried out as an SSF process. Fermentation may comprise subsequent purification and recovery of ethanol, for example. During the fermentation, the ethanol content of the broth or "beer" may reach about 8-18% v/v, e.g., 14-15% v/v. The broth may be distilled to produce enriched, e.g., 96% pure, solutions of ethanol. Further, $CO_2$ generated by fermentation may be collected with a $CO_2$ scrubber, compressed, and marketed for other uses, e.g., carbonating beverage or dry ice production. Solid waste from the fermentation process may be used as protein-rich products, e.g., livestock feed.

As mentioned above, an SSF process can be conducted with fungal cells, such as *Trichoderma reesei*, that express and secrete AfGATR or its variants continuously throughout SSF. The fungal cells expressing AfGATR or its variants also can be the fermenting microorganism, e.g., an ethanologenic microorganism. Ethanol production thus can be carried out using a fungal cell that expresses sufficient AfGATR or its variants so that less or no enzyme has to be added exogenously. The fungal host cell can be from an appropriately engineered fungal strain. Fungal host cells that express and secrete other enzymes, in addition to AfGATR or its variants, also can be used. Such cells may express α-amylase and/or a pullulanase, phytase, alpha-glucosidase, isoamylase, beta-amylase cellulase, xylanase, other hemicellulases, protease, beta-glucosidase, pectinase, esterase, redox enzymes, transferase, a glucoamylase other than AfGATR or other enzyme.

A variation on this process is a "fed-batch fermentation" system, where the substrate is added in increments as the fermentation progresses. Fed-batch systems are useful when catabolite repression may inhibit the metabolism of the cells and where it is desirable to have limited amounts of substrate in the medium. The actual substrate concentration in fed-batch systems is estimated by the changes of measurable factors such as pH, dissolved oxygen and the partial pressure of waste gases, such as $CO_2$. Batch and fed-batch fermentations are common and well known in the art.

Continuous fermentation is an open system where a defined fermentation medium is added continuously to a bioreactor, and an equal amount of conditioned medium is removed simultaneously for processing. Continuous fermentation generally maintains the cultures at a constant high density where cells are primarily in log phase growth. Continuous fermentation permits modulation of cell growth and/or product concentration. For example, a limiting nutrient such as the carbon source or nitrogen source is maintained at a fixed rate and all other parameters are allowed to moderate. Because growth is maintained at a steady state, cell loss due to medium being drawn off should be balanced against the cell growth rate in the fermentation. Methods of optimizing continuous fermentation processes and maximizing the rate of product formation are well known in the art of industrial microbiology.

4.6. Compositions Comprising AfGATR or Variants Thereof

AfGATR or variants thereof may be combined with an α-amylase (EC 3.2.1.1). In some embodiments, the α-amylase is an acid stable alpha amylase which when added in an effective amount has activity in the pH range of 3.0 to 7.0 and preferably from 3.5 to 6.5. Alpha amylases may be a fungal α-amylase or a bacterial α-amylase. Further, the α-amylase may be a wild-type α-amylase or a variant thereof.

Preferred examples of fungal alpha amylases include those obtained from filamentous fungal strains including but not limited to strains of *Aspergillus* (e.g., *A. niger*, *A. kawachii*, and *A. oryzae*); *Trichoderma* sp., *Rhizopus* sp., *Mucor* sp., and *Penicillium* sp. *Lactobacilli* sp. and *Streptomuces* sp. The acid stable α-amylase may be derived from a bacterial strain. Preferred bacterial strains include *Bacillus* sp., such as *B. licheniformis*, *B. stearothermophilus*, *B. amyloliquefaciens*, *B. subtilis*, *B. lentus*, and *B. coagulans*. Particularly preferred are *B. licheniformis*, *B. stearothermophilus*, and *B. amyloliquefaciens*. One of the bacterial alpha amylases used in the compositions and processes of the invention may include one of the α-amylases described in U.S. Pat. Nos. 5,093,257; 5,763,385; 5,824,532; 5,958,739; 6,008,026; 6,093,563; 6,187,576; 6,361,809; 6,867,031; U.S. Publication No. 2006/0014265; and International PCT Nos. WO 96/23874, WO 96/39528; WO 97/141213, WO 99/19467; and WO 05/001064.

Exemplary α-amylases include is AkAA or AcAmyl and variants thereof that possess superior specific activity and thermal stability. Suitable variants of AkAA include those with α-amylase activity and at least 80%, 90%, 95%, 98% or at least 99% sequence identity to wild-type AkAA. Suitable variants of AcAmyl include those with α-amylase activity and at least 80%, at least 90%, or at least 95% sequence identity to wild-type AcAmyl. AfGATR and its variants advantageously increase the yield of glucose produced in a saccharification process catalyzed by AnGA or Tr-GA.

Commercially available alpha amylases contemplated for use in the compositions and method include: SPEZYME™ AA; SPEZYME™ FRED; SPEZYME™ XTRA; GZYME™ 997; and CLARASE™ L (Genencor International Inc.); TERMAMYL™ 120-L, LC and SC and SUPRA (Novozymes Biotech); LIQUOZYME™ X and SAN TMSUPER (Novozymes A/S) and Fuelzyme™ LF (*Diversa*). In some embodiments, the alpha amylase will include an alpha amylase derived from *Bacillus stearothermophilus* such as SPEZYME TMAA, SPEZYME™ FRED or SPEZYME™ XTRA. In some embodiments, the enzyme compositions will include BP-WT, SPEZYME™ XTRA and optionally SPEZYME™ FRED. In other embodiments, the compositions will include BP-17, SPEZYME™ XTRA and optionally SPEZYME™ FRED.

Other suitable enzymes that can be used with AfGATR or its variants include a glucoamylase that is not AfGATR, phytase, protease, pullulanase, β-amylase, isoamylase, α-amylase, alpha-glucosidase, cellulase, xylanase, other hemicellulases, beta-glucosidase, transferase, pectinase, lipase, cutinase, esterase, redox enzymes, or a combination thereof.

For example, a debranching enzyme, such as a pullulanase (EC 3.2.1.41), e.g., Promozyme®, may be added in effective amounts well known to the person skilled in the art. Pullulanase typically is added at 100 U/kg ds. Pullulanases are generally secreted by a *Bacillus* species. Exemplary pullanases are described for *Bacillus deramificans* (U.S. Pat. No. 5,817,498; 1998), *Bacillus acidopullulyticus* (European Patent #0 063 909 and *Bacillus naganoensis* (U.S. Pat. No. 5,055,403). Enzymes having pullulanase activity used commercially are produced for examples, from *Bacillus* species (trade name OPTIMAX™ L-1000 from Danisco-Genencor and Promozyme™ from Novozymes).

*Bacillus megaterium* amylase/transferase (BMA): *Bacillus megaterium* amylase has the ability to convert the branched saccharides to a form that is easily hydrolysed by glucoamylase. (Habeda R. E., Styrlund C. R and Teague, W. M.; 1988 Starch/Starke, 40, 33-36) The enzyme exhibits maximum activity at pH 5.5 and temperature at 75 C. (David, M. H., Gunther H and Vilvoorde, H. R.; 1987, Starch/Starke, 39 436-440) The enzyme has been cloned, expressed in a genetically engineered *Bacillus subtilis* and produced on a commercial scale (Brumm, P. J., Habeda R. E, and Teague W. M., 1991 Starch/Starke, 43 315-329). The enzyme is sold under a trade name MEGADEX™ for enhancing the glucose yield during the saccharification of enzyme liquefied starch by *Aspergillus niger* glucoamylase.

An isoamylase (EC 3.2.1.68), may also be added in effective amounts well known to the person skilled in the art. A pullulanase (EC 3.2.1.41), e.g., Promozyme®, is also suitable. Pullulanase typically is added at 100 U/kg ds. Further suitable enzymes include proteases, such as fungal and bacterial proteases. Fungal proteases include those obtained from *Aspergillus*, such as *A. niger, A. awamori, A. oryzae; Mucor* (e.g., *M. miehei*); *Rhizopus*; and *Trichoderma*.

β-Amylases (EC 3.2.1.2) are exo-acting maltogenic amylases, which catalyze the hydrolysis of 1,4-α-glucosidic linkages into amylopectin and related glucose polymers, thereby releasing maltose. β-Amylases have been isolated from various plants and microorganisms. See Fogarty et al. (1979) in PROGRESS IN INDUSTRIAL MICROBIOLOGY, Vol. 15, pp. 112-115. These β-Amylases have optimum temperatures in the range from 40° C. to 65° C. and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Danisco US Inc.); and Novozym™ WBA (Novozymes A/S).

5. Compositions and Methods for Baking and Food Preparation

The present invention also relates to a "food composition," including but not limited to a food product, animal feed and/or food/feed additives, comprising an AfGATR or variant thereof, and methods for preparing such a food composition comprising mixing AfGATR or variant thereof with one or more food ingredients, or uses thereof.

The AfGATR or variant thereof can be used in the preparation of a food composition, wherein the food composition is baked subsequent to the addition of the polypeptide. As used herein the term "baking composition" means any composition and/or additive prepared in the process of providing a baked food product, including but not limited to bakers flour, a dough, a baking additive and/or a baked product. The food composition or additive may be liquid or solid.

As used herein, the term "flour" means milled or ground cereal grain. The term "flour" also may mean Sago or tuber products that have been ground or mashed. In some embodiments, flour may also contain components in addition to the milled or mashed cereal or plant matter. An example of an additional component, although not intended to be limiting, is a leavening agent. Cereal grains include wheat, oat, rye, and barley. Tuber products include tapioca flour, cassava flour, and custard powder. The term "flour" also includes ground corn flour, maize-meal, rice flour, whole-meal flour, self-rising flour, tapioca flour, cassava flour, ground rice, enriched flower, and custard powder.

For the commercial and home use of flour for baking and food production, it is important to maintain an appropriate level of glucoamylase activity in the flour. A level of activity that is too high may result in a product that is sticky and/or doughy and therefore unmarketable. Flour with insufficient glucoamylase activity may not contain enough sugar for proper yeast function, resulting in dry, crumbly bread, or baked products. Accordingly, an AfGATR or variant thereof, by itself or in combination with an α-amylase(s), may be added to the flour to augment the level of endogenous glucoamylase activity in flour.

An amylase can be added alone or in a combination with other amylases to prevent or retard staling, i.e., crumb firming of baked products. The amount of anti-staling amylase will typically be in the range of 0.01-10 mg of enzyme protein per kg of flour, e.g., 0.5 mg/kg ds. Additional anti-staling amylases that can be used in combination with an AfGATR or variant thereof include an endo-amylase, e.g., a bacterial endo-amylase from *Bacillus*. The additional amylase can be another maltogenic α-amylase (EC 3.2.1.133), e.g., from *Bacillus*. Novamyl® is an exemplary maltogenic α-amylase from *B. stearothermophilus* strain NCIB 11837 and is described, for example, in Christophersen et al. (1997) *Starch* 50: 39-45. Other examples of anti-staling endo-amylases include bacterial α-amylases derived from *Bacillus*, such as *B. licheniformis* or *B. amyloliquefaciens*. The anti-staling amylase may be an exo-amylase, such as β-amylase, e.g., from plant sources, such as soybean, or from microbial sources, such as *Bacillus*.

The baking composition comprising an AfGATR or variant thereof further can comprise a phospholipase or enzyme with phospholipase activity. An enzyme with phospholipase activity has an activity that can be measured in Lipase Units (LU). The phospholipase may have $A_1$ or $A_2$ activity to remove fatty acid from the phospholipids, forming a lysophospholipid. It may or may not have lipase activity, i.e., activity on triglyceride substrates. The phospholipase typically has a temperature optimum in the range of 30-90° C., e.g., 30-70° C. The added phospholipases can be of animal origin, for example, from pancreas, e.g., bovine or porcine pancreas, snake venom, or bee venom. Alternatively, the phospholipase may be of microbial origin, e.g., from filamentous fungi, yeast or bacteria, for example.

The phospholipase is added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. That is, phospholipase activity generally will be in the range of 20-1000 LU/kg of flour, where a Lipase Unit is defined as the amount of enzyme required to release 1 µmol butyric acid per minute at 30° C., pH 7.0, with gum arabic as emulsifier and tributyrin as substrate.

Compositions of dough generally comprise wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen, or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of *S. cerevisiae*.

The dough may also comprise other conventional dough ingredients, e.g., proteins, such as milk powder, gluten, and soy; eggs (e.g., whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate, or calcium sulfate. The dough further may comprise fat, e.g., triglyceride, such as granulated fat or shortening. The dough further may comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. For example, the dough can be made without addition of emulsifiers.

The dough product may be any processed dough product, including fried, deep fried, roasted, baked, steamed and boiled doughs, such as steamed bread and rice cakes. In one embodiment, the food product is a bakery product. Typical bakery (baked) products include bread—such as loaves, rolls, buns, bagels, pizza bases etc. pastry, pretzels, tortillas, cakes, cookies, biscuits, crackers etc.

Optionally, an additional enzyme may be used together with the anti-staling amylase and the phospholipase. The additional enzyme may be a second amylase, such as an amyloglucosidase, a β-amylase, a cyclodextrin glucanotransferase, or the additional enzyme may be a peptidase, in particular an exopeptidase, a transglutaminase, a lipase, a cellulase, a xylanase, a protease, a protein disulfide isomerase, e.g., a protein disulfide isomerase as disclosed in WO 95/00636, for example, a glycosyltransferase, a branching enzyme (1,4-α-glucan branching enzyme), a 4-α-glucanotransferase (dextrin glycosyltransferase) or an oxidoreductase, e.g., a peroxidase, a laccase, a glucose oxidase, a pyranose oxidase, a lipooxygenase, an L-amino acid oxidase or a carbohydrate oxidase. The additional enzyme(s) may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*. Xylanases include Pentopan® and Novozym 384®, for example, which are commercially available xylanase preparations produced from *Trichoderma reesei*. The amyloglucosidase may be an *A. niger* amyloglucosidase (such as AMG®). Other useful amylase products include Grindamyl® A 1000 or A 5000 (Grindsted Products, Denmark) and Amylase® H or Amylase® P (DSM). The glucose oxidase may be a fungal glucose oxidase, in particular an *Aspergillus niger* glucose oxidase (such as Gluzyme®). An exemplary protease is Neutrase®.

The process may be used for any kind of baked product prepared from dough, either of a soft or a crisp character, either of a white, light or dark type. Examples are bread, particularly white, whole-meal or rye bread, typically in the form of loaves or rolls, such as, but not limited to, French baguette-type bread, pita bread, tortillas, cakes, pancakes, biscuits, cookies, piecrusts, crisp bread, steamed bread, pizza and the like.

The AfGATR or variant thereof may be used in a pre-mix, comprising flour together with an anti-staling amylase, a phospholipase, and/or a phospholipid. The pre-mix may contain other dough-improving and/or bread-improving additives, e.g., any of the additives, including enzymes, mentioned above. The AfGATR or variant thereof can be a component of an enzyme preparation comprising an anti-staling amylase and a phospholipase, for use as a baking additive.

The enzyme preparation is optionally in the form of a granulate or agglomerated powder. The preparation can have a narrow particle size distribution with more than 95% (by weight) of the particles in the range from 25 to 500 µm. Granulates and agglomerated powders may be prepared by conventional methods, e.g., by spraying the AfGATR or variant thereof onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Enveloped particles, i.e., glucoamylase particles, can comprise an AfGATR or variants thereof. To prepare enveloped glucoamylase particles, the enzyme is contacted with a food grade lipid in sufficient quantity to suspend all of the glucoamylase particles. Food grade lipids, as used herein, may be any naturally organic compound that is insoluble in water but is soluble in non-polar organic solvents such as hydrocarbon or diethyl ether. Suitable food grade lipids include, but are not limited to, triglycerides either in the form of fats or oils that are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of the glucoamylase particles in such a fashion that the lipid material covers at least a portion of the surface of at least a majority, e.g., 100% of the glucoamylase particles. Thus, each glucoamylase particle is individually enveloped in a lipid. For example, all or substantially all of the glucoamylase particles are provided with a thin, continuous, enveloping film of lipid. This can be accomplished by first pouring a quantity of lipid into a container, and then slurrying the glucoamylase particles so that the lipid thoroughly wets the surface of a glucoamylase particle. After a short period of stirring, the enveloped glucoamylase particles, carrying a substantial amount of the lipids on their surfaces, are recovered. The thickness of the coating so applied to the particles of glucoamylase can be controlled by selection of the type of lipid used and by repeating the operation in order to build up a thicker film, when desired.

The storing, handling and incorporation of the loaded delivery vehicle can be accomplished by means of a packaged mix. The packaged mix can comprise the enveloped glucoamylase. However, the packaged mix may further contain additional ingredients as required by the manufacturer or baker. After the enveloped glucoamylase has been incorporated into the dough, the baker continues through the normal production process for that product.

The advantages of enveloping the glucoamylase particles are two-fold. First, the food grade lipid protects the enzyme from thermal denaturation during the baking process for those enzymes that are heat labile. Consequently, while the glucoamylase is stabilized and protected during the proving and baking stages, it is released from the protective coating in the final baked good product, where it hydrolyzes the glucosidic linkages in polyglucans. The loaded delivery vehicle also provides a sustained release of the active enzyme into the baked good. That is, following the baking process, active glucoamylase is continually released from the protective coating at a rate that counteracts, and therefore reduces the rate of, staling mechanisms.

In general, the amount of lipid applied to the glucoamylase particles can vary from a few percent of the total weight of the glucoamylase to many times that weight, depending upon the nature of the lipid, the manner in which it is applied to the glucoamylase particles, the composition of the dough mixture to be treated, and the severity of the dough-mixing operation involved.

The loaded delivery vehicle, i.e., the lipid-enveloped enzyme, is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped glucoamylase required is calculated based on the concentration of enzyme enveloped and on the proportion of glucoamylase to flour specified. A wide range of concentrations has been found to be effective, although, as has been discussed, observable improvements in anti-staling do not correspond linearly with the glucoamylase concentration, but above certain minimal levels, large increases in glucoamylase concentration produce little additional improvement. The glucoamylase concentration actually used in a particular bakery production could be much higher than the minimum necessary to provide the baker with some insurance against inadvertent under-measurement errors by the baker. The lower limit of enzyme concentration is determined by the minimum anti-staling effect the baker wishes to achieve.

A method of preparing a baked good may comprise: a) preparing lipid-coated glucoamylase particles, where substantially all of the glucoamylase particles are coated; b) mixing a dough containing flour; c) adding the lipid-coated glucoamylase to the dough before the mixing is complete and terminating the mixing before the lipid coating is removed from the α-amylase; d) proofing the dough; and e) baking the dough to provide the baked good, where the glucoamylase is inactive during the mixing, proofing and baking stages and is active in the baked good.

The enveloped glucoamylase can be added to the dough during the mix cycle, e.g., near the end of the mix cycle. The enveloped glucoamylase is added at a point in the mixing stage that allows sufficient distribution of the enveloped glucoamylase throughout the dough; however, the mixing stage is terminated before the protective coating becomes stripped from the glucoamylase particle(s). Depending on the type and volume of dough, and mixer action and speed, anywhere from one to six minutes or more might be required to mix the enveloped glucoamylase into the dough, but two to four minutes is average. Thus, several variables may determine the precise procedure. First, the quantity of enveloped glucoamylase should have a total volume sufficient to allow the enveloped glucoamylase to be spread throughout the dough mix. If the preparation of enveloped glucoamylase is highly concentrated, additional oil may need to be added to the pre-mix before the enveloped glucoamylase is added to the dough. Recipes and production processes may require specific modifications; however, good results generally can be achieved when 25% of the oil specified in a bread dough formula is held out of the dough and is used as a carrier for a concentrated enveloped glucoamylase when added near the end of the mix cycle. In bread or other baked goods, particularly those having a low fat content, e.g., French-style breads, an enveloped glucoamylase mixture of approximately 1% of the dry flour weight is sufficient to admix the enveloped glucoamylase properly with the dough. The range of suitable percentages is wide and depends on the formula, finished product, and production methodology requirements of the individual baker. Second, the enveloped glucoamylase suspension should be added to the mix with sufficient time for complete mixture into the dough, but not for such a time that excessive mechanical action strips the protective lipid coating from the enveloped glucoamylase particles.

A food composition is contemplated where the food is an oil, meat, lard, composition comprising an AfGATR or a variant thereof. In this context the term "[oil/meat/lard] composition" means any composition, based on, made from and/or containing oil, meat or lard, respectively. A method is contemplated for preparing an oil or meat or lard composition and/or additive comprising an AfGATR or a variant thereof, comprising mixing the polypeptide of the invention with a oil/meat/lard composition and/or additive ingredients.

The food composition can be an animal feed composition, animal feed additive, and/or pet food comprising an AfGATR and variants thereof. A method is contemplated for preparing such an animal feed composition, animal feed additive composition and/or pet food comprising mixing an AfGATR and variants thereof with one or more animal feed ingredients and/or animal feed additive ingredients and/or pet food ingredients. An AfGATR and variants thereof can be used in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to dogs, cats, gerbils, hamsters, chinchillas, fancy rats, guinea pigs; avian pets, such as *canaries*, parakeets, and parrots; reptile pets, such as turtles, lizards and snakes; and aquatic pets, such as tropical fish and frogs.

The terms "animal feed composition," "feedstuff" and "fodder" are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

6. Textile Desizing Compositions and Use

Also contemplated are compositions and methods of treating fabrics (e.g., to desize a textile) using an AfGATR. Fabric-treating methods are well known in the art (see, e.g., U.S. Pat. No. 6,077,316). For example, the feel and appearance of a fabric can be improved by a method comprising contacting the fabric with an AfGATR in a solution. The fabric can be treated with the solution under pressure.

An AfGATR can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. An AfGATR can be applied during or after the weaving to remove these sizing starches or starch derivatives. After weaving, an AfGATR can be used to remove the size coating before further processing the fabric to ensure a homogeneous and wash-proof result.

An AfGATR can be used alone or with other desizing chemical reagents and/or desizing enzymes to desize fabrics, including cotton-containing fabrics, as detergent additives, e.g., in aqueous compositions. An AfGATR also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. An AfGATR can be used in methods of finishing denim garments (e.g., a "bio-stoning process"), enzymatic desizing and providing softness to fabrics, and/or finishing process.

7. Cleaning Compositions

An aspect of the present compositions and methods is a cleaning composition that includes an AfGATR or variant thereof as a component. An amylase polypeptide can be used as a component in detergent compositions for hand washing, laundry washing, dishwashing, and other hard-surface cleaning.

7.1. Overview

Preferably, the AfGATR or variant thereof is incorporated into detergents at or near a concentration conventionally used for amylase in detergents. For example, an glucoamylase polypeptide may be added in amount corresponding to 0.00001-1 mg (calculated as pure enzyme protein) of amylase per liter of wash/dishwash liquor. Exemplary formulations are provided herein, as exemplified by the following:

A glucoamylase polypeptide may be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Other enzyme stabilizers are known in the art. Protected enzymes may be prepared according to the method disclosed in for example EP 238 216. Polyols have long been recognized as stabilizers of proteins, as well as improving protein solubility.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as proteases, another amylolytic enzyme, cutinase, lipase, cellulase, pectate lyase, perhydrolase, xylanase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically amylases, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibiters, optical brighteners, or perfumes.

The pH (measured in aqueous solution at use concentration) is usually neutral or alkaline, e.g., pH about 7.0 to about 11.0.

Particular forms of detergent compositions for inclusion of the present glucoamylase are described, below.

7.2. Heavy Duty Liquid (HDL) Laundry Detergent Composition

Exemplary HDL laundry detergent compositions includes a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulphobetaines); ampholytic surfactants; semi-polar non-ionic surfactants and mixtures thereof.

The composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition may include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and copolymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition may further include saturated or unsaturated fatty acid, preferably saturated or unsaturated $C_{12}$-$C_{24}$ fatty acid (0 wt % to 10 wt %); deposition aids examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition may further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetracetic acid (PDT A), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition preferably included enzymes (generally about 0.01 wt % active enzyme to 0.03 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may include an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition optionally include silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof. The composition may be in any unit dose form, for example a pouch.

7.3. Heavy Duty Dry/Solid (HDD) laundry detergent composition

Exemplary HDD laundry detergent compositions includes a detersive surfactant, including anionic detersive surfactants (e.g., linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines), ampholytic surfactants, semi-polar non-ionic surfactants, and mixtures thereof; builders including phosphate free builders (for example zeolite builders examples which include zeolite A, zeolite X, zeolite P and zeolite MAP in the range of 0 wt % to less than 10 wt %), phosphate builders (for example sodium tri-polyphosphate in the range of 0 wt % to less than 10 wt %), citric acid, citrate salts and nitrilotriacetic acid, silicate salt (e.g., sodium or potassium silicate or sodium meta-silicate in the range of 0 wt % to less than 10 wt %, or layered silicate (SKS-6)); carbonate salt (e.g., sodium carbonate and/or sodium bicarbonate in the range of 0 wt % to less than 80 wt %); and bleaching agents including photobleaches (e.g., sulfonated zinc phthalocyanines, sulfonated aluminum phthalocyanines, xanthenes dyes, and mixtures thereof) hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), sources of hydrogen peroxide (e.g., inorganic perhydrate salts examples of which include mono or tetra hydrate sodium salt of perborate, percarbonate, persulfate, perphosphate, or persilicate), preformed hydrophilic and/or hydrophobic peracids (e.g., percarboxylic acids and salts, percarbonic acids and salts, perimidic acids and salts, peroxymonosulfuric acids and salts, and mixtures thereof), and/or bleach catalysts (e.g., imine bleach boosters (examples of which include iminium cations and polyions), iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof, and metal-containing bleach catalysts (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid), and water-soluble salts thereof).

The composition preferably includes enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition may optionally include additional detergent ingredients including perfume microcapsules, starch encapsulated perfume accord, hueing agents, additional polymers, including fabric integrity and cationic polymers, dye-lock ingredients, fabric-softening agents, brighteners (for example C.I. Fluorescent brighteners), flocculating agents, chelating agents, alkoxylated polyamines, fabric deposition aids, and/or cyclodextrin.

7.4. Automatic Dishwashing (ADW) Detergent Composition

Exemplary ADW detergent composition includes non-ionic surfactants, including ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% including phosphate builders (e.g., mono-phosphates, di-phosphates, tri-polyphosphates, other oligomeric-poylphosphates, sodium tripolyphosphate-STPP) and phosphate-free builders (e.g., amino acid-based compounds including methyl-glycine-diacetic acid (MGDA) and salts and derivatives thereof, glutamic-N,N-diacetic acid (GLDA) and salts and derivatives thereof, iminodisuccinic acid (IDS) and salts and derivatives thereof, carboxy methyl inulin and salts and derivatives thereof, nitrilotriacetic acid (NTA), diethylene triamine penta acetic acid (DTPA), B-alaninediacetic acid (B-ADA) and their salts, homopolymers and copolymers of poly-carboxylic acids and their partially or completely neutralized salts, monomeric polycarboxylic acids and hydroxycarboxylic acids and their salts in the range of 0.5% to 50% by weight; sulfonated/carboxylated polymers in the range of about 0.1% to about 50% by weight to to provide dimensional stability; drying aids in the range of about 0.1% to about 10% by weight (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds, thereof, particularly of the reactive cyclic carbonate and urea type); silicates in the range from about 1% to about 20% by weight (including sodium or potassium silicates for example sodium disilicate, sodium meta-silicate and crystalline phyllosilicates); inorganic bleach (e.g., perhydrate salts such as perborate, percarbonate, perphosphate, persulfate and persilicate salts) and organic bleach (e.g., organic peroxyacids, including diacyl and tetraacylperoxides, such as diperoxydodecanedioc acid, diperoxytetradecanedioc acid, and diperoxyhexadecanedioc acid); bleach activators (i.e., organic peracid precursors in the range from about 0.1% to about 10% by weight); bleach catalysts (e.g., manganese triazacyclononane and related complexes, Co, Cu, Mn, and Fe bispyridylamine and related complexes, and pentamine acetate cobalt(III) and related complexes); metal care agents in the range from about 0.1% to 5% by weight (e.g., benzatriazoles, metal salts and complexes, and/or silicates); enzymes in the range from about 0.01 to 5.0 mg of active enzyme per gram of automatic dishwashing detergent composition (e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and mixtures thereof); and enzyme stabilizer components (e.g., oligosaccharides, polysaccharides, and inorganic divalent metal salts).

7.5. Additional Detergent Compositions

Additional exemplary detergent formulations to which the present amylase can be added are described, below, in the numbered paragraphs.

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in "Efficient manganese catalysts for low-temperature bleaching," *Nature* 369: 637-639 (1994).

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

As above, the present amylase polypeptide may be incorporated at a concentration conventionally employed in detergents. It is at present contemplated that, in the detergent composition, the enzyme may be added in an amount corresponding to 0.00001-1.0 mg (calculated as pure enzyme protein) of amylase polypeptide per liter of wash liquor.

The detergent composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

The detergent composition may be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

Any of the cleaning compositions described, herein, may include any number of additional enzymes. In general the enzyme(s) should be compatible with the selected detergent, (e.g., with respect to pH-optimum, compatibility with other enzymatic and non-enzymatic ingredients, and the like), and the enzyme(s) should be present in effective amounts. The following enzymes are provided as examples.

Proteases:

Suitable proteases include those of animal, vegetable or microbial origin. Chemically modified or protein engineered mutants are included, as well as naturally processed proteins. The protease may be a serine protease or a metalloprotease, an alkaline microbial protease, a trypsin-like protease, or a chymotrypsin-like protease. Examples of alkaline proteases are subtilisins, for example those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, KANNASE™, and BLAZE™ (Novo Nordisk A/S and Novozymes A/S); MAXATASE®, MAXACAL™, MAXAPEM™, PROPERASE®, PURAFECT®, PURAFECT OXP™, FN2™ and FN3™ (Danisco US Inc.). Other exemplary proteases include NprE from *Bacillus amyloliquifaciens* and ASP from *Cellulomonas* sp. strain 69B4.

Lipases:

Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta*, 1131: 253-360 (1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S and Novozymes A/S).

Polyesterases:

Suitable polyesterases can be included in the composition, such as those described in, for example, WO 01/34899, WO 01/14629, and U.S. Pat. No. 6,933,140.

Amylases:

The compositions can be combined with amylases, such as non-production enhanced amylase. These can include commercially available amylases, such as but not limited to STAINZYME®, NATALASE®, DURAMYL®, TERMAMYL®, FUNGAMYL® and BAN™ (Novo Nordisk A/S and Novozymes A/S); RAPIDASE®, POWERASE®, and PURASTAR® (from Danisco US Inc.).

Cellulases:

Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S and Novozymes A/S); CLAZINASE® and PURADAX HA® (Danisco US Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S and Novozymes A/S).

The detergent composition can also comprise 2,6-β-D-fructan hydrolase, which is effective for removal/cleaning of biofilm present on household and/or industrial textile/laundry.

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, and the like. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly(vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is contemplated that in the detergent compositions, in particular the enzyme variants, may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

Although the present compositions and methods have been described with reference to the details below, it would be understood that various modifications can be made.

7.6. Methods of Assessing Amylase Activity in Detergent Compositions

Numerous glucoamylase cleaning assays are known in the art, including swatch and micro-swatch assays. The appended Examples describe only a few such assays.

8. Brewing Compositions

An AfGATR or variant thereof may be a component of a brewing composition used in a process of providing a fermented beverage, such as brewing. It is believed that non-fermentable carbohydrates form the majority of the dissolved solids in the final beer. This residue remains because of the inability of malt amylases to hydrolyze the alpha-1,6-linkages of the starch. The non-fermentable carbohydrates contribute about 50 calories per 12 ounces (about 340 grams) of beer. The AfGATR or variant thereof, usually in combination with a glucoamylase and optionally a pullulanase and/or isoamylase, assist in converting the starch into dextrins and fermentable sugars, lowering the residual non-fermentable carbohydrates in the final beer.

The principal raw materials used in making these beverages are water, hops and malt. In addition, but also exclusively adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch.

For a number of reasons, the malt, which is produced principally from selected varieties of barley, has an important effect on the overall character and quality of the beer. First, the malt is the primary flavoring agent in beer. Second, the malt provides the major portion of the fermentable sugar. Third, the malt provides the proteins, which will contribute to the body and foam character of the beer. Fourth, the malt provides the necessary enzymatic activity during mashing. Hops also contribute significantly to beer quality, including flavoring. In particular, hops (or hops constituents) add desirable bittering substances to the beer. In addition, the hops can act as protein precipitants, establish preservative agents and aid in foam formation and stabilization.

Cereals (grains), such as barley, oats, wheat, but also corn and rice are often used for brewing, both in industry and for home brewing, but also other plant components, such as hops are often added. The components used in brewing may be unmalted or may be malted, i.e., partially germinated, resulting in an increase in the levels of enzymes, including α-amylase. For successful brewing, adequate levels of α-amylase enzyme activity are necessary to ensure the appropriate levels of sugars for fermentation. An AfGATR or variant thereof may also be added to the components used for brewing.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. The methods described herein may be used to determine α-amylase activity levels in both flours and stock.

Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer. Typically, milled or crushed malt, malt and adjunct, or adjunct is mixed with water and held for a period of time under controlled temperatures to permit the enzymes present in the malt and/or adjunct to convert the starch present in the malt into fermentable sugars. The mash is then transferred to a mash filter where the liquid is separated from the grain residue. This sweet liquid is called "wort," and the left over grain residue is called "spent grain." The mash is typically subjected to an extraction, which involves adding water to the mash in order to recover the residual soluble extract from the spent grain. The wort is then boiled vigorously to sterilizes the wort and help develop the color, flavor and odor. Hops are added at some point during the boiling. The wort is cooled and transferred to a fermentor.

The wort is then contacted in a fermentor with yeast. The fermentor may be chilled to stop fermentation. The yeast that may flocculate is removed. Finally, the beer is cooled and stored for a period of time, during which the beer clarifies and its flavor develops, and any material that might impair the appearance, flavor, and shelf life of the beer settles out. The beer usually contains from about 2% to about 10% v/v alcohol, although beer with a higher alcohol content, e.g., 18% v/v, may be obtained. Prior to packaging, the beer is carbonated and, optionally, filtered, and pasteurized.

The brewing composition comprising an alpha-amylase, often, but not necessarily in combination with one or more exogenous enzymes, such as glucoamylase(s) (e.g. AfGATR or variant thereof), pullulanase(s) and/or isoamylase(s), and any combination thereof, may be added to the mash of step (a) above, i.e., during the preparation of the mash. Alternatively, or in addition, the brewing composition may be added to the mash of step (b) above, such as during the filtration of the mash. Alternatively, or in addition, the brewing composition may be added to the wort of step (c) above, such as during the fermenting of the wort.

Particular embodiments pertains to any of the above uses, methods or fermented beverages, wherein said fermented beverage is a beer, such as full malted beer, beer brewed under the "Reinheitsgebot," ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e.g., citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

9. Reduction of Iodine-Positive Starch

AfGATR and variants thereof may reduce the iodine-positive starch (IPS), when used in a method of liquefaction and/or saccharification. One source of IPS is from amylose that escapes hydrolysis and/or from retrograded starch polymer. Starch retrogradation occurs spontaneously in a starch paste, or gel on ageing, because of the tendency of starch molecules to bind to one another followed by an increase in crystallinity. Solutions of low concentration become increasingly cloudy due to the progressive association of starch molecules into larger articles. Spontaneous precipitation takes place and the precipitated starch appears to be reverting to its original condition of cold-water insolubility. Pastes of higher concentration on cooling set to a gel, which on ageing becomes steadily firmer due to the increasing association of the starch molecules. This arises because of the strong tendency for hydrogen bond formation between hydroxy groups on adjacent starch molecules. See J. A. Radley, ed., STARCH AND ITS DERIVATIVES 194-201 (Chapman and Hall, London (1968)).

The presence of IPS in saccharide liquor negatively affects final product quality and represents a major issue with downstream processing. IPS plugs or slows filtration system, and fouls the carbon columns used for purification. When IPS reaches sufficiently high levels, it may leak through the carbon columns and decrease production efficiency. Additionally, it may results in hazy final product upon storage, which is unacceptable for final product quality. The amount of IPS can be reduced by isolating the saccharification tank and blending the contents back. IPS nevertheless will accumulate in carbon columns and filter systems, among other things. The use of AfGATR or variants thereof thus is expected to improve overall process performance by reducing the amount of IPS.

In order to further illustrate the compositions and methods, and advantages thereof, the following specific examples are given with the understanding that they are illustrative rather than limiting.

EXAMPLES

Example 1: Cloning of AfGA1

Genomic DNA of *Aspergillus fumigatus* Af293 was purchased from Fungal Genetics Stock Center, Kansas City, Mo. (FGSC A1100). The genome of *Aspergillus fumigatus* is sequenced. The nucleic acid sequence for the AfGA1 gene (within the disclosed genome in NCBI Reference Sequence NC 007195), and the amino acid sequence of the predicted glucan 1,4-alpha-glucosidase (NCBI Accession No. XP 749206) encoded by the AfGA1 gene were obtained in the NCBI Databases. AfGA1 is homologous to other fungal glucoamylases as determined from a BLAST search. See FIG. 1. The nucleotide sequence of the AfGA1 gene, which comprises three introns, is set forth in SEQ ID NO: 8.

The AfGA1 gene was amplified from genomic DNA of *Aspergillus fumigatus* using the following primers: Primer 1: AfGA1-Fw 5'-GCG GCGGCCGC ACC atgcctcgcctttc-ctacgc-3' (SEQ ID NO: 9), and Primer 2: AfGA1-Ry 5'-cc ggcgcgcc TTA tcactgccaagtatcattctcg-3' (SEQ ID NO: 10). The forward primer contains a NotI restriction site, and the reverse primer contains an AscI restriction site. After digestion with NotI and AscI, the PCR product was cloned into the pTrex3gM expression vector (described in U.S. Published Application 2011/0136197 A1) digested with the same restriction enzymes, and the resulting plasmid was labeled pJG222. A plasmid map of pJG222 is provided in FIG. 2. The sequence of the AfGA1 gene was confirmed by DNA sequencing.

Example 2: Expression and Purification of AfGA1TR

The plasmid pJG222(Trex3gM-AfGA1) was transformed into a quad-deleted *Trichoderma reesei* strain (described in WO 05/001036) using biolistic method (Te'o et al., *J. Microbiol. Methods* 51: 393-99, 2002). Transformed colonies (about 50) appeared in about 1 week. After growth on acetamide plates for 5 days, the colonies were inoculated in 250 ml shake flasks with 30 ml Glucose/Sepharose defined medium for protein expression. The protein, AfGA1TR, was secreted into the extracellular medium, and the filtered culture medium was used to perform SDS-PAGE and a glucoamylase activity on DP7 assay to confirm the enzyme expression.

The stable strain was subsequently grown in a 7 L fermenter in a defined medium. Fermentation broth was harvested by centrifugation. Following centrifugation, filtration and concentration, 450 ml of the concentrated sample was obtained. The concentration of total protein in the sample was determined to be 83.70 g/L by using BCA method (protein quantification kit, Shanghai Generay Biotech CO., Ltd). SDS-PAGE analysis suggested that 80% of the total protein was the target protein. Thus, the concentration of target protein in the concentrated sample was estimated to be 66.96 g/L.

AfGA1TR was purified by affinity chromatography using an AKTA Explorer 100 FPLC system (GE Healthcare). β-Cyclodextrin (Sigma-Aldrich, 856088) was coupled to epoxy-activated Sepharose beads (GE Healthcare, 17-0480-01) and employed for purification. The pH of 40 ml concentrated fermentation broth from the 7 L fermenter was adjusted to 4.3 and the solution was loaded onto 30 ml β-CD-Sepharose column pre-equilibrated with 25 mM, pH 4.3 sodium acetate (buffer A). The column was washed with a 2 column volume of buffer A. The target protein was eluted with three column volume of buffer B which containing buffer A and 10 mM α-cyclodextrin (Sigma-Aldrich, C4642). Fractions were analyzed by SDS-PAGE gel, and assayed for glucoamylase activity. The fractions containing target protein were pooled and run through a Hiprep 26×10 desalting column to remove β-cyclodextrin. The resulting sample was more than 95% pure, the solution was concentrated using 10K Amicon Ultra-15 devices and stored in 40% glycerol at −80° C.

Example 3: Determination of AfGA1TR Substrate Specificity

Glucoamylase activity was assayed based on the release of glucose by glucoamylases, AfGA1TR, AnGA or wild-type AfGA, from different substrates, including maltose, isomaltose, maltoheptaose (DP7), maltodextrin (DE4-DE10), potato amylopectin, and soluble starch. The rate of glucose release was measured using a coupled glucose oxidase/peroxidase (GOX/HRP) method (*Anal. Biochem.* 105 (1980), 389-397). Glucose was quantified as the rate of oxidation of 2,2'-Azino-bis 3-ethylbenzothiazoline-6-sulfonic acid (ABTS) by peroxide which was generated from coupled GOX/HRP enzymes reacted with glucose.

Substrate solutions were prepared by mixing 9 mL of each substrate (1% in water, w/w) and 1 mL of 0.5 M pH 5.0 sodium acetate buffer in a 15-mL conical tube. Coupled enzyme (GOX/HRP) solution with ABTS was prepared by dissolving GOX/HRP in 50 mM sodium acetate buffer (pH 5.0), with the final concentrations of 2.74 mg/mL ABTS, 0.1 U/mL HRP, and 1 U/mL GOX.

Serial dilutions of glucoamylase samples, the benchmark AnGA (Genencor product, Optidex L-400), wild-type AfGA, and glucose standard were also prepared in 50 mM sodium acetate buffer (pH 5.0). Each glucoamylase sample (10 µl) was transferred into a new microtiter plate (Corning 3641) containing 90 µl of substrate solution preincubated at 50° C. for 5 min at 600 rpm. The reactions were carried out at 50° C. for 10 min with shaking (600 rpm) in a thermomixer (Eppendorf), 10 µl of reaction mixtures as well as 10 µl of serial dilutions of glucose standard were quickly transferred to new microtiter plates (Corning 9017), respectively, followed by the addition of 100 µl of ABTS/GOX/HRP solution. The microtiter plates containing the reaction mixture were immediately measured at 405 nm at 11 seconds intervals for 5 min on SoftMax Pro plate reader (Molecular Device). The output was the reaction rate, Vo, for each enzyme concentration. Linear regression was used to determine the slope of the plot Vo vs. enzyme dose. The specific activity of glucoamylase activity was calculated based on the glucose standard curve using Equation 1:

$$\text{Specific Activity(Unit/mg)} = \text{Slope(enzyme)}/\text{slope(std)} \times 100 \quad (1),$$

where 1 Unit=1 µmol glucose/min.

Representative specific activities of AfGA1TR and the benchmark glucoamylases AnGA and wild-type AfGA are shown in Table 1.

TABLE 1

Specific activity of purified glucoamylases on various substrates.

| | Specific activity (U/mg) | | |
|---|---|---|---|
| Substrate | AnGA | Wild-type AfGA | AfGA1TR |
| Maltose (DP2) | 29.2 | 29.2 | 42.7 |
| Isomaltose | 0 | 0.6 | 0.9 |
| Maltoheptaose (DP7) | 159.9 | 180.3 | 254.8 |
| Maltodextrin (DE4-10DE) | 128.8 | 127.8 | 211.5 |
| Amylopectin from potato | 142.5 | 146.5 | 197.8 |
| Soluble starch | 137.5 | 128.0 | 213.4 |
| Pullulan | 29.2 | 25.6 | 31.1 |

Example 4: Effect of pH on AfGA1TR Glucoamylase Activity

Figure 3:
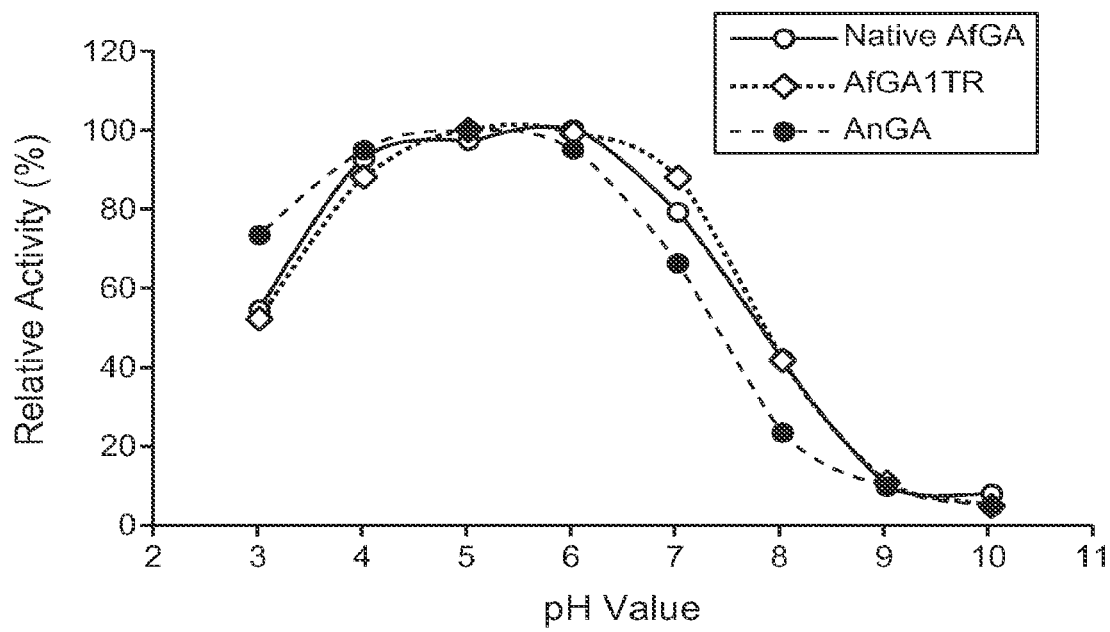
FIG. 3 depicts the dependence of glucoamylase activity (relative units) on pH. The glucoamylases include (1) wild-type AfGA expressed in *Aspergillus fumigatus*, (2) AfGA1TR expressed in *Trichoderma reesei*, and (2) AnGA expressed in *Aspergillus niger*. Glucoamylase activity was assayed by the release of glucose from soluble starch at 50° C.

The effect of pH (from 3.0 to 10.0) on AfGA1TR activity was monitored using the ABTS assay protocol as described in Example 3. Buffer working solutions consisted of the combination of glycine/sodium acetate/HEPES (250 mM), with pH varying from 3.0 to 10.0. Substrate solutions were prepared by mixing soluble starch (1% in water, w/w) with 250 mM buffer solution at a ratio of 9:1. Enzyme working solutions were prepared in water at a certain dose (showing signal within linear range as per dose response curve). All the incubations were carried out at 50° C. for 10 min following the same protocol as described for gluco-amylase activity assay in Example 3. Enzyme activity at each pH was reported as relative activity compared to enzyme activity at optimum pH. The pH profile of AfGA1TR is shown in Table 2 and FIG. 3. AfGA1TR was found to have an optimum pH at about 5.0, and retain greater than 70% of maximum activity between pH 3.5 and 7.5.

TABLE 2 pH profiles for purified glucoamylases

| | Relative activity (%) | | |
|---|---|---|---|
| pH | AnGA | Native AfGA | AfGA1TR |
| 3 | 73.5 | 54.9 | 52.6 |
| 4 | 94.9 | 92.5 | 88.3 |
| 5 | 100 | 97.6 | 100 |
| 6 | 95.2 | 100 | 99.3 |
| 7 | 66.5 | 79.2 | 87.9 |
| 8 | 23.8 | 43 | 42.1 |
| 9 | 9.9 | 11 | 11.7 |
| 10 | 5.3 | 8.4 | 5.3 |

Example 5: Effect of Temperature on AfGA1TR Glucoamylase Activity

Figure 4:
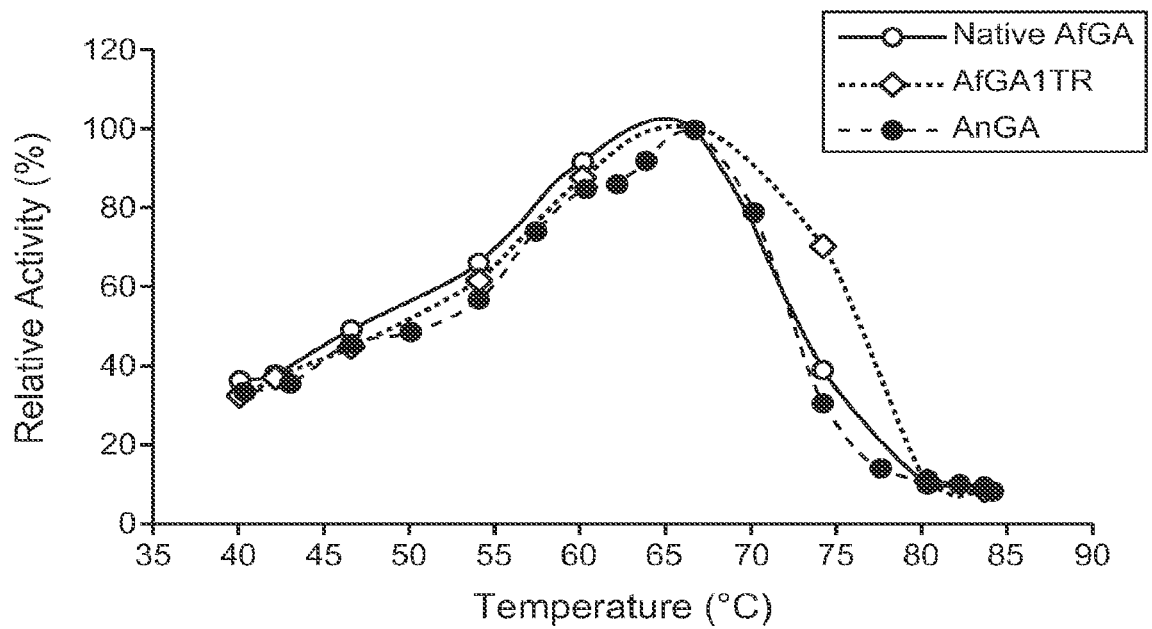
FIG. 4 depicts the dependence of glucoamylase activity (relative units) on temperature. The glucoamylases include (1) wild-type AfGA expressed in *Aspergillus fumigatus*, (2) AfGA1TR expressed in *Trichoderma reesei*, and (3) and AnGA. Glucoamylase activity was assayed by the release of glucose from soluble starch at pH 5.0.

The effect of temperature (from 40° C. to 84° C.) on AfGA1TR activity was monitored using the ABTS assay protocol as described in Example 3. Substrate solutions were prepared by mixing 3.6 mL of soluble starch (1% in water, w/w) and 0.4 mL of 0.5 M buffer (pH 5.0 sodium acetate) into a 15-mL conical tube. Enzyme working solutions were prepared in water at a certain dose (showing signal within linear range as per dose response curve). Incubations were done at temperatures from 40° C. to 84° C., respectively, for 10 min following the same protocol as described for glucoamylase activity assay in Example 3. Enzyme activity at each temperature was reported as relative activity compared to enzyme activity at optimum temperature. The temperature profile of AfGA1TR is shown in Table 3 and FIG. 4. AfGA1TR was found to have an optimum temperature of 68° C., and retain greater than 70% of maximum activity between 56° C. and 74° C.

TABLE 3

Temperature profiles for glucoamylases.

| Temp (° C.) | Relative activity (%) | | |
|---|---|---|---|
| | AnGA | Native AfGA | AfGA1TR |
| 40 | 33.9 | 36.6 | 32.7 |
| 42.1 | 36 | 38.2 | 37.6 |
| 46.5 | 46.1 | 49.4 | 45 |
| 54 | 57.2 | 66.3 | 61.9 |
| 60 | 85.1 | 91.9 | 87.1 |
| 66.6 | 100 | 100 | 100 |
| 74.1 | 31.1 | 39.4 | 70.4 |
| 80.2 | 11.8 | 10.9 | 11.2 |
| 83.5 | 8.8 | 9.6 | 8.8 |

Example 6: AfGA1TR Product Profile Analysis

To assay the products of fungal glucoamylase catalysis of polysaccharides, the glucoamylases, AnGA (0.118 mg/gds starch) and AfGA1TR (0.118 mg/gds or 0.059 mg/gds), were incubated with 34% DS LIQUOZYME® Supra liquefied starch (CPI, Stockton, Calif.), at 60° C., pH 4.2 to 4.5 for 2 days. Pullulanase (PU) and acid-stable alpha-amylase from *Aspergillus kawachii*, GC626® (AkAA) were dosed along with purified AfGA1TR at 0.256 ASPU/gds and 0.35 SSU/gds, respectively. Samples were taken at different intervals of time and analyzed for sugar composition by HPLC.

Figures 6A, 6B:
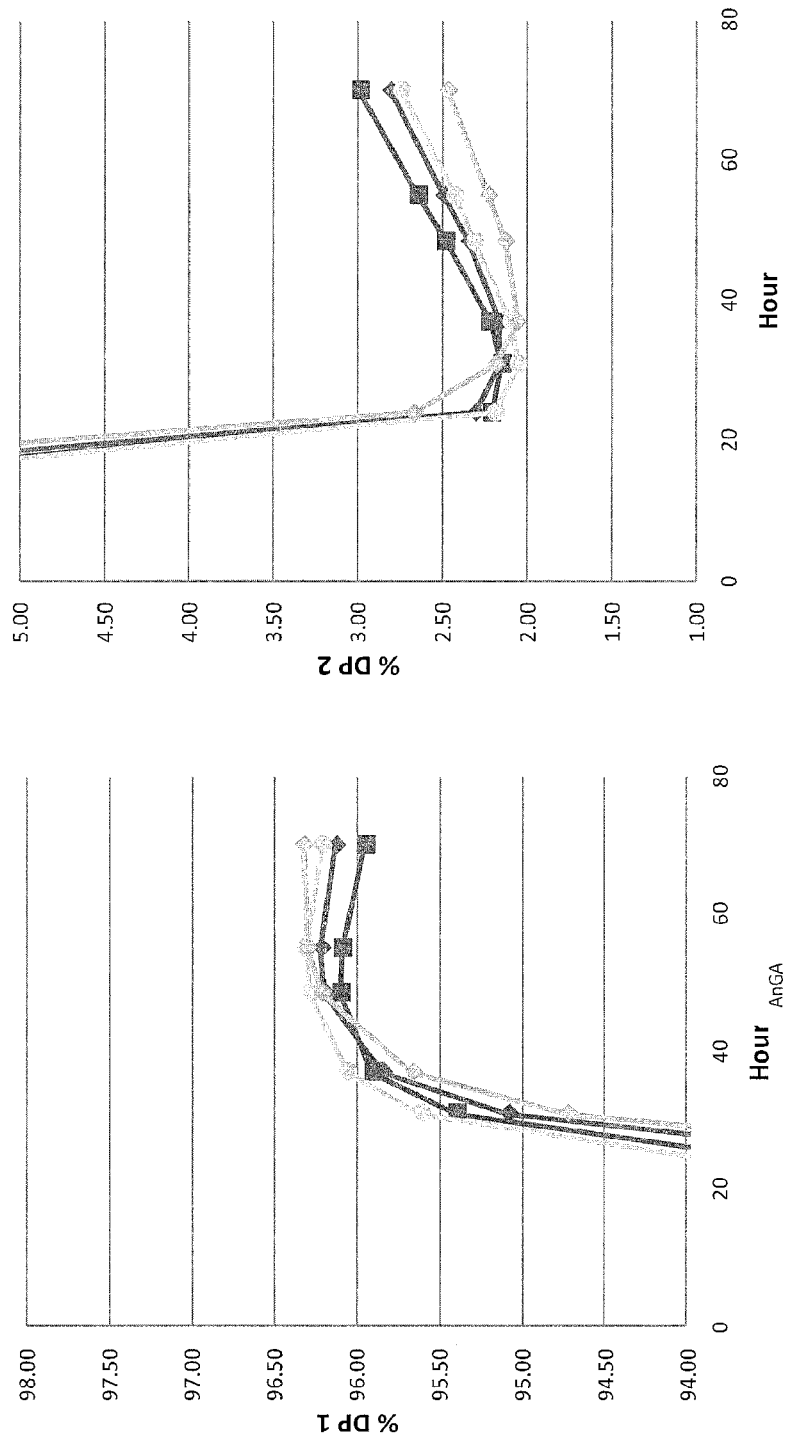
FIGS. 6A-B depict the hydrolysis of 35% dry solid starch to DP1 and reversion of DP1 to DP2 by a composition containing AfGATR1, pullulanase and AkAA.

Table 4 shows the profile of oligosaccharides saccharified by AnGA/PU/AkAA and AfGA1TR/PU/AkAA at 100% and 50% the concentration of AnGA. (FIG. 6 depicts the profile of oligosaccharides saccharified by AnGA and AfGA1TR at 100%, 50%, and 40% the concentration of AnGA, with and without PU and AkAA). Only oligosaccharides with DP1, DP2, DP3, and HS are shown. The numbers in Table 4 reflect the weight percentage of each DPn as a fraction of the total DP1, DP2, DP3, and HS.

TABLE 4

Product profile of fungal glucoamylases on liquefied starch.

| Flask | Enzymes | Dose:/gds | Hr | % DP1 | % DP2 | % DP3 | % HS |
|---|---|---|---|---|---|---|---|
| 1 | An-GA + PU + GC626 | 0.118 mg + 0.256ASPU + 0.35SSU | 8 | 69.75 | 9.29 | 0.66 | 20.30 |
| | | | 24 | 93.40 | 2.21 | 0.71 | 3.68 |
| | | | 31 | 95.40 | 2.15 | 0.67 | 1.79 |
| | | | 37 | 95.90 | 2.22 | 0.60 | 1.27 |
| | | | 48.5 | 96.10 | 2.48 | 0.53 | 0.89 |
| | | | 55 | 96.09 | 2.64 | 0.49 | 0.78 |
| | | | 70 | 95.95 | 2.99 | 0.45 | 0.62 |
| 2 | AfGA1TR + PU + GC626 | 0.118 mg + 0.256ASPU + 0.35SSU | 8 | 86.34 | 2.35 | 0.47 | 10.84 |
| | | | 24 | 96.01 | 2.29 | 0.49 | 1.21 |
| | | | 31 | 96.11 | 2.58 | 0.44 | 0.88 |
| | | | 37 | 96.03 | 2.84 | 0.42 | 0.71 |
| | | | 48.5 | 95.70 | 3.33 | 0.43 | 0.54 |
| | | | 55 | 95.52 | 3.56 | 0.44 | 0.48 |
| | | | 70 | 94.97 | 4.12 | 0.49 | 0.42 |
| 3 | AfGA2TR + PU + GC626 | 0.059 mg + 0.256ASPU + 0.35SSU | 8 | 71.27 | 9.07 | 0.61 | 19.05 |
| | | | 24 | 93.80 | 2.19 | 0.72 | 3.29 |
| | | | 31 | 95.61 | 2.06 | 0.68 | 1.65 |
| | | | 37 | 96.06 | 2.09 | 0.63 | 1.22 |
| | | | 48.5 | 96.29 | 2.31 | 0.54 | 0.86 |
| | | | 55 | 96.31 | 2.43 | 0.50 | 0.76 |
| | | | 70 | 96.21 | 2.74 | 0.45 | 0.59 |

Table 4 showed that AfGA1TR resulted in >95.5% DP1 in 24 hours, compared to AnGA which took 48.5 hours under an equal dose of protein. The data in Table 4 showed that AfGA1TR demonstrated an improved performance over AnGA at 50% dose equivalent based on protein (under the identical conditions of complimentary enzymes dosage).

Example 7: Comparison of DP2 Levels

DP2 level from AfGA1TR treated liquified starch was compared to the one from AnGA treated liquified starch based on the same DP1 level (96%). The comparison showed a statistically significant reduction in DP2 level at equal DP1 level approx. by 0.2%, possibly due to lower glucoamylase dose. Reversion reaction by AnGA and AfGA1TR (as the triple blend) was measured by calculating isomaltose/maltose ratio through ion chromatography.

TABLE 5

Product profile of fungal glucoamylases on liquefied starch.

| | Hour | % of the total composition after glucoamylase reaction | | % of the total DP2 after glucoamylase reaction | | reversion reaction Ratio | |
|---|---|---|---|---|---|---|---|
| | | % DP1 | % DP2 | % IsoMaltose | % Maltose | (IsoM/M) | ΔRatio |
| AnGA | 48 | 96.08 | 2.26 | 55.6 | 44.4 | 1.25 | |
| | 70 | 95.91 | 2.77 | 64.9 | 35.1 | 1.85 | |
| AfGA1TR | 48 | 96.16 | 2.13 | 54.8 | 45.2 | 1.21 | 0.04 |
| | 70 | 96.10 | 2.60 | 63.4 | 36.6 | 1.73 | 0.13 |

Δ Ratio = [AnGA ratio − AfGA1TR ratio] at 48 and 70 hours

Table 5 shows that for both glucoamylases isomaltose is accumulating over time according to increasing ratio of Isomaltose:Maltose. However, isomaltose formation appears to be slightly lower with AfGA1TR because the difference of ratio between AnGA and AfGA1TR is increased from 48 hours to 70 hours, which may support the lower reversion reaction by AfGA1TR.

Example 8: Titration of AkAA

To assay the products of fungal glucoamylase catalysis of polysaccharides using varied doses of accessory alpha-amylase, AfGA1TR (0.059 mg/gds) and Pullulanase (PU, OPTIMAX® L-1000)(0.256 ASPU/gds) were incubated with different concentrations of acid-stable alpha-amylase, GC626® (AkAA) from *Aspergillus kawachi*. AkAA was added at 0 to 0.3 SSU/ds in increments of 0.1 SSU and 34% DS LIQUOZYME® Supra liquefied starch (CPI, Stockton, Calif.), at 60° C., pH 4.5 for 2 days. Pullulanase (PU) and GC626® (AkAA) were dosed along with purified AfGA1TR at 0.256 ASPU/gds and 0.35 SSU/gds, respectively. Samples were taken at different intervals of time and analyzed for sugar composition by HPLC.

Figures 7A, 7B:
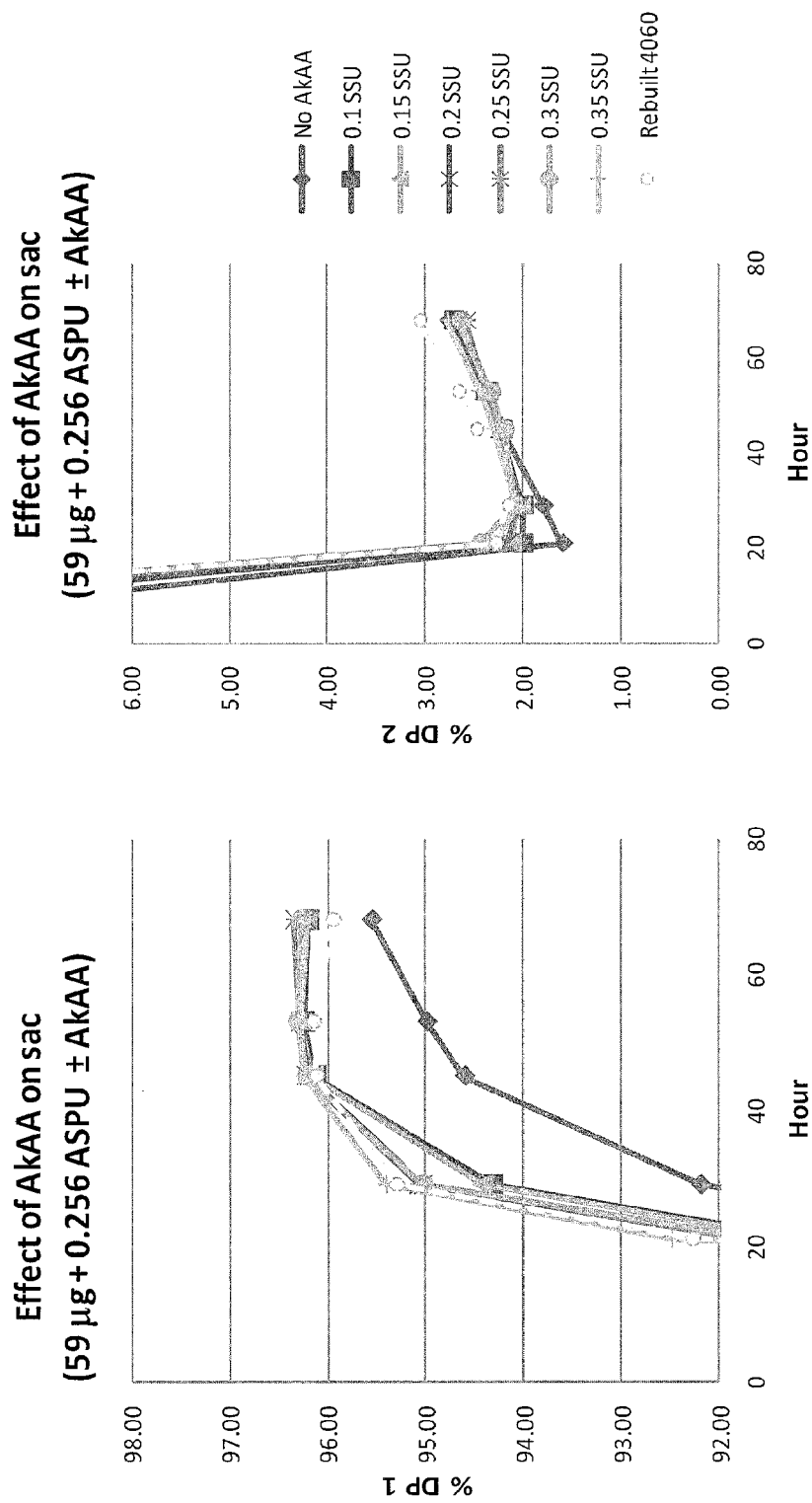
FIGS. 7A-B depict the hydrolysis of 35% dry solid starch to DP1 and reversion of DP1 to DP2 by a composition containing AfGATR1, pullulanase and varying doses of AkAA.
Figure 8:
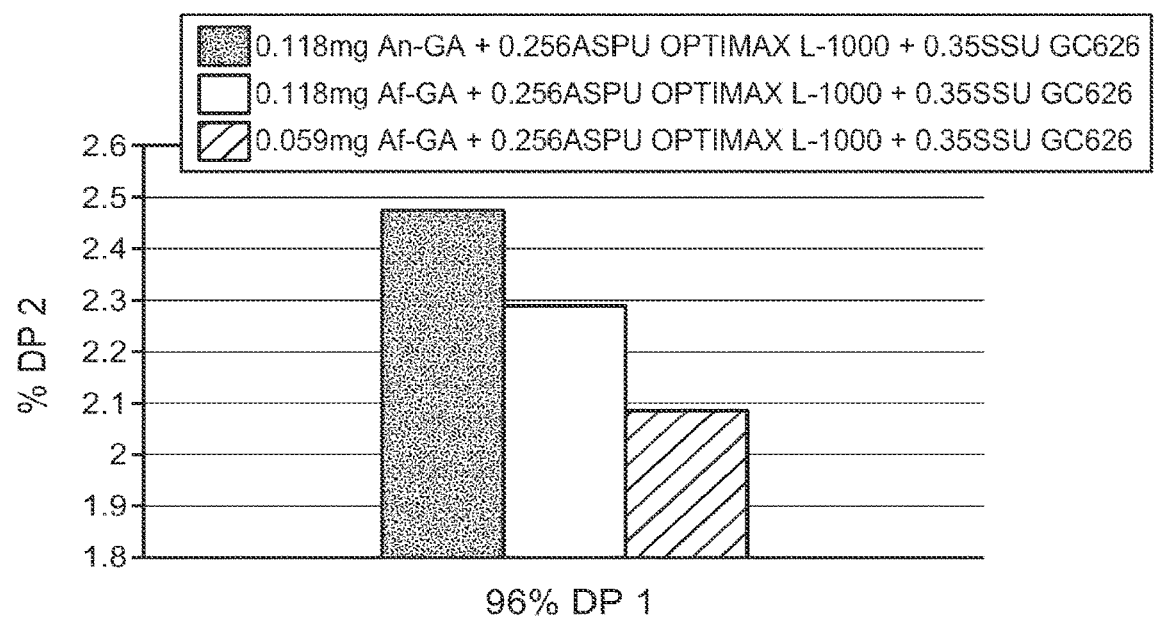
FIG. 8 depicts the amount of DP2 found in a high glucose composition containing 96% DP1 after the release of reducing sugar from a 35% dry solid starch by compositions containing AfGA1TR or AnGA, and further containing an alpha-amylase (OPTIMAX L-100) and PU (GC636).

Table 6 and FIG. 7 disclose profiles of oligosaccharides saccharified by AfGA1TR, PU and varying doses of AkAA. Only oligosaccharides with DP1, DP2, DP3 and HS are shown. The numbers in Table 6 reflect the weight percentage of each DPn as a fraction of the total DP1, DP2, DP3, and HS.

TABLE 6

Effect of AkAA during saccharification enzyme liquefied starch by AfGA1TR.

| Flask | AkAA (GC626 ®) dose:/gds | Hr | % DP1 | % DP2 | % DP3 | % HS |
|---|---|---|---|---|---|---|
| 1 | 0 | 6 | 64.43 | 8.51 | 0.68 | 26.37 |
|   |   | 21 | 88.93 | 1.60 | 0.46 | 9.01 |
|   |   | 29 | 92.19 | 1.80 | 0.45 | 5.56 |
|   |   | 45 | 94.60 | 2.22 | 0.40 | 2.78 |
|   |   | 53 | 94.99 | 2.40 | 0.38 | 2.23 |
|   |   | 68 | 95.55 | 2.77 | 0.37 | 1.30 |
| 2 | 0.1 SSU | 6 | 63.10 | 10.00 | 0.77 | 26.12 |
|   |   | 21 | 91.07 | 2.01 | 0.59 | 6.33 |
|   |   | 29 | 94.33 | 2.01 | 0.58 | 3.09 |
|   |   | 45 | 96.13 | 2.23 | 0.49 | 1.15 |
|   |   | 53 | 96.24 | 2.39 | 0.46 | 0.91 |
|   |   | 68 | 96.20 | 2.72 | 0.42 | 0.66 |
| 3 | 0.2 SSU | 6 | 63.66 | 10.47 | 0.92 | 24.96 |
|   |   | 21 | 91.75 | 2.18 | 0.65 | 5.43 |
|   |   | 29 | 95.03 | 2.05 | 0.64 | 2.28 |
|   |   | 45 | 96.19 | 2.25 | 0.52 | 1.03 |
|   |   | 53 | 96.28 | 2.41 | 0.48 | 0.83 |
|   |   | 68 | 96.22 | 2.73 | 0.43 | 0.62 |
| 4 | 0.3 SSU | 6 | 59.97 | 11.76 | 1.74 | 26.53 |
|   |   | 21 | 91.52 | 2.44 | 0.71 | 5.33 |
|   |   | 29 | 95.03 | 2.08 | 0.70 | 2.19 |
|   |   | 45 | 96.21 | 2.20 | 0.57 | 1.01 |
|   |   | 53 | 96.31 | 2.34 | 0.52 | 0.83 |
|   |   | 68 | 96.27 | 2.64 | 0.46 | 0.63 |

Table 6 shows that AfGA1TR was able to reach >96% DP1 in 45 hours in presence of at least 0.1 SSU/gds, while lack of AkAA resulted in a statistically significantly reduced rate of saccharification. The result indicates that a significant increase in the final glucose yield was achieved by the addition of AkAA during saccharification of enzyme liquefied starch by AfGA1TR.

Example 9: Solubilization and Hydrolysis of Granular Starch by an Enzyme Blend Containing Alpha-Amylase, AfGA1TR and Pullulanase Granular corn starch slurry having 35% dry solid starch in distilled water was prepared and the pH was adjusted to pH 5.0 using NaOH. 10 AAU/gds of alpha-amylase (SPEZYME® XTRA) and purified protein of AfGA1TR were added at 0.047 mg/gds along with 0.15 ASPU/gds of pullullanase (OPTIMAX® L-1000) to the starch slurry. Then, the starch slurry was kept in a water bath maintained at 60° C. with constant stirring. An aliquot was withdrawn at different time intervals and centrifuged. The clear supernatant was used for refractive index (RI) to calculate percent solubilization and analyzed for sugar composition by HPLC.

TABLE 7

Product profile of fungal glucoamylases on starch during liquefaction.

| Enzymes | Dose:/gds | Hr | % Solubility | % DP1 | % DP2 | % DP3 | % HS |
|---|---|---|---|---|---|---|---|
| SPEZYME XTRA | 10 AAU | 5 | 52.5% | 73.05 | 13.20 | 1.55 | 12.20 |
| OPTIMAX L-1000 | 0.15 ASPU | 20.5 | 72.5% | 93.00 | 2.38 | 1.86 | 2.76 |
| AfGA1TR | 0.047 mg | 29 | 76.2% | 94.10 | 2.21 | 1.55 | 2.13 |
|   |   | 44.5 | 82.0% | 95.14 | 2.16 | 1.16 | 1.54 |
|   |   | 52 | 83.5% | 95.43 | 2.20 | 1.02 | 1.36 |
|   |   | 68 | 86.1% | 95.75 | 2.36 | 0.81 | 1.08 |

Table 7 shows that AfGA1TR was able to reach >95.5% DP1 in 68 hours using granular starch in presence of alpha-amylase and PU, where granular starch was 86% solubilized.

Example 10: Effect of Residual Alpha-Amylase Activity on DP3 Level

Figures 5A, 5B:
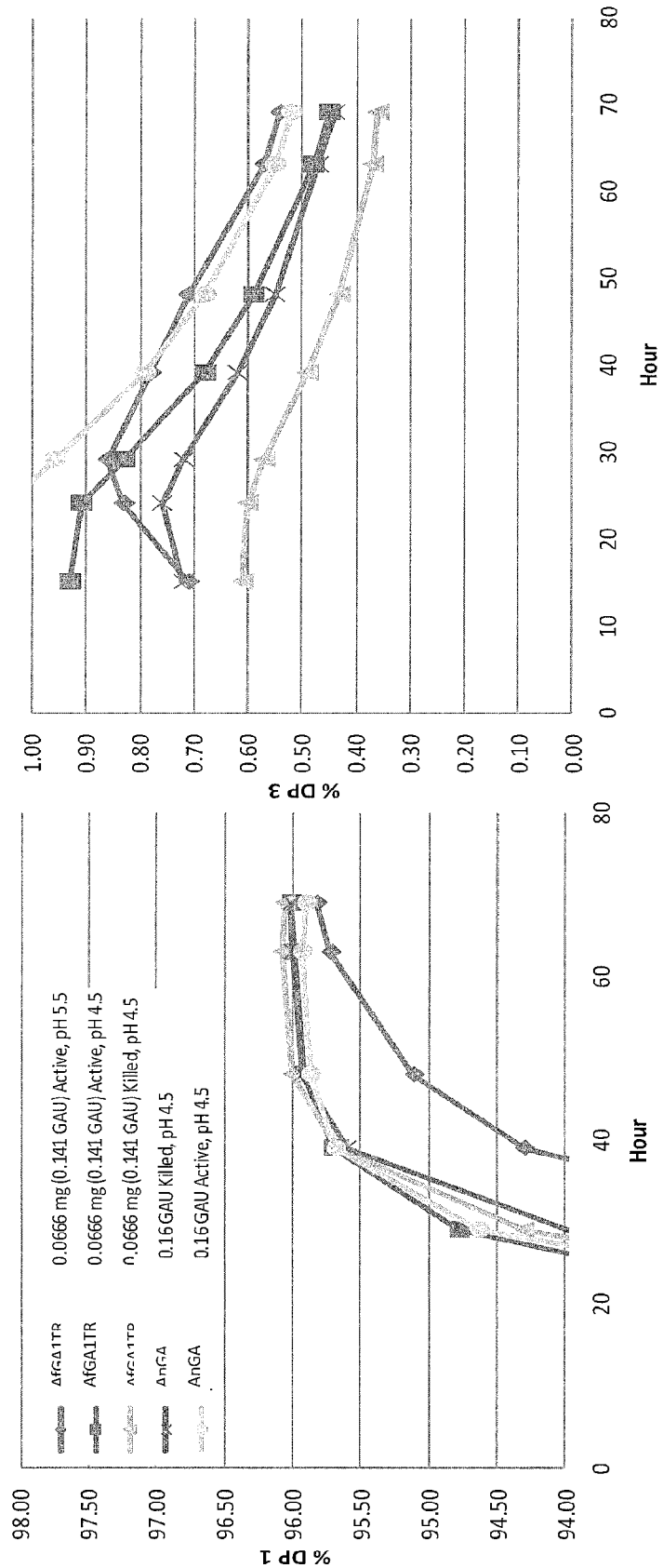
FIGS. 5A-B depict AfGA1TR and AnGA glucoamylase activity assayed by the release of glucose from 35% dry solid starch at pH 4.5 and 5.0.

The effect of single pH (5.5) and the effect of residual alpha-amylase activity at pH 4.5 on both DP1 and DP3 with AfGA1TR by adding 0.066 KG/MTds of LIQUOZYME® Supra (NZ) back to alpha-killed starch liquefact was analyzed. 0.066 mg/gds of AfGA1TR was blended with 0.25 ASPU/gds of OPTIMAX® L-1000 (pullulanase) and 0.1SS U/gds of AkAA. Table 8 and FIG. 5 disclose profiles of oligosaccharides saccharified by AfGA1TR and OPTIMAX® 4060 VHP (an AnGA/pullanase blend).

TABLE 8

Product profile of fungal glucoamylase on liquefied starch.

| Sugar composition at 48 hours | % DP1 | % DP2 | % DP3 | % HS |
|---|---|---|---|---|
| AfGA1TR triple 0.066 mg (0.141GAU), Active, pH 5.5 | 95.12 | 1.99 | 0.71 | 2.19 |
| AfGA1TR triple 0.066 mg (0.141GAU), Active, pH 4.5 | 95.92 | 2.19 | 0.59 | 1.30 |
| AfGA1TR triple 0.066 mg (0.141GAU), Killed, pH 4.5 | 96.00 | 2.26 | 0.43 | 1.31 |
| OPTIMAX ® 4060 VHP 0.16GAU, Killed, pH 4.5 | 95.93 | 2.27 | 0.55 | 1.25 |
| OPTIMAX ® 4060 VHP 0.16GAU, Active, pH 4.5 | 95.86 | 2.27 | 0.68 | 1.18 |

AfGA1TR triple blend showed significant loss in the rate of saccharification at pH 5.5 compared to pH 4.5 possibly due to unfavorable pH to OPTIMAX® L-1000 but was able to achieve >95.5% DP1 in 48 hours. Both AfGA1TR and OPTIMAX® 4060 VHP were a bit negatively affected by residual alpha-amylase activity to maximize glucose yield because of higher DP3 as expected. In the case of alpha-amylase killed liquefact, AfGA1TR resulted in significantly lower DP3 than OPTIMAX® 4060 VHP by 0.1%. Levels of AfGA1TR with alpha-amylase active liquefact were as low as the one of OPTIMAX® 4060 VHP with alpha-"killed" liquefact.

Example 11: Comparison of AfGA1TR with Wild-Type Aspergillus fumigatus Glucoamylase Starch liquefact was prepared to have 34% dry solids by diluting with water and the saccharification was carried out using the 2 different glucoamylases; 1) AfGA1TR at 0.067 mg/gds starch and 2) purified protein of wild-type AfGA (expressed in Aspergillus fumigatus) from GLUCOTEAM DB (Nagase Co. & Ltd., Japan) at 0.065 mg/gds at pH 4.4 and 60° C. In addition, pullulanase (PU) and acid-stable alpha-amylase, GC626® (AkAA) at 0.14 ASPU/gds and 0.9 SSU/gds, respectively, were dosed along with each glucoamylase. Samples were taken at different intervals of time and analyzed for sugar composition by HPLC.

Table 9 showed that AfGA1TR resulted in >95.5% DP1 in 48 hours, whereas commercial Aspergillus fumigatus took longer saccharification time. Both glucoamylases were able to reach >96% DP1 with DP2 less than 3%.

TABLE 9

Product profile of fungal glucoamylase blends on liquefied starch.

| Enzymes | Dose:/gds | Hr | % DP1 | % DP2 | % DP3 | % HS |
|---|---|---|---|---|---|---|
| AFGA1TR | 0.067 mg | 15 | 86.62 | 4.60 | 0.76 | 8.02 |
| OPTIMAX L-1000 | 0.14 ASPU | 26 | 94.78 | 2.11 | 0.77 | 2.34 |
| GC626 ® | 0.9 SSU | 39 | 96.12 | 2.07 | 0.55 | 1.26 |
| | | 48 | 96.27 | 2.26 | 0.45 | 1.02 |
| | | 63 | 96.22 | 2.61 | 0.34 | 0.83 |
| | | 71 | 96.16 | 2.77 | 0.31 | 0.76 |
| Wild-type AfGA | 0.065 mg | 16 | 75.43 | 10.45 | 0.84 | 13.28 |
| OPTIMAX L-1000 | 0.14 ASPU | 24 | 87.33 | 4.87 | 0.93 | 6.87 |
| GC626 ® | 0.9 SSU | 40 | 95.11 | 2.05 | 0.89 | 1.95 |
| | | 48 | 95.81 | 1.93 | 0.79 | 1.47 |
| | | 64 | 96.16 | 2.09 | 0.61 | 1.14 |
| | | 72 | 96.21 | 2.19 | 0.55 | 1.05 |

Example 12: Solubilization and Hydrolysis of Granular Starch by Enzyme Blend Containing Alpha-Amylase, Pullulanase and Aspergillus fumigatus GAs In a typical example, granular corn starch slurry having 35% dry solid starch in distilled water was prepared and the pH was adjusted to pH 5.0 using sodium hydroxide. Ten AAU/gds of SPEZYME® XTRA and purified protein of AfGA1TR or wild-type Aspergillus fumigatus GA (AfGA) from GLUCOTEAM DB (Nagase Co. & Ltd., Japan) were added along with 0.15 ASPU/gds of OPTIMAX® L-1000 to the starch slurry. Then, the starch slurry was kept in a water bath maintained at 60° C. with constant stirring. An aliquot was withdrawn at different time intervals and centrifuged. The clear supernatant was used for refractive index (RI) to calculate percent solubilization and analyzed for sugar composition by HPLC. Table 10 shows that both Aspergillus fumigatus glucoamylases were able to reach >95.5% DP1 by 68 hours using granular starch in presence of alpha-amylase and PU, where granular starch was >86% solubilized.

TABLE 10

Effect of alpha-amylase and pullulanase on granular starch solubilization

| Enzymes | Dose:/gds | Hr | % Solubility | % DP1 | % DP2 | % DP3 | % HS |
|---|---|---|---|---|---|---|---|
| SPEZYME XTRA | 10 AAU | 5 | 52.5% | 73.05 | 13.20 | 1.55 | 12.20 |
| OPTIMAX L-1000 | 0.15 ASPU | 20.5 | 72.5% | 93.00 | 2.38 | 1.86 | 2.76 |
| AfGA1TR | 0.047 mg | 29 | 76.2% | 94.10 | 2.21 | 1.55 | 2.13 |
| | | 44.5 | 82.0% | 95.14 | 2.16 | 1.16 | 1.54 |
| | | 52 | 83.5% | 95.43 | 2.20 | 1.02 | 1.36 |
| | | 68 | 86.1% | 95.75 | 2.36 | 0.81 | 1.08 |

TABLE 10-continued

Effect of alpha-amylase and pullulanase on granular starch solubilization

| Enzymes | Dose:/gds | Hr | % Solubility | % DP1 | % DP2 | % DP3 | % HS |
|---|---|---|---|---|---|---|---|
| SPEZYME XTRA | 10 AAU | 15 | 72.3% | 87.15 | 4.92 | 2.25 | 5.68 |
| OPTIMAX L-1000 | 0.14 ASPU | 25 | 78.7% | 91.93 | 2.68 | 2.15 | 3.24 |
| Wild-type AfGA | 0.075 mg | 39 | 86.0% | 94.24 | 2.00 | 1.70 | 2.06 |
| | | 50 | 87.3% | 94.84 | 1.96 | 1.45 | 1.75 |
| | | 64 | 91.5% | 95.42 | 2.04 | 1.15 | 1.39 |
| | | 73 | 92.1% | 95.62 | 2.12 | 1.01 | 1.25 |

Example 13: Expression and Purification of AfGA2TR

The nucleic acid sequence for the AfGA2 gene (NCBI Reference Sequence DS499595 from 145382 to 147441) was mined from *Aspergillus fumigatus* A1163, and the amino acid sequence of the hypothetical protein encoded by the AfGA2 gene was found in the NCBI Databases (NCBI Accession No. EDP53734). The nucleotide sequence of the AfGA2 gene from *Aspergillus fumigatus* A1163 was optimized and synthesized by Generay (Generay Biotech Co., Ltd, Shanghai, China).

Figure 9:
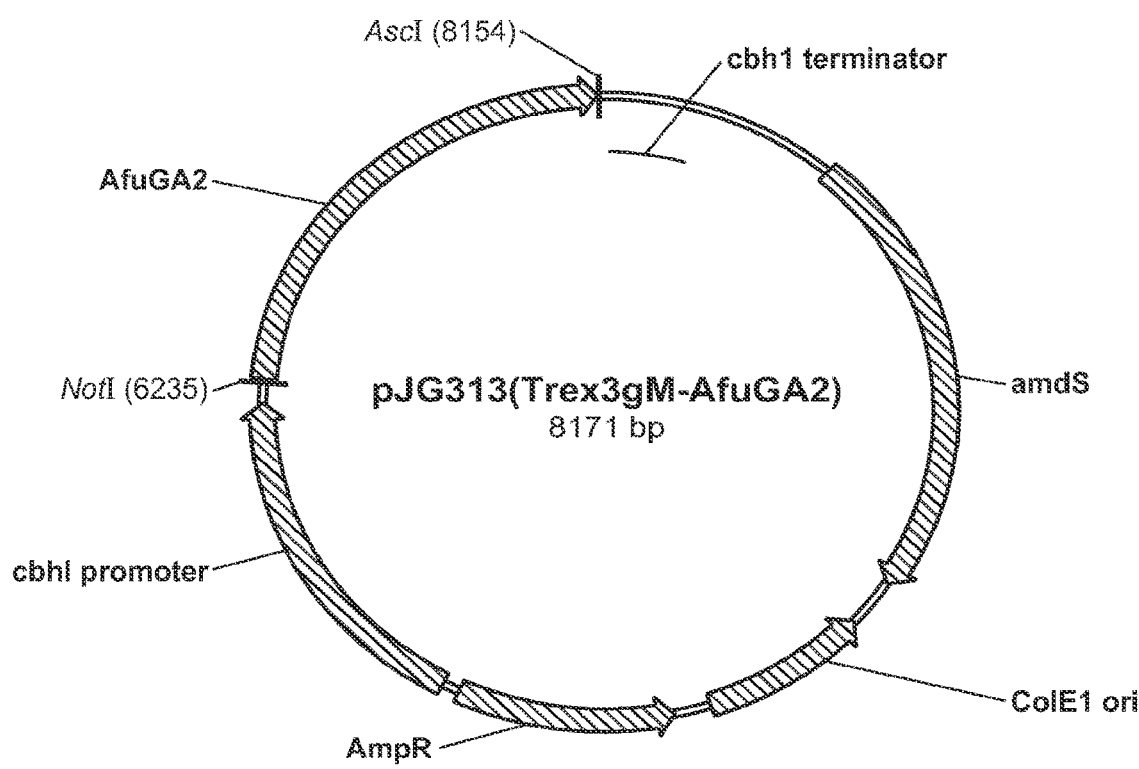
FIG. 9 depicts a map of a pJG313 expression vector comprising a polynucleotide that encodes an AfGA2 polypeptide, pJG313(Trex3gM-AfGA2).

The DNA sequence of AfGA2 was optimized for its expression in *Trichoderma reesei*, then synthesized and inserted into the pTrex3gM expression vector (described in U.S. Published Application 2011/0136197 A1) by Generay (Generay Biotech Co., Ltd, Shanghai, China), resulting in pJG313 (FIG. 9).

The plasmid pJG313 was transformed into a quad-deleted *Trichoderma reesei* strain (described in WO 05/001036) using biolistic method (Te'o et al., *J. Microbiol. Methods* 51:393-99, 2002). Transformants were selected on a medium containing acetamide as a sole source of nitrogen (acetamide 0.6 g/L; cesium chloride 1.68 g/L; glucose 20 g/L; potassium dihydrogen phosphate 15 g/L; magnesium sulfate heptahydrate 0.6 g/L; calcium chloride dihydrate 0.6 g/L; iron (II) sulfate 5 mg/L; zinc sulfate 1.4 mg/L; cobalt (II) chloride 1 mg/L; manganese (II) sulfate 1.6 mg/L; agar 20 g/L; pH 4.25). Transformed colonies (about 50-100) appeared in about 1 week. After growth on acetamide plates, transformants were picked and transferred individually to acetamide agar plates. After 5 days of growth on acetamide plates, transformants displaying stable morphology were inoculated into 200 µl Glucose/Sophorose defined media in 96-well microtiter plates. The microtiter plate was incubated in an oxygen growth chamber at 28° C. for 5 days. Supernatants from these cultures were used to confirm the protein expression by SDS-PAGE analysis and assay for enzyme activity. The stable strains were subsequently grown in a 7 L fermentor in a defined medium containing 60% glucose-sophorose feed. Glucose/Sophorose defined medium (per liter) consists of $(NH_4)_2SO_4$ 5 g, PIPPS buffer 33 g, Casamino Acids 9 g, $KH_2PO_4$ 4.5 g, $CaCl_2$ (anhydrous) 1 g, $MgSO_4 \cdot 7H_2O$ 1 g, pH to 5.5 adjusted with 50% NaOH with Milli-Q $H_2O$ to bring to 966.5 mL. After sterilization, the following were added: 26 mL 60% Glucose/Sophrose, and 400× *T. reesei* Trace Metals 2.5 mL.

The protein, AfGA2TR, was purified via two steps of chromatography. Amonium sulfate was added to 600 mL fermentation broth until the final concentration of amonium sulfate reaches 1 M. The sample was loaded onto a 50 mL hydrophobic interaction chromatography Phenyl HP column pre-equilibrated with 20 mM sodium phosphate pH 7.0 containing 1 M Amonium sulfate (buffer A). The column was washed with a linear salt gradient from 1 to 0 M amonium sulfate. The active fractions were pooled and applied to affinity chromatography. The sample after hydrophobic interaction chromatography was exchanged into 25 mM pH4.3 sodium acetate buffer (buffer B) and loaded onto β-cyclodextrin coupled Sepharose 6B column pre-equilibrated with buffer B. The target protein was eluted by 25 mM pH 4.3 sodium acetate with 10 mM α-cyclodextrin (Buffer C). The eluant was concentrated by using a 10K Amicon Ultra-15 device. The final product was above 98% pure and stored in 40% glycerol at −80° C. for further studies.

Example 14: Glucoamylase Activity of AfGA2TR

AfGA2TR belongs to the glycosyl hydrolase 15 family (GH15, CAZy number). The glucoamylase activity of AfGA2TR was measured using 1% w/w soluble starch (Sigma 59765) as a substrate. The assay was performed in 50 mM sodium acetate buffer pH 5.0 at 50° C. for 10 minutes. The rate of glucose release was measured using the glucose oxidase/peroxidase (GOX/HRP) technique disclosed in Example 3. Glucose was quantified as the rate of oxidation of 2,2'-azino-bis 3-ethylbenzothiazoline-6-sulfonic acid (ABTS) via excess coupled GOX/HRP enzymes. The enzyme activity was calculated based on a glucose standard curve. In this assay, one glucoamylase unit is defined as the amount of enzyme required to generate 1 µmol of glucose per minute under the conditions of the assay. The specific activity towards soluble starch of purified AfGA2TR was determined to be 214 units/mg using the above method.

Example 15: pH Profile of AfGA2TR

Figure 10:
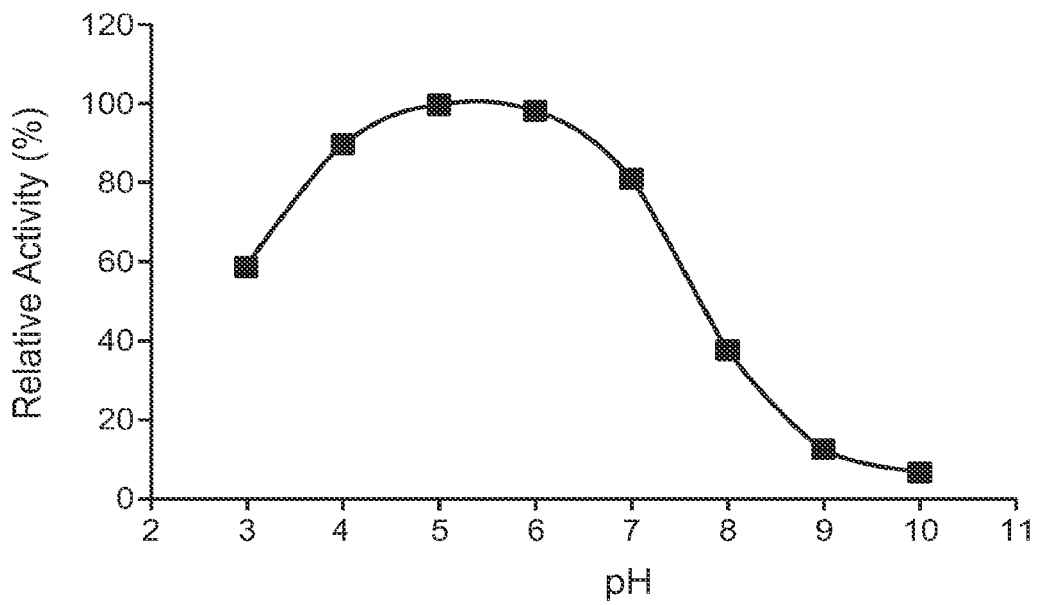
FIG. 10 depicts the dependence of glucoamylase (relative units) AfGA2TR expressed in *Trichoderma reesei* on pH. Glucoamylase activity was assayed by the release of glucose from soluble starch substrate at 50° C.

The effect of pH (from 3.0 to 10.0) on AfGA2TR activity was monitored by following the ABTS assay protocol as described in Example 3. Buffer working solutions consisted of the combination of glycine/sodium acetate/HEPES (250 mM), with pH variation from 3.0 to 10.0. Substrate solutions were prepared by mixing soluble starch (1% in water, w/w) with 250 mM buffer solution at a ratio of 9:1. Enzyme working solutions were prepared in water at a certain dose (showing signal within linear range as per dose response curve). All the incubations were done at 50° C. for 10 min using the same protocol as described for gluco-amylase activity assay in Example 3. Enzyme activity at each pH was reported as relative activity towards enzyme activity at optimum pH. The pH profile of AfGA2TR is shown in FIG. 10. AfGA2TR was found to have an optimum pH at about 5.3, and retain greater than 70% of maximum activity between pH 3.3 and 7.3.

Example 16: Temperature Profile of AfGA2TR

Figure 11:
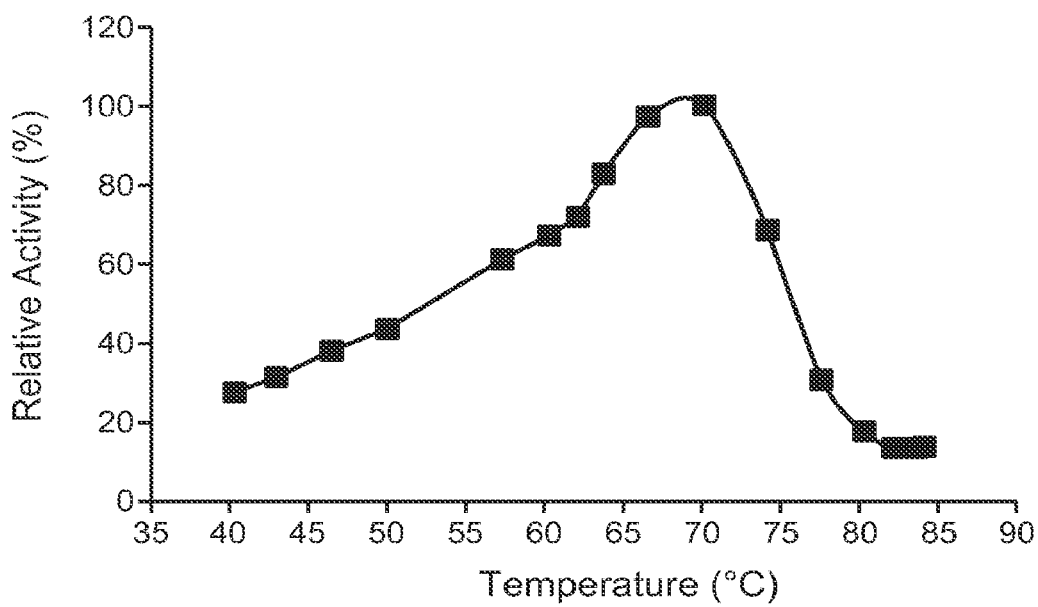
FIG. 11 depicts the dependence of glucoamylase activity (relative units) of AfGA2TR expressed in *Trichoderma reesei* on temperature. Glucoamylase activity was assayed by the release of glucose from soluble starch substrate at pH 5.0.

The effect of temperature (from 40° C. to 84° C.) on AfGA2TR activity was monitored by following the ABTS assay protocol as described in Example 3. Substrate solutions were prepared by mixing 9 mL of soluble starch (1% in water, w/w) and 1 mL of 0.5 M buffer (pH 5.0 sodium acetate) into a 15-mL conical tube. Enzyme working solutions were prepared in water at a certain dose (showing signal within linear range as per dose response curve). Incubations were carried out at temperatures from 40° C. to 84° C., respectively, for 10 min. After incubation, the activities were determined following the same protocol as described for glucoamylase activity assay in Example 3. The activity was reported as relative activity towards the enzyme activity at optimum temperature. The temperature profile of AfGA2TR is shown in FIG. 11. AfGA2TR was found to have an optimum temperature of 69° C., and retain greater than 70% of maximum activity between 61° C. and 74° C.

Example 17: Thermostability of AfGA2TR

Figure 12:
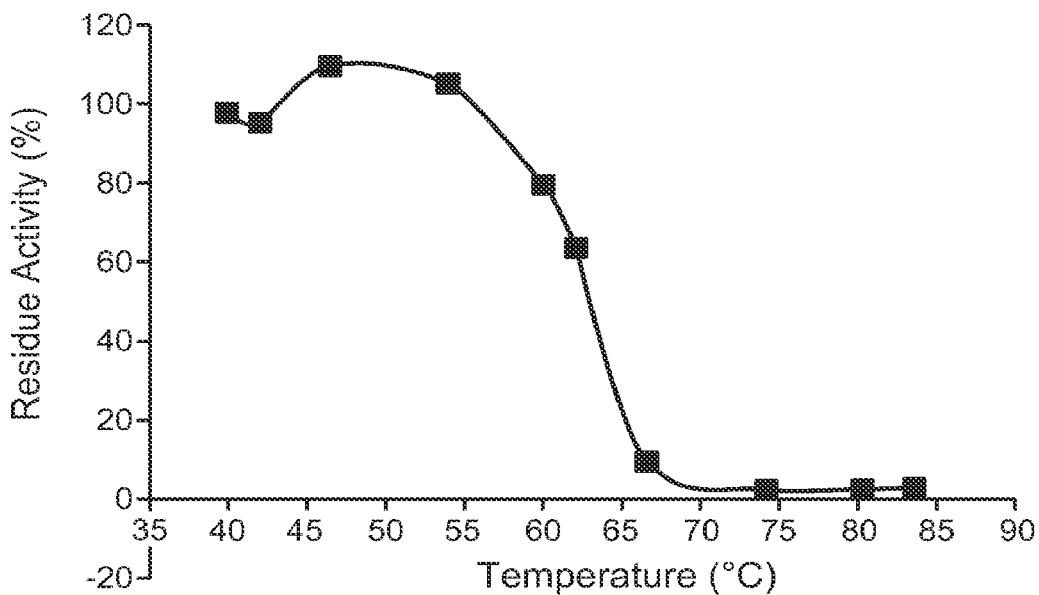
FIG. 12 depicts the thermostability of AfGA2TR in 50 mM sodium acetate buffer at pH 5.0. The enzyme was incubated at desired temperature for 2 hours in a thermocycler prior to addition to soluble starch substrate.
Figure 13:
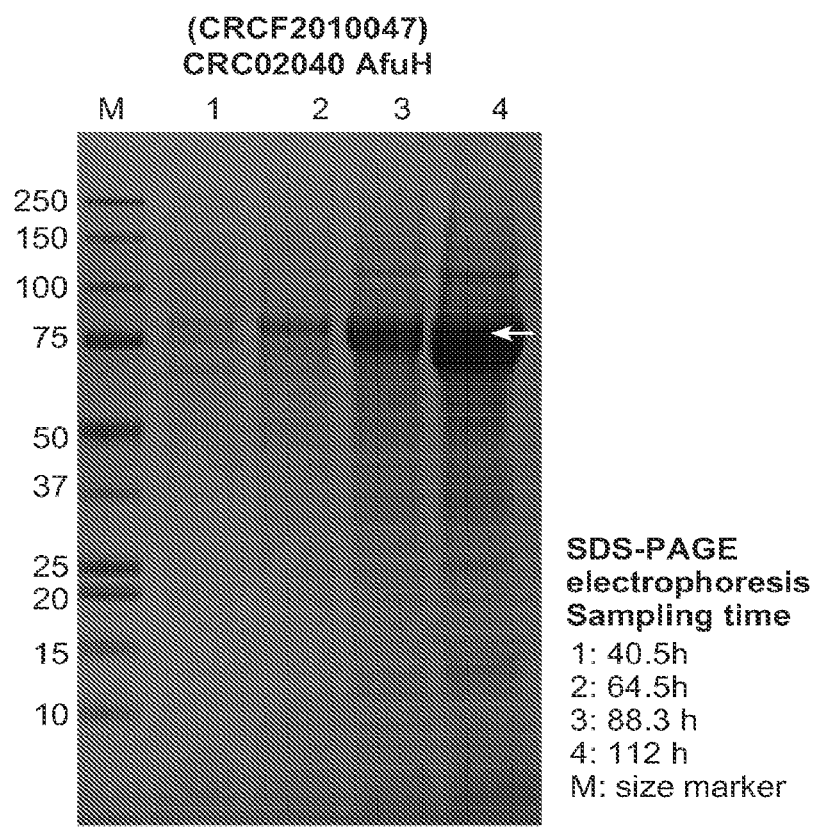
FIG. 13 depicts an SDS gel of AfGA1TR expressed in *T. reesei*. Column M contains a protein molecular weight (MW) ladder in kDa. Columns 1-4 represent samples from *T. reesei* fermentation producing AfGATR with elapsed fermentation times of 40.5 hours, 64.5 hours, 88.3 hours and 112 hours, respectively. The bands labeled with an arrow at 75 kDa are AfGA1TR.

The thermostability of AfGA2TR was determined in 50 mM sodium acetate buffer pH 5.0. The enzyme was incubated at desired temperature for 2 hours in a PCR machine prior to addition into substrate. The remaining activity of the samples was measured as described in Example 3. The activity of the sample kept on ice was defined as 100% activity. As shown in FIG. 12, at temperature lower than 63° C., AfGA2TR retained over 50% activity during a 2-hour incubation period.

Example 18: Comparison of AfGA1TR with AfGA2TR

Starch liquefact was prepared to have 34% dry solids by diluting with water and the saccharification was carried out using the 2 different glucoamylases; 1) AfGA1TR at 0.06 mg/gds starch and 2) purified protein of AfGA2TR at 0.06 mg/gds at pH 4.4 and 60° C. In addition, pullulanase (OPTIMAX® L-1000) and acid-stable alpha-amylase, GC626® (AsAA) at 0.14 ASPU/gds and 0.9 SSU/gds, respectively, were dosed along with each glucoamylase to enhance glucose production. Samples were taken at different intervals of time and analyzed for sugar composition by HPLC.

TABLE 11

Product profile of AfGA1TR and AfGA2TR blends on liquefied starch.

| Enzymes | Dose:/gds | Hr | % DP1 | % DP2 | % DP3 | % HS |
|---|---|---|---|---|---|---|
| AFGA1TR | 0.06 mg | 16 | 82.99 | 6.76 | 1.14 | 9.11 |
| OPTIMAX® L-1000 | 0.14 ASPU | 24 | 91.65 | 3.30 | 1.21 | 3.84 |
| GC626® | 0.9 SSU | 40 | 95.32 | 2.33 | 0.93 | 1.42 |
|  |  | 48 | 95.66 | 2.39 | 0.79 | 1.16 |
|  |  | 64 | 95.73 | 2.71 | 0.64 | 0.92 |
|  |  | 72 | 95.64 | 2.87 | 0.62 | 0.87 |
| AfGA2TR | 0.06 mg | 16 | 86.40 | 4.32 | 1.05 | 8.23 |
| OPTIMAX® L-1000 | 0.14 ASPU | 24 | 93.34 | 2.34 | 1.05 | 3.27 |
| GC626® | 0.9 SSU | 40 | 95.68 | 2.17 | 0.78 | 1.37 |
|  |  | 48 | 95.91 | 2.28 | 0.67 | 1.14 |
|  |  | 64 | 95.93 | 2.62 | 0.55 | 0.90 |
|  |  | 72 | 95.88 | 2.77 | 0.51 | 0.84 |

Table 11 showed that both glucoamylases resulted in >95.5% DP1 in 48 hours with a slightly faster saccharification using AfGA2TR.

Although the compositions and methods of making and using has been described in detail with reference to examples above, it is understood that various modifications can be made without departing from the spirit these compositions and methods, and would be readily known to the skilled artisan.

All cited patents and publications referred to in this application are herein incorporated by reference in their entirety for all purposes.

SEQUENCE LISTING

```
SEQ ID NO: 1-AfGA1 precursor
MPRLSYALCALSLGHAAIAAPQLSARATGSLDSWLGTETTVALNGILANIGADGAYAKSAKPGIIIASPSTSEPDYY
YTWTRDAALVTKVLVDLERNGNLGLQKVITEYVNSQAYLQTVSNPSGGLASGGLAEPKYNVDMTAFTGAWGRPQRDG
PALRATALIDEGNWLIDNGYSSYAMNNIWPIVRNDLSYVSQYWSQSGFDLWEEVNSMSFFTVAVQHRALVEGSTFAK
RVGASCSWCDSQAPQILCYMQSFWTGSYINANTGGGRSGKDANTVLASIHTFDPEAGCDDTTFQPCSPRALANHKVY
TDSFRSVYAINSGIPQGAAVSAGRYPEDVYYNGNPWFLTTLAAAEQLYDAIYQWKKIGSISITSTSLAFFKDIYSSA
AVGTYASSTSTFTDIINAVKTYADGYVSIVQAHAMNNGSLSEQFDKSSGLSLSARDLTWSYAAFLTANMRRNGVVPA
PWGAASANSVPSSCSMGSATGTYSTATATSWPSTLTSGSPGSTTTVGTTTSTTSGTAAETACATPTAVAVTFNEIAT
TTYGENVYIVGSISELGNWDTSKAVALSASKYTSSNNLWYVSVTLPAGTTFEYKYIRKESDGSIVWESDPNRSYTVP
AACGVSTATENDTWQ SEQ ID NO: 2-AfGA2 precursor
MPRLSYALCALSLGHAAIAAPQLSARATGSLDSWLGTETTVALNGILANIGADGAYAKSAKPGIIIASPSTSEPDYY
YTWTRDAALVTKVLVDLERNGNLGLQKVITEYVNSQAYLQTVSNPSGGLASGGLAEPKYNVDMTAFTGAWGRPQRDG
PALRATALIDEGNWLIDNGYSSYAMNNIWPIVRNDLSYVSQYWSQSGFDLWEEVNSMSFFTVAVQHRALVEGSTFAK
RVGASCSWCDSQAPQILCYMQSFWTGSYINANTGGGRSGKDANTVLASIHTFDPEAGCDDTTFQPCSPRALANHKVY
TDSFRSVYAINSGIPQGAAVSAGRYPEDVYYNGNPWFLTTLAAAEQLYDAIYQWKKIGSISITSTSLAFFKDIYSSA
AVGTYASSTSTFTDIINAVKTYADGYVSIVQAHAMNNGSLSEQFDKSSGLSLSARDLTWSYAAFLTANMRRNGVVPA
PWGAASANSVPSSCSMGSATGTYSTATATSWPSTLTSGSPGSTTTVGTTTSTTSGTATETACATPTAVAVTFNEIAT
TTYGENVYIVGSISELGNWDTSKAVALSASKYTSSNNLWYVSVTLPAGTTFEYKYIRKESDGSIVWESDPNRSYTVP
AACGVSTATENDTWR SEQ ID NO: 3-Nf_NRRL_181_GA
MPRLSYALCALSLGHAAIAAPQLSPRATGSLDSWLATESTVSLNGILANIGADGAYAKSAKPGIIIASPSTSDPDYY
YTWTRDAALVTKVLVDLERNGNLGLQKVITEYVNSQAYLQTVSTPSGGLSSGGLAEPKYNVDMTAFTGAWGRPQRDG
PALRATALIDEGNWLIDNGYSSYAMNNIWPIVRNDLSYVSQYWSQSGFDLWEEVNSMSFFTVAVQHRALVEGSTFAK
RVGASCSWCDSQAPQILCYMQSFWTGSYINANTGGGRSGKDANTVLASIHTFDPEAGCDDTTFQPCSPRALANHKVY
TDSFRSVYAINSGIPQGVAVSAGRYPEDVYYNGNPWFLTTLAAAEQLYDAIYQWKKIGSISITSTSLAFFKDIYSSV
AVGTYASSSSTFTAIIDAVKTYADGYVSIVEAEAMTNGSLSEQFDKSSGMSLSARDLTWSYAALLTANMRRNGVVPA
PWGAASANSVPSSCSMGSATGTYSTATATSWPSTLTSGSPSDTTSGTTPGTTTTTSACTTPTSVAVTFDEIATTTYG
ENVYTIGSISQLGSWDTSKAVPLSSSKYTSSNNLWYVTINLPAGTTFEYKYIRKESDGSIEWESDPNRSYTVPSACG
VSTATEKDTWR
```

SEQUENCE LISTING

SEQ ID NO: 4-Ts_ATCC0_10500_GA
MTRLSSVLCALAALGQTALAAPGLSPRASTSLDAWLATETTVSLSGILANIGADGAYSKSAKPGVVIASPSTDNPNY
YYTWTRDSALTLKVLIDLERNGNLGLQTVIEEYVNAQAYLQTVSNPSGDLSSGAGLAEPKENVDMSAFTGSWGRPQR
DGPALRAIALIDFGNWLIENGYTSLAANNIWPIVRNDLSYVAQYWSQSGFDLWEEVNSMSFFTVANQHRSLVEGSTF
AAKVGASCSWCDSQAPQILCYMQTFWTGSYMNANTGGGRSGKDANTVLTSIATFDPEATCDDVTFQPCSPRALANHK
VYTDSFRSVYGLNSGIAEGVAVAVGRYPEDSYYNGNPWFLSNLAAAEQLYDAIYQWNKIGSITITSTSLAFFKDVYS
SAAVGTYASGSSAFTSIINAVKTYADGYISVVQSHAMNNGSLSEQFDKNTGAELSARDLTWSYAALLTANMRRNGVV
PPSWGAASATSIPSSCTTGSAIGTYSTPTATSWPSTLTSGTGSPGSTTSATGSVSTSVSATTTSAGSCTTPTSVAVT
FDEIATTSYGENVYIVGSISQLGSWNTANAIALSASKYTTSNNLWYVTINLPAGTTFQYKYIRKESDGTVKWESDPN
RSYTVPSACGVSTATENDTWR

SEQ ID NO: 5-Pm_ATCC_18224_GA
MTFSRLSSSVLCALAALGHNALAAPQFSPRATVGLDAWLASETTFSLNGILANIGSSGAYSASAKPGVVIASPSTNN
PNYYYTWTRDSALTLKVLIDLFGNGNLSLQTVIEEYINAQAYLQTVSNPSGDLSSGAGLAEPKYNVDMSPFTGGWGR
PQRDGPALRAIALIEFGNWLIDNGYSSYAMNNIWPIVRNDLSYVSQYWSQSGFDLWEEVNSMSFFTVANQHRALVQG
STFAARVGASCSWCDSQAPQILCYMQTFWTGSYINANTGGGRSGKDSNTVLTTIHTFDPEATCDDVTFQPCSPRALA
NHKVYTDSFRSIYGVNSGIAQGVAVSVGRYPEDSYYGGNPWFLSNLAAAEQLYDAIYQWNKIGSITITSTSLAFFKD
VYSSAAVGTYASGSTAFTSIISAVKTYADGYVSIVQGHAAANGSLSEQFDRNSGVEISARDLTWSYAALLTANLRRN
GVMPPSWGAASANSVPSSCSMGSATGTYSTPTATAWPSTLTSATGIPVTTSATASVTKATSATSTTTSATTCTTPTS
VAVTFDEIATTTYGENVFIVGSISQLGSWDTSKAIALSASQYTSSNHLWFATLSLPAGTTFQYKYIRKESNGSIVWE
SDPNRSYTVPSGCGVSTATENDTWR

SEQ ID NO: 6-An_FGSC_A4_GA
MPTTILKITLFPLIDSIFSVQLSPVRIAMLTLSKVLPVLALSHAVAAAPQLSARATASLNTWLSTEASFALDGILTN
IGANGAYAKTAKAGADYYTWTRDAALTVKVLVDLFHNGDLSLQTILEEYTNSQAYLQTVSNPSGGLASGGLAEPKFY
VDMTAFTGSWGRPQRDGPALRATTLIGFGNWLIDNGYSSASNNIWPIVRNDLTYVAQYWSKSGYDLWEEVNSMSFF
TVAVQHRALVEGSTFAHRVGASCPWCDSQAPQILCYMQNFWTGSYINANTGGGRSGKDANTVLASIHTFDPDAACDD
ITFQPCSSRALANHKVYTDSFRSVYSLNTGIAQGVAVAAGRYPEDSYYNGNPWFLTTLAAAEQLYDAIYQWQKARSI
SITSTSLAFFKDIYSSAAVGTYASGSSAFTAIIDAVKTYADGYVSIVKAHAMANGSLSEQFDKTYGTCVSARDLTWS
YAALLTASMRRNGVVPPSWDAASANTLPSSCSTGSATGTYSTATVTTWPSTLTSGSASATTTIMATSTATSSSTTTS
TTTACTTPSTVAVTFNVIATTTYGENVYIVGSISQLGNWDTGSAVALSASKNTSSNNLWYVDINLPGGTAFEYKYIR
KETDGSIVWESDPNRSYTVPSSCGVSTATESDTWRCTLETQSVRN

SEQ ID NO: 7- AfGA1 and AfGA2 CBM
FNEIATTTYGENVYIVGSISELGNWDTSKAVALSASKYTSSNNLWYVSVTLPAGTTFEYKYIRKESDGSIVWESDPN
RSYTVPAACGVSTATENDTW SEQ ID NO: 8- AfGA1 gene of pTrex3gM-AfGA1
ATGCCTCGCCTTTCCTACGCGCTCTGTGCGCTGTCTCTCGGGCATGCTGCTATTGCAGCTCCTCAGTTATCCGCTCG
TGCTACCGGCAGCTTGGACTCCTGGTTGGGTACTGAGACCACCGTTGCGCTCAATGGTATTCTGGCCAACATCGGTG
CCGACGGTGCTTATGCGAAGAGCGCTAAGCCTGGCATAATCATTGCCAGTCCGAGCACCAGCGAACCAGACTGTGAG
AACCTTCCTGAACTGGCCCTGTCCGGCAGTCATTGACCTCGGTAGACTACTATACCTGGACGAGAGATGCTGCTCTC
GTCACGAAAGTCCTGGTCGACCTCTTCCGCAACGGCAACCTGGGTCTGCAGAAGATCATTACCGAATACGTCAACTC
TCAGGCGTACTTGCAGACCGTGTCTAATCCGTCGGGTGGTCTTGCGAGCGGAGGTCTCGCGGAGCCTAAGTACAACG
TCGACATGACGGCCTTTACCGGAGCCTGGGGTCGTCCTCAGCGTGATGGTCCGGCTCTGCGGGCACCGCCCTCATC
GACTTTGGCAACTGGCTGATTGATGTTCTCCATACGAGCCCCAGGAAGCGTTGCTGACGTCTACAGGACAACGGCT
ACTCCAGCTATGCTGTCAACAACATCTGGCCCATTGTGCGCAACGACTTGTCCTACGTTTCTCAGTACTGGAGCCAG
AGTGGCTTTGGTGAGTCCCGACTCTCTGGAAGTTTACAACGTGCATCGATTCTGACAATTGAGATTCTACGTGACA
GATCTCTGGGAAGAAGTCAACTCCATGTCCTTCTTCACCGTCGCTGCTGTCCAGCACCGTGCCCTCGTGGAGGGAAGCAC
GTTCGCTAAACGGGTGGGAGCGTCGTGCTCGTGGTGTGACTCGCAGGCCCCCAGATCCTCTGCTACATGCAGAGTT
TCTGGACTGCTCGTATATCAACGCCAACACCGGTGGTGGCCGGTCCGGCAAGGATGCCAACACCGTCCTCGCCAGC
ATCCATACCTTCGACCCCGAAGCCGGCTGCGACGATACTACTTTCCAGCCCTGCTCTCCTCGGGCCCTTGCCAACCA
CAAGGTGTACACCGATTCGTTCCGCTCGGTCTACGCGATCAACTCCGGCATCCCACAGGGCGCTGCCGTTTCCGCTG
GCCGCTACCCCGAGGACGTCTACTACAACGGCAACCCTTGGTTCCTCACCACCCTCGCCGCTGCCGAGCAGCTCTAC
GACGCTATCTACCAGTGGAAGAAGATCGGTTCCATCAGCATCACCAGCACCTCCCTCGCCTTCTTCAAGGACATCTA
CAGCTCCGCCGCGGTCGGCACCTACGCCTCTAGCACCTCCACCTTCACGGACATCATCAACGCGGTCAAGACCTACG
CAGACGGCTACGTGAGCATCGTCCAGGCACACGCCATGAACAACGGCTCCCTTTCGGAGCAATTCGACAAGTCCTCT
GGGCTGTCCCTCTCCGCCCGCGATCTGACCTGGTCCTACGCCGCTTTCCTCACCGCCAACATGCGTCGTAACGGCGT
GGTGCCTGCCCCCTGGGGCGCGCCTCCGCCAACTCCGTCCCCTCGCTCTTGCTCCATGGGCTCGGCCACGGGCACCT
ACAGCACCGCGACAGCCACCTCCTGGCCCAGCACGCTGACCAGCGGCTCGCCAGGCAGCACCACCACCGTGGGCACC
ACGACCAGTACCACCTCTGGCACCGCCGCCGAGACCGCCTGTGCGACCCCTACCGCCGTGGCCGTCACCTTTAACGA
GATCGCCACCACCACCTACGGCGAGAATGTTTACATTGTTGGGTCCATCTCCGAGCTCGGGAACTGGGATACCAGCA
AAGCAGTGGCCCTGAGTGCGTCCAAGTATACCTCCAGCAATAACCTCTGGTACGTGTCCGTCACCCTGCCGGCTGGC
ACGACATTCGAGTACAAGTATATCCGCAAGGAAAGCGATGGCTCGATCGTGTGGGAGAGTGACCCCAACCGCTCGTA
TACGGTGCCGGCAGCTTGTGGAGTGTCTACTGCGACCGAGAATGATACTTGGCAGTGA SEQ ID NO: 9-AfGA1
GCGGCGGCCGCACCATGCCTCGCCTTTCCTACGC SEQ ID NO: 10-AfGA1
CCGGCGCGCCCTTATCACTGCCAAGTATCATTCTCG SEQ ID NO: 11-AfGA1 and AfGA2 signal peptide
MPRLSYALCALSLGHAAIA

SEQUENCE LISTING

```
SEQ ID NO: 12-AfGA1 Mature form
APQLSARATGSLDSWLGTETTVALNGILANIGADGAYAKSAKPGIIIASPSTSEPDYYYTWTRDAALVTKVLVDLFR
NGNLGLQKVITEYVNSQAYLQTVSNPSGGLASGGLAEPKYNVDMTAFTGAWGRPQRDGPALRATALIDEGNWLIDNG
YSSYAYNNIWPIVRNDLSYVSQYWSQSGFDLWEEVNSMSFFTVAVQHRALVEGSTFAKRVGASCSWCDSQAPQILCY
MQSFWTGSYINANTGGGRSGKDANTVLASIHTFDPEAGCDDTTFQPCSPRALANHKVYTDSFRSVYAINSGIPQGAA
VSAGRYPEDVYYNGNPWFLTTLAAAEQLYDAIYQWKKIGSISITSTSLAFFKDIYSSAAVGTYASSTSTFTDIINAV
KTYADGYVSIVQAHAMNNGSLSEQFDKSSGLSLSARDLTWSYAAFLTANMRRNGVVPAPWGAASANSVPSSCSMGSA
TGTYSTATATSWPSTLTSGSPGSTTTVGTTTSTTSGTAAETACATPTAVAVTFNEIATTTYGENVYIVGSISELGNW
DTSKAVALSASKYTSSNNLWYVSVTLPAGTTFEYKYIRKESDGSIVWESDPNRSYTVPAACGVSTATENDTWQ SEQ ID NO: 13-AfGA2 Mature form
APQLSARATGSLDSWLGTETTVALNGILANIGADGAYAKSAKPGIIIASPSTSEPDYYYTWTRDAALVTKVLVDLFR
NGNLGLQKVITEYVNSQAYLQTVSNPSGGLASGGLAEPKYNVDMTAFTGAWGRPQRDGPALRATALIDEGNWLIDNG
YSSYAYNNIWPIVRNDLSYVSQYWSQSGFDLWEEVNSMSFFTVAVQHRALVEGSTFAKRVGASCSWCDSQAPQILCY
MQSFWTGSYINANTGGGRSGKDANTVLASIHTFDPEAGCDDTTFQPCSPRALANHKVYTDSFRSVYAINSGIPQGAA
VSAGRYPEDVYYNGNPWFLTTLAAAEQLYDAIYQWKKIGSISITSTSLAFFKDIYSSAAVGTYASSTSTFTDIINAV
KTYADGYVSIVQAHAMNNGSLSEQFDKSSGLSLSARDLTWSYAAFLTANMRRNGVVPAPWGAASANSVPSSCSMGSA
TGTYSTATATSWPSTLTSGSPGSTTTVGTTTSTTSGTATETACATPTAVAVTFNEIATTTYGENVYIVGSISELGNW
DTSKAVALSASKYTSSNNLWYVSVTLPAGTTFEYKYIRKESDGSIVWESDPNRSYTVPAACGVSTATENDTWR SEQ ID NO: 14-AfGA2 gene of pTrex3gM-AfGA2
ATGCCTCGACTGAGCTACGCTCTCTGCGCTCTGTCCCTGGGTCACGCTGCCATCGCCGCTCCCCAACTGAGCGCCCG
AGCTACTGGCAGCCTCGATTCCTGGCTGGGCACTGAGACCACCGTTGCTCTGAACGGCATCCTCGCTAACATCGGCG
CTGATGGTGCCTATGCCAAGAGCGCTAAACCTGGCATCATCATCGCCAGCCCTAGCACCAGCGAGCCTGATTACTAC
TATACTTGGACCCGCGACGCTGCTCTGGTCACCAAGGTCCTCGTTGACCTGTTCCGCAATGGTAACCTGGGCCTCCA
GAAAGTCATTACCGAGTACGTCAACAGCCAAGCTTATCTGCAAACCGTTAGCAATCCCTCCGGTGGCCTCGCTTCCG
GCGGGCCTGGCCGAGCCCAAATACAACGTCGACATGACCGCCTTTACCGGTGCCTGGGGTCGCCCCCAGCGAGATGGC
CCTGCCCTGCGCGACCACCGCTCTCATCGACTTCGGCAACTGGCTGATCGACAACGGCTATTCCAGCTATGCTGTCAA
CAACATTTGGCCCATCGTCCGCAACGACCTGTCCTATGTTTCCCAATACTGGTCCCAGTCCGGTTTCGACCTCTGGG
AGGAGGTTAATTCCATGAGCTTTTTCACCGTCGCTGTCCAACATCGAGCTCTCGTCGAGGGCTCCACTTTCGCTAAG
CGCGTCGGCGCCAGCTGTTCCTGGTGCGATTCCCAGGCCCCTCAGATTCTGTGCTACATGCAGTCCTTTTGGACCGG
TAGCTATATCAATGCCAATACCGGCGGTGGTCGAAGCGGCAAGGACGCTAATACTGTTCTGGCTTCCATCCACACCT
TCGATCCCGAGGCCGGCTGTGATGATACTACCTTTCAGCCCTGCTCCCCTCGCGCTCTCGCCAACCATAAAGTTTAC
ACCGACAGCTTTCGCAGCGTTTACGCCATCAACTCCGGCATTCCTCAAGGCGCTGCTGTTTCCGCTGGTCGCTACCC
CGAGGACGTTTACTATAATGGCAACCCCTGGTTCCTCACTACTCTGGCTGCTGCTGAGCAGCTCTATGACGCTATCT
ACCAATGGAAGAAAATCGGCAGCATCAGCATTACTTCCACCTCCCTCGCCTTCTTCAAAGACATCTATAGCTCCGCT
GCCGTTGGCACTTATGCTTCCTCCACTAGCACTTTCACTGATATTATCAACGCTGTTAAAACCTACGCTGACGGCTA
CGTCAGCATCGTTCAAGCCCACGCTATGAACAACGGTTCCCTCTCCGAGCAGTTCGACAAGTCCAGCGGTCTGAGCC
TCAGCGCTCGCGACCTCACCTGGTCCTACGCCGCCTTCCTGACTGCCAACATGCGCCGAAACGGCGTCGTTCCTGCC
CCTTGGGGTGCCGCCAGCGCCAATTCCGTCCCCAGCAGCTGTAGCATGGGCTCCGCCACTGGTACCTACAGCACCGC
TACCGCTACTAGCTGGCCCAGCACCCTGACTAGCGGCTCCCCCGGTTCCACTACTACCGTCGGCACCACTACCTCCA
CCACTTCCGGTACTGCCACCGAGACTGCCTGTGCCACCCCTACCGCCGTCGCCGTTACCTTTAACGAGATTGCTACC
ACCACCTACGGCGAGAACGTCTACATCGTCGGTAGCATCTCCGAGCTCGGCAATTGGGACACTTCCAAGGCTGTCGC
CCTGTCCGCCTCCAAATATACTAGCAGCAACAACCTGTGGTATGTCTCCGTTACCCTGCCTGCTGGTACTACTTTTG
AGTACAAGTACATTCGCAAAGAGTCCGATGGCTCCATCGTTTGGGAGTCCGATCCCAACCGAAGCTACACCGTTCCC
GCTGCTTGTGGCGTCTCCACTGCTACTGAGAATGACACCTGGCGCTAA
```

What is claimed is:

1. A recombinant *Trichoderma reesei* (*T. reesei*) host cell expressing an AfGATR having at least 90% sequence identity to SEQ ID NO: 12 or 13, wherein the AfGATR is more thermostable than an AfGA having the same amino acid sequence of AfGATR and wherein the AfGA is expressed in an *A. fumigatus* host cell.

2. A recombinant AfGATR produced by culturing the host cell of claim 1 in a fermentation medium.

3. The recombinant AfGATR of claim 2, wherein said AfGATR has at least 70% activity at 74° C. at pH 5.0 over 10 min.

4. The recombinant AfGATR of claim 3, wherein said AfGATR is an *A. fumigatus* glucoamylase 1 polypeptide expressed in *T. reesei* (AfGA1TR).

5. The recombinant AfGA1TR of claim 4, wherein said AfGA1TR has at least 70% activity over a temperature range of 55° to 74° C. at pH 5.0 over 10 min.

6. The recombinant AfGA1TR of claim 5, wherein said AfGAT1R has an optimum temperature of about 68° C.

7. The recombinant AfGATR of claim 3, wherein said AfGATR is an *A. fumigatus* glucoamylase 2 polypeptide expressed in *T. reesei* (AfGA2TR).

8. The recombinant AfGA2TR of claim 7, wherein said AfGA2TR has at least 70% activity over a temperature range of 61° to 74° C. at pH 5.0 over 10 min.

9. The recombinant AfGA2TR of claim 8, wherein said AfGA2TR has an optimum temperature of about 69° C.

10. The recombinant AfGATR of claim 3, wherein said AfGATR comprises an amino acid sequence with at least 95% or 99% amino acid sequence identity to SEQ ID NO: 12.

11. The recombinant AfGATR of claim 10, wherein said AfGATR comprises SEQ ID NO: 12.

12. The recombinant AfGATR claim 3, wherein said AfGATR consists of an amino acid sequence with at least 99% amino acid sequence identity to SEQ ID NO: 12.

13. The recombinant AfGATR of claim 3, wherein said AfGATR comprises an amino acid sequence with at least 95% or 99% amino acid sequence identity to SEQ ID NO: 13.

14. The recombinant AfGATR of claim 13, wherein said AfGATR comprises SEQ ID NO: 13.

15. The recombinant AfGATR of claim 3, wherein said AfGATR consists of an amino acid sequence with at least 99% amino acid sequence identity to SEQ ID NO: 13.

16. A method of saccharifying a composition comprising starch to produce a composition comprising glucose, wherein said method comprises:

(i) contacting a starch composition with the AfGATR of claim 3; and (ii) saccharifying the starch composition to produce said glucose composition;

wherein said AfGATR catalyzes the saccharification of the composition comprising starch to a composition comprising glucose.

17. The method of claim 16, wherein said composition comprising glucose is more significantly enriched in DP1 compared to a second composition comprising DP1 produced by *Aspergillus niger* glucoamylase (AnGA) after 24 hours of saccharification under the same conditions.

18. The method of claim 16, wherein said composition comprising glucose is enriched in DP1 compared to a second composition comprising DP1 produced by a wild-type AfGA under the same conditions.

19. The method of claim 16, wherein said AfGATR is AfGATR2 and wherein said composition comprising glucose is enriched in DP1 compared to a second composition comprising DP1 produced by AfGA1TR under the same conditions.

20. The method of claim 16, wherein the AfGATR is present at an amount about 40%-50% the amount of AnGA, to produce the same DP1 yield after 24 hours of saccharification under the same conditions.

21. The method of claim 16, wherein the method further comprises contacting a starch composition with an alpha-amylase.

22. The method of claim 21, wherein the alpha-amylase is AkAA.

23. The method of claim 16, wherein the method further comprises contacting a starch composition with a pullulanase.

24. The method of claim 16, further comprising fermenting the glucose composition to produce an End of Fermentation (EOF) product.

25. The method of claim 24, wherein the EOF product comprises a metabolite.

26. The method of claim 16, wherein said AfGATR is secreted by said *Trichoderma reesei* host cell.

27. The method of claim 26, wherein said host cell further expresses and secretes an alpha-amylase.

28. The method of claim 27, wherein said host cell further expresses and secretes a pullulanase.

29. The method of claim 26, wherein said composition comprising starch is contacted with said host cell.

* * * * *

SEQUENCE LISTING

<160> NUMBER OF SEQ ID NOS: 14

<210> SEQ ID NO 1
<211> LENGTH: 631
<212> TYPE: PRT
<213> ORGANISM: Aspergillus fumigatus
<220> FEATURE:
<221> NAME/KEY: misc_feature
<222> LOCATION: (1)..(631)
<223> OTHER INFORMATION: AfGA1 precursor

<400> SEQUENCE: 1

Met Pro Arg Leu Ser Tyr Ala Leu Cys Ala Leu Ser Leu Gly His Ala
1               5                   10                  15

Ala Ile Ala Ala Pro Gln Leu Ser Ala Arg Ala Thr Gly Ser Leu Asp
                20                  25                  30

Ser Trp Leu Gly Thr Glu Thr Thr Val Ala Leu Asn Gly Ile Leu Ala
            35                  40                  45

Asn Ile Gly Ala Asp Gly Ala Tyr Ala Lys Ser Ala Lys Pro Gly Ile
        50                  55                  60

```
Ile Ile Ala Ser Pro Ser Thr Ser Glu Pro Asp Tyr Tyr Thr Trp
 65                  70                  75                  80

Thr Arg Asp Ala Ala Leu Val Thr Lys Val Leu Val Asp Leu Phe Arg
                 85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Asn Pro Ser Gly Gly Leu Ala Ser
            115                 120                 125

Gly Gly Leu Ala Glu Pro Lys Tyr Asn Val Asp Met Thr Ala Phe Thr
130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
            195                 200                 205

Asn Ser Met Ser Phe Phe Thr Val Ala Val Gln His Arg Ala Leu Val
210                 215                 220

Glu Gly Ser Thr Phe Ala Lys Arg Val Gly Ala Ser Cys Ser Trp Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ala Asn Thr Val Leu Ala Ser Ile His Thr Phe Asp Pro Glu Ala Gly
            275                 280                 285

Cys Asp Asp Thr Thr Phe Gln Pro Cys Ser Pro Arg Ala Leu Ala Asn
290                 295                 300

His Lys Val Tyr Thr Asp Ser Phe Arg Ser Val Tyr Ala Ile Asn Ser
305                 310                 315                 320

Gly Ile Pro Gln Gly Ala Ala Val Ser Ala Gly Arg Tyr Pro Glu Asp
                325                 330                 335

Val Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Lys Lys Ile Gly Ser Ile
            355                 360                 365

Ser Ile Thr Ser Thr Ser Leu Ala Phe Phe Lys Asp Ile Tyr Ser Ser
            370                 375                 380

Ala Ala Val Gly Thr Tyr Ala Ser Ser Thr Ser Thr Phe Thr Asp Ile
385                 390                 395                 400

Ile Asn Ala Val Lys Thr Tyr Ala Asp Gly Tyr Val Ser Ile Val Gln
                405                 410                 415

Ala His Ala Met Asn Asn Gly Ser Leu Ser Glu Gln Phe Asp Lys Ser
            420                 425                 430

Ser Gly Leu Ser Leu Ser Ala Arg Asp Leu Thr Trp Ser Tyr Ala Ala
            435                 440                 445

Phe Leu Thr Ala Asn Met Arg Arg Asn Gly Val Val Pro Ala Pro Trp
            450                 455                 460

Gly Ala Ala Ser Ala Asn Ser Val Pro Ser Ser Cys Ser Met Gly Ser
465                 470                 475                 480
```

```
Ala Thr Gly Thr Tyr Ser Thr Ala Thr Ser Trp Pro Ser Thr
            485                 490                 495

Leu Thr Ser Gly Ser Pro Gly Ser Thr Thr Val Gly Thr Thr Thr
            500                 505                 510

Ser Thr Thr Ser Gly Thr Ala Ala Glu Thr Ala Cys Ala Thr Pro Thr
            515                 520                 525

Ala Val Ala Val Thr Phe Asn Glu Ile Ala Thr Thr Tyr Gly Glu
            530                 535                 540

Asn Val Tyr Ile Val Gly Ser Ile Ser Glu Leu Gly Asn Trp Asp Thr
545                 550                 555                 560

Ser Lys Ala Val Ala Leu Ser Ala Ser Lys Tyr Thr Ser Ser Asn Asn
                565                 570                 575

Leu Trp Tyr Val Ser Val Thr Leu Pro Ala Gly Thr Thr Phe Glu Tyr
            580                 585                 590

Lys Tyr Ile Arg Lys Glu Ser Asp Gly Ser Ile Val Trp Glu Ser Asp
            595                 600                 605

Pro Asn Arg Ser Tyr Thr Val Pro Ala Ala Cys Gly Val Ser Thr Ala
            610                 615                 620

Thr Glu Asn Asp Thr Trp Gln
625                 630

<210> SEQ ID NO 2
<211> LENGTH: 631
<212> TYPE: PRT
<213> ORGANISM: Aspergillus fumigatus A1163
<220> FEATURE:
<221> NAME/KEY: misc_feature
<222> LOCATION: (1)..(631)
<223> OTHER INFORMATION: AfGA2 precursor

<400> SEQUENCE: 2

Met Pro Arg Leu Ser Tyr Ala Leu Cys Ala Leu Ser Leu Gly His Ala
1               5                   10                  15

Ala Ile Ala Ala Pro Gln Leu Ser Ala Arg Ala Thr Gly Ser Leu Asp
            20                  25                  30

Ser Trp Leu Gly Thr Glu Thr Thr Val Ala Leu Asn Gly Ile Leu Ala
        35                  40                  45

Asn Ile Gly Ala Asp Gly Ala Tyr Ala Lys Ser Ala Lys Pro Gly Ile
    50                  55                  60

Ile Ile Ala Ser Pro Ser Thr Ser Glu Pro Asp Tyr Tyr Tyr Thr Trp
65                  70                  75                  80

Thr Arg Asp Ala Ala Leu Val Thr Lys Val Leu Val Asp Leu Phe Arg
                85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Asn Pro Ser Gly Gly Leu Ala Ser
        115                 120                 125

Gly Gly Leu Ala Glu Pro Lys Tyr Asn Val Asp Met Thr Ala Phe Thr
    130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
```

```
            195                 200                 205
Asn Ser Met Ser Phe Phe Thr Val Ala Val Gln His Arg Ala Leu Val
210                 215                 220
Glu Gly Ser Thr Phe Ala Lys Arg Val Gly Ala Ser Cys Ser Trp Cys
225                 230                 235                 240
Asp Ser Gln Ala Pro Gln Ile Leu Cys Tyr Met Gln Ser Phe Trp Thr
                    245                 250                 255
Gly Ser Tyr Ile Asn Ala Asn Thr Gly Gly Arg Ser Gly Lys Asp
            260                 265                 270
Ala Asn Thr Val Leu Ala Ser Ile His Thr Phe Asp Pro Glu Ala Gly
            275                 280                 285
Cys Asp Asp Thr Thr Phe Gln Pro Cys Ser Pro Arg Ala Leu Ala Asn
290                 295                 300
His Lys Val Tyr Thr Asp Ser Phe Arg Ser Val Tyr Ala Ile Asn Ser
305                 310                 315                 320
Gly Ile Pro Gln Gly Ala Ala Val Ser Ala Gly Arg Tyr Pro Glu Asp
                    325                 330                 335
Val Tyr Tyr Asn Gly Asn Pro Trp Phe Leu Thr Thr Leu Ala Ala Ala
            340                 345                 350
Glu Gln Leu Tyr Asp Ala Ile Tyr Gln Trp Lys Lys Ile Gly Ser Ile
            355                 360                 365
Ser Ile Thr Ser Thr Ser Leu Ala Phe Phe Lys Asp Ile Tyr Ser Ser
370                 375                 380
Ala Ala Val Gly Thr Tyr Ala Ser Ser Thr Ser Thr Phe Thr Asp Ile
385                 390                 395                 400
Ile Asn Ala Val Lys Thr Tyr Ala Asp Gly Tyr Val Ser Ile Val Gln
                    405                 410                 415
Ala His Ala Met Asn Asn Gly Ser Leu Ser Glu Gln Phe Asp Lys Ser
            420                 425                 430
Ser Gly Leu Ser Leu Ser Ala Arg Asp Leu Thr Trp Ser Tyr Ala Ala
            435                 440                 445
Phe Leu Thr Ala Asn Met Arg Arg Asn Gly Val Val Pro Ala Pro Trp
450                 455                 460
Gly Ala Ala Ser Ala Asn Ser Val Pro Ser Ser Cys Ser Met Gly Ser
465                 470                 475                 480
Ala Thr Gly Thr Tyr Ser Thr Ala Thr Ala Thr Ser Trp Pro Ser Thr
                    485                 490                 495
Leu Thr Ser Gly Ser Pro Gly Ser Thr Thr Val Gly Thr Thr Thr
            500                 505                 510
Ser Thr Thr Ser Gly Thr Ala Thr Glu Thr Ala Cys Ala Thr Pro Thr
            515                 520                 525
Ala Val Ala Val Thr Phe Asn Glu Ile Ala Thr Thr Tyr Gly Glu
            530                 535                 540
Asn Val Tyr Ile Val Gly Ser Ile Ser Glu Leu Gly Asn Trp Asp Thr
545                 550                 555                 560
Ser Lys Ala Val Ala Leu Ser Ala Ser Lys Tyr Thr Ser Ser Asn Asn
                    565                 570                 575
Leu Trp Tyr Val Ser Val Thr Leu Pro Ala Gly Thr Thr Phe Glu Tyr
            580                 585                 590
Lys Tyr Ile Arg Lys Glu Ser Asp Gly Ser Ile Val Trp Glu Ser Asp
            595                 600                 605
Pro Asn Arg Ser Tyr Thr Val Pro Ala Ala Cys Gly Val Ser Thr Ala
610                 615                 620
```

```
Thr Glu Asn Asp Thr Trp Arg
625                 630

<210> SEQ ID NO 3
<211> LENGTH: 627
<212> TYPE: PRT
<213> ORGANISM: Neosartorya fisheri NRRL 181
<220> FEATURE:
<221> NAME/KEY: misc_feature
<222> LOCATION: (1)..(627)
<223> OTHER INFORMATION: Nf_NRRL_181_GA

<400> SEQUENCE: 3

Met Pro Arg Leu Ser Tyr Ala Leu Cys Ala Leu Ser Leu Gly His Ala
1               5                   10                  15

Ala Ile Ala Ala Pro Gln Leu Ser Pro Arg Ala Thr Gly Ser Leu Asp
            20                  25                  30

Ser Trp Leu Ala Thr Glu Ser Thr Val Ser Leu Asn Gly Ile Leu Ala
        35                  40                  45

Asn Ile Gly Ala Asp Gly Ala Tyr Ala Lys Ser Ala Lys Pro Gly Ile
    50                  55                  60

Ile Ile Ala Ser Pro Ser Thr Ser Asp Pro Asp Tyr Tyr Tyr Thr Trp
65                  70                  75                  80

Thr Arg Asp Ala Ala Leu Val Thr Lys Val Leu Val Asp Leu Phe Arg
                85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Thr Pro Ser Gly Gly Leu Ser Ser
        115                 120                 125

Gly Gly Leu Ala Glu Pro Lys Tyr Asn Val Asp Met Thr Ala Phe Thr
130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
        195                 200                 205

Asn Ser Met Ser Phe Phe Thr Val Ala Val Gln His Arg Ala Leu Val
210                 215                 220

Glu Gly Ser Thr Phe Ala Lys Arg Val Gly Ala Ser Cys Ser Trp Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ala Asn Thr Val Leu Ala Ser Ile His Thr Phe Asp Pro Glu Ala Gly
        275                 280                 285

Cys Asp Asp Thr Thr Phe Gln Pro Cys Ser Pro Arg Ala Leu Ala Asn
290                 295                 300

His Lys Val Tyr Thr Asp Ser Phe Arg Ser Val Tyr Ala Ile Asn Ser
305                 310                 315                 320

Gly Ile Pro Gln Gly Val Ala Val Ser Ala Gly Arg Tyr Pro Glu Asp
                325                 330                 335
```

Val Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Lys Lys Ile Gly Ser Ile
        355                 360                 365

Ser Ile Thr Ser Thr Ser Leu Ala Phe Phe Lys Asp Ile Tyr Ser Ser
    370                 375                 380

Val Ala Val Gly Thr Tyr Ala Ser Ser Ser Thr Phe Thr Ala Ile
385                 390                 395                 400

Ile Asp Ala Val Lys Thr Tyr Ala Asp Gly Tyr Val Ser Ile Val Glu
                405                 410                 415

Ala His Ala Met Thr Asn Gly Ser Leu Ser Glu Gln Phe Asp Lys Ser
            420                 425                 430

Ser Gly Met Ser Leu Ser Ala Arg Asp Leu Thr Trp Ser Tyr Ala Ala
        435                 440                 445

Leu Leu Thr Ala Asn Met Arg Arg Asn Gly Val Val Pro Ala Pro Trp
    450                 455                 460

Gly Ala Ala Ser Ala Asn Ser Val Pro Ser Ser Cys Ser Met Gly Ser
465                 470                 475                 480

Ala Thr Gly Thr Tyr Ser Thr Ala Thr Ala Thr Ser Trp Pro Ser Thr
                485                 490                 495

Leu Thr Ser Gly Ser Pro Ser Asp Thr Thr Ser Gly Thr Thr Pro Gly
            500                 505                 510

Thr Thr Thr Thr Thr Ser Ala Cys Thr Thr Pro Thr Ser Val Ala Val
        515                 520                 525

Thr Phe Asp Glu Ile Ala Thr Thr Thr Tyr Gly Glu Asn Val Tyr Ile
    530                 535                 540

Ile Gly Ser Ile Ser Gln Leu Gly Ser Trp Asp Thr Ser Lys Ala Val
545                 550                 555                 560

Pro Leu Ser Ser Ser Lys Tyr Thr Ser Ser Asn Asn Leu Trp Tyr Val
                565                 570                 575

Thr Ile Asn Leu Pro Ala Gly Thr Thr Phe Glu Tyr Lys Tyr Ile Arg
            580                 585                 590

Lys Glu Ser Asp Gly Ser Ile Glu Trp Glu Ser Asp Pro Asn Arg Ser
        595                 600                 605

Tyr Thr Val Pro Ser Ala Cys Gly Val Ser Thr Ala Thr Glu Lys Asp
    610                 615                 620

Thr Trp Arg
625

<210> SEQ ID NO 4
<211> LENGTH: 637
<212> TYPE: PRT
<213> ORGANISM: Talaromyces stipitatus ATCC 10500
<220> FEATURE:
<221> NAME/KEY: misc_feature
<222> LOCATION: (1)..(637)
<223> OTHER INFORMATION: Ts_ATCC0_10500_GA

<400> SEQUENCE: 4

Met Thr Arg Leu Ser Ser Val Leu Cys Ala Leu Ala Leu Gly Gln
1               5                   10                  15

Thr Ala Leu Ala Ala Pro Gly Leu Ser Pro Arg Ala Ser Thr Ser Leu
            20                  25                  30

Asp Ala Trp Leu Ala Thr Glu Thr Thr Val Ser Leu Ser Gly Ile Leu
        35                  40                  45

Ala Asn Ile Gly Ala Asp Gly Ala Tyr Ser Lys Ser Ala Lys Pro Gly

```
            50                  55                  60
Val Val Ile Ala Ser Pro Ser Thr Asp Asn Pro Asn Tyr Tyr Tyr Thr
 65                  70                  75                  80

Trp Thr Arg Asp Ser Ala Leu Thr Leu Lys Val Leu Ile Asp Leu Phe
                     85                  90                  95

Arg Asn Gly Asn Leu Gly Leu Gln Thr Val Ile Glu Glu Tyr Val Asn
                100                 105                 110

Ala Gln Ala Tyr Leu Gln Thr Val Ser Asn Pro Ser Gly Asp Leu Ser
                115                 120                 125

Ser Gly Ala Gly Leu Ala Glu Pro Lys Phe Asn Val Asp Met Ser Ala
                130                 135                 140

Phe Thr Gly Ser Trp Gly Arg Pro Gln Arg Asp Gly Pro Ala Leu Arg
145                 150                 155                 160

Ala Ile Ala Leu Ile Asp Phe Gly Asn Trp Leu Ile Glu Asn Gly Tyr
                165                 170                 175

Thr Ser Leu Ala Ala Asn Asn Ile Trp Pro Ile Val Arg Asn Asp Leu
                180                 185                 190

Ser Tyr Val Ala Gln Tyr Trp Ser Gln Ser Gly Phe Asp Leu Trp Glu
                195                 200                 205

Glu Val Asn Ser Met Ser Phe Phe Thr Val Ala Asn Gln His Arg Ser
210                 215                 220

Leu Val Glu Gly Ser Thr Phe Ala Ala Lys Val Gly Ala Ser Cys Ser
225                 230                 235                 240

Trp Cys Asp Ser Gln Ala Pro Gln Ile Leu Cys Tyr Met Gln Thr Phe
                245                 250                 255

Trp Thr Gly Ser Tyr Met Asn Ala Asn Thr Gly Gly Gly Arg Ser Gly
                260                 265                 270

Lys Asp Ala Asn Thr Val Leu Thr Ser Ile Ala Thr Phe Asp Pro Glu
                275                 280                 285

Ala Thr Cys Asp Asp Val Thr Phe Gln Pro Cys Ser Pro Arg Ala Leu
                290                 295                 300

Ala Asn His Lys Val Tyr Thr Asp Ser Phe Arg Ser Val Tyr Gly Leu
305                 310                 315                 320

Asn Ser Gly Ile Ala Glu Gly Val Ala Val Ala Val Gly Arg Tyr Pro
                325                 330                 335

Glu Asp Ser Tyr Tyr Asn Gly Asn Pro Trp Phe Leu Ser Asn Leu Ala
                340                 345                 350

Ala Ala Glu Gln Leu Tyr Asp Ala Ile Tyr Gln Trp Asn Lys Ile Gly
                355                 360                 365

Ser Ile Thr Ile Thr Ser Thr Ser Leu Ala Phe Phe Lys Asp Val Tyr
370                 375                 380

Ser Ser Ala Ala Val Gly Thr Tyr Ala Ser Gly Ser Ser Ala Phe Thr
385                 390                 395                 400

Ser Ile Ile Asn Ala Val Lys Thr Tyr Ala Asp Gly Tyr Ile Ser Val
                405                 410                 415

Val Gln Ser His Ala Met Asn Asn Gly Ser Leu Ser Glu Gln Phe Asp
                420                 425                 430

Lys Asn Thr Gly Ala Glu Leu Ser Ala Arg Asp Leu Thr Trp Ser Tyr
                435                 440                 445

Ala Ala Leu Leu Thr Ala Asn Met Arg Arg Asn Gly Val Val Pro Pro
450                 455                 460

Ser Trp Gly Ala Ala Ser Ala Thr Ser Ile Pro Ser Ser Cys Thr Thr
465                 470                 475                 480
```

```
Gly Ser Ala Ile Gly Thr Tyr Ser Thr Pro Thr Ala Thr Ser Trp Pro
                485                 490                 495

Ser Thr Leu Thr Ser Gly Thr Gly Ser Pro Gly Ser Thr Thr Ser Ala
            500                 505                 510

Thr Gly Ser Val Ser Thr Ser Val Ser Ala Thr Thr Ser Ala Gly
            515                 520                 525

Ser Cys Thr Thr Pro Thr Ser Val Ala Val Thr Phe Asp Glu Ile Ala
        530                 535                 540

Thr Thr Ser Tyr Gly Glu Asn Val Tyr Ile Val Gly Ser Ile Ser Gln
545                 550                 555                 560

Leu Gly Ser Trp Asn Thr Ala Asn Ala Ile Ala Leu Ser Ala Ser Lys
                565                 570                 575

Tyr Thr Thr Ser Asn Asn Leu Trp Tyr Val Thr Ile Asn Leu Pro Ala
            580                 585                 590

Gly Thr Thr Phe Gln Tyr Lys Tyr Ile Arg Lys Glu Ser Asp Gly Thr
            595                 600                 605

Val Lys Trp Glu Ser Asp Pro Asn Arg Ser Tyr Thr Val Pro Ser Ala
        610                 615                 620

Cys Gly Val Ser Thr Ala Thr Glu Asn Asp Thr Trp Arg
625                 630                 635

<210> SEQ ID NO 5
<211> LENGTH: 641
<212> TYPE: PRT
<213> ORGANISM: Penicillium marneffei ATCC 18224
<220> FEATURE:
<221> NAME/KEY: misc_feature
<222> LOCATION: (1)..(641)
<223> OTHER INFORMATION: Pm_ATCC_18224_GA

<400> SEQUENCE: 5

Met Thr Phe Ser Arg Leu Ser Ser Val Leu Cys Ala Leu Ala Ala
1               5                   10                  15

Leu Gly His Asn Ala Leu Ala Ala Pro Gln Phe Ser Pro Arg Ala Thr
                20                  25                  30

Val Gly Leu Asp Ala Trp Leu Ala Ser Glu Thr Thr Phe Ser Leu Asn
            35                  40                  45

Gly Ile Leu Ala Asn Ile Gly Ser Ser Gly Ala Tyr Ser Ala Ser Ala
        50                  55                  60

Lys Pro Gly Val Val Ile Ala Ser Pro Ser Thr Asn Pro Asn Tyr
65                  70                  75                  80

Tyr Tyr Thr Trp Thr Arg Asp Ser Ala Leu Thr Leu Lys Val Leu Ile
                85                  90                  95

Asp Leu Phe Gly Asn Gly Asn Leu Ser Leu Gln Thr Val Ile Glu Glu
            100                 105                 110

Tyr Ile Asn Ala Gln Ala Tyr Leu Gln Thr Val Ser Asn Pro Ser Gly
        115                 120                 125

Asp Leu Ser Ser Gly Ala Gly Leu Ala Glu Pro Lys Tyr Asn Val Asp
    130                 135                 140

Met Ser Pro Phe Thr Gly Gly Trp Gly Arg Pro Gln Arg Asp Gly Pro
145                 150                 155                 160

Ala Leu Arg Ala Ile Ala Leu Ile Glu Phe Gly Asn Trp Leu Ile Asp
                165                 170                 175

Asn Gly Tyr Ser Ser Tyr Ala Val Asn Asn Ile Trp Pro Ile Val Arg
            180                 185                 190
```

```
Asn Asp Leu Ser Tyr Val Ser Gln Tyr Trp Ser Gln Ser Gly Phe Asp
        195                 200                 205

Leu Trp Glu Glu Val Asn Ser Met Ser Phe Phe Thr Val Ala Asn Gln
210                 215                 220

His Arg Ala Leu Val Gln Gly Ser Thr Phe Ala Ala Arg Val Gly Ala
225                 230                 235                 240

Ser Cys Ser Trp Cys Asp Ser Gln Ala Pro Gln Ile Leu Cys Tyr Met
                245                 250                 255

Gln Thr Phe Trp Thr Gly Ser Tyr Ile Asn Ala Asn Thr Gly Gly Gly
            260                 265                 270

Arg Ser Gly Lys Asp Ser Asn Thr Val Leu Thr Thr Ile His Thr Phe
        275                 280                 285

Asp Pro Glu Ala Thr Cys Asp Asp Val Thr Phe Gln Pro Cys Ser Pro
290                 295                 300

Arg Ala Leu Ala Asn His Lys Val Tyr Thr Asp Ser Phe Arg Ser Ile
305                 310                 315                 320

Tyr Gly Val Asn Ser Gly Ile Ala Gln Gly Val Ala Val Ser Val Gly
                325                 330                 335

Arg Tyr Pro Glu Asp Ser Tyr Tyr Gly Gly Asn Pro Trp Phe Leu Ser
            340                 345                 350

Asn Leu Ala Ala Ala Glu Gln Leu Tyr Asp Ala Ile Tyr Gln Trp Asn
        355                 360                 365

Lys Ile Gly Ser Ile Thr Ile Thr Ser Thr Ser Leu Ala Phe Phe Lys
        370                 375                 380

Asp Val Tyr Ser Ala Ala Val Gly Thr Tyr Ala Ser Gly Ser Thr
385                 390                 395                 400

Ala Phe Thr Ser Ile Ile Ser Ala Val Lys Thr Tyr Ala Asp Gly Tyr
                405                 410                 415

Val Ser Ile Val Gln Gly His Ala Ala Ala Asn Gly Ser Leu Ser Glu
            420                 425                 430

Gln Phe Asp Arg Asn Ser Gly Val Glu Ile Ser Ala Arg Asp Leu Thr
        435                 440                 445

Trp Ser Tyr Ala Ala Leu Leu Thr Ala Asn Leu Arg Arg Asn Gly Val
450                 455                 460

Met Pro Pro Ser Trp Gly Ala Ala Ser Ala Asn Ser Val Pro Ser Ser
465                 470                 475                 480

Cys Ser Met Gly Ser Ala Thr Gly Thr Tyr Ser Thr Pro Thr Ala Thr
                485                 490                 495

Ala Trp Pro Ser Thr Leu Thr Ser Ala Thr Gly Ile Pro Val Thr Thr
            500                 505                 510

Ser Ala Thr Ala Ser Val Thr Lys Ala Thr Ser Ala Thr Ser Thr Thr
        515                 520                 525

Thr Ser Ala Thr Thr Cys Thr Thr Pro Thr Ser Val Ala Val Thr Phe
530                 535                 540

Asp Glu Ile Ala Thr Thr Thr Tyr Gly Glu Asn Val Phe Ile Val Gly
545                 550                 555                 560

Ser Ile Ser Gln Leu Gly Ser Trp Asp Thr Ser Lys Ala Ile Ala Leu
                565                 570                 575

Ser Ala Ser Gln Tyr Thr Ser Ser Asn His Leu Trp Phe Ala Thr Leu
            580                 585                 590

Ser Leu Pro Ala Gly Thr Thr Phe Gln Tyr Lys Tyr Ile Arg Lys Glu
        595                 600                 605

Ser Asn Gly Ser Ile Val Trp Glu Ser Asp Pro Asn Arg Ser Tyr Thr
```

```
                610             615                 620
Val Pro Ser Gly Cys Gly Val Ser Thr Ala Thr Glu Asn Asp Thr Trp
625                 630                 635                 640

Arg

<210> SEQ ID NO 6
<211> LENGTH: 661
<212> TYPE: PRT
<213> ORGANISM: Aspergillus nidulans FGSC A4
<220> FEATURE:
<221> NAME/KEY: misc_feature
<222> LOCATION: (1)..(661)
<223> OTHER INFORMATION: An_FGSC_A4_GA

<400> SEQUENCE: 6

Met Pro Thr Thr Ile Leu Lys Ile Thr Leu Phe Pro Leu Ile Asp Ser
1               5                   10                  15

Ile Phe Ser Val Gln Leu Ser Pro Val Arg Ile Ala Met Leu Thr Leu
                20                  25                  30

Ser Lys Val Leu Pro Val Leu Ala Leu Ser His Ala Val Ala Ala Ala
                35                  40                  45

Pro Gln Leu Ser Ala Arg Ala Thr Ala Ser Leu Asn Thr Trp Leu Ser
50                  55                  60

Thr Glu Ala Ser Phe Ala Leu Asp Gly Ile Leu Thr Asn Ile Gly Ala
65                  70                  75                  80

Asn Gly Ala Tyr Ala Lys Thr Ala Lys Ala Gly Ala Asp Tyr Tyr Thr
                85                  90                  95

Trp Thr Arg Asp Ala Ala Leu Thr Val Lys Val Leu Val Asp Leu Phe
                100                 105                 110

His Asn Gly Asp Leu Ser Leu Gln Thr Ile Leu Glu Glu Tyr Thr Asn
            115                 120                 125

Ser Gln Ala Tyr Leu Gln Thr Val Ser Asn Pro Ser Gly Gly Leu Ala
        130                 135                 140

Ser Gly Gly Leu Ala Glu Pro Lys Phe Tyr Val Asp Met Thr Ala Phe
145                 150                 155                 160

Thr Gly Ser Trp Gly Arg Pro Gln Arg Asp Gly Pro Ala Leu Arg Ala
                165                 170                 175

Thr Thr Leu Ile Gly Phe Gly Asn Trp Leu Ile Asp Asn Gly Tyr Ser
                180                 185                 190

Ser Tyr Ala Ser Asn Asn Ile Trp Pro Ile Val Arg Asn Asp Leu Thr
            195                 200                 205

Tyr Val Ala Gln Tyr Trp Ser Lys Ser Gly Tyr Asp Leu Trp Glu Glu
        210                 215                 220

Val Asn Ser Met Ser Phe Phe Thr Val Ala Val Gln His Arg Ala Leu
225                 230                 235                 240

Val Glu Gly Ser Thr Phe Ala His Arg Val Gly Ala Ser Cys Pro Trp
                245                 250                 255

Cys Asp Ser Gln Ala Pro Gln Ile Leu Cys Tyr Met Gln Asn Phe Trp
                260                 265                 270

Thr Gly Ser Tyr Ile Asn Ala Asn Thr Gly Gly Gly Arg Ser Gly Lys
            275                 280                 285

Asp Ala Asn Thr Val Leu Ala Ser Ile His Thr Phe Asp Pro Asp Ala
        290                 295                 300

Ala Cys Asp Asp Ile Thr Phe Gln Pro Cys Ser Ser Arg Ala Leu Ala
305                 310                 315                 320
```

Asn His Lys Val Tyr Thr Asp Ser Phe Arg Ser Val Tyr Ser Leu Asn
325                 330                 335

Thr Gly Ile Ala Gln Gly Val Ala Val Ala Ala Gly Arg Tyr Pro Glu
        340                 345                 350

Asp Ser Tyr Tyr Asn Gly Asn Pro Trp Phe Leu Thr Thr Leu Ala Ala
        355                 360                 365

Ala Glu Gln Leu Tyr Asp Ala Ile Tyr Gln Trp Gln Lys Ala Arg Ser
370                 375                 380

Ile Ser Ile Thr Ser Thr Ser Leu Ala Phe Phe Lys Asp Ile Tyr Ser
385                 390                 395                 400

Ser Ala Ala Val Gly Thr Tyr Ala Ser Gly Ser Ser Ala Phe Thr Ala
                405                 410                 415

Ile Ile Asp Ala Val Lys Thr Tyr Ala Asp Gly Tyr Val Ser Ile Val
            420                 425                 430

Lys Ala His Ala Met Ala Asn Gly Ser Leu Ser Glu Gln Phe Asp Lys
                435                 440                 445

Thr Tyr Gly Thr Cys Val Ser Ala Arg Asp Leu Thr Trp Ser Tyr Ala
        450                 455                 460

Ala Leu Leu Thr Ala Ser Met Arg Arg Asn Gly Val Val Pro Pro Ser
465                 470                 475                 480

Trp Asp Ala Ala Ser Ala Asn Thr Leu Pro Ser Ser Cys Ser Thr Gly
                485                 490                 495

Ser Ala Thr Gly Thr Tyr Ser Thr Ala Thr Val Thr Thr Trp Pro Ser
                500                 505                 510

Thr Leu Thr Ser Gly Ser Ala Ser Ala Thr Thr Thr Ile Met Ala Thr
            515                 520                 525

Ser Thr Ala Thr Ser Ser Ser Thr Thr Thr Ser Thr Thr Thr Ala Cys
530                 535                 540

Thr Thr Pro Ser Thr Val Ala Val Thr Phe Asn Val Ile Ala Thr Thr
545                 550                 555                 560

Thr Tyr Gly Glu Asn Val Tyr Ile Val Gly Ser Ile Ser Gln Leu Gly
                565                 570                 575

Asn Trp Asp Thr Gly Ser Ala Val Ala Leu Ser Ala Ser Lys Asn Thr
            580                 585                 590

Ser Ser Asn Asn Leu Trp Tyr Val Asp Ile Asn Leu Pro Gly Gly Thr
        595                 600                 605

Ala Phe Glu Tyr Lys Tyr Ile Arg Lys Glu Thr Asp Gly Ser Ile Val
610                 615                 620

Trp Glu Ser Asp Pro Asn Arg Ser Tyr Thr Val Pro Ser Ser Cys Gly
625                 630                 635                 640

Val Ser Thr Ala Thr Glu Ser Asp Thr Trp Arg Cys Thr Leu Glu Thr
                645                 650                 655

Gln Ser Val Arg Asn
            660

<210> SEQ ID NO 7
<211> LENGTH: 97
<212> TYPE: PRT
<213> ORGANISM: Aspergillus fumigatus
<220> FEATURE:
<221> NAME/KEY: misc_feature
<222> LOCATION: (1)..(97)
<223> OTHER INFORMATION: AfGA1 and AfGA2 CBM

<400> SEQUENCE: 7

Phe Asn Glu Ile Ala Thr Thr Thr Tyr Gly Glu Asn Val Tyr Ile Val

| | 1 | | | 5 | | | | | 10 | | | | | 15 | |
|---|---|---|---|---|---|---|---|---|---|---|---|---|---|---|---|
| Gly | Ser | Ile | Ser | Glu | Leu | Gly | Asn | Trp | Asp | Thr | Ser | Lys | Ala | Val | Ala |

Leu Ser Ala Ser Lys Tyr Thr Ser Asn Asn Leu Trp Tyr Val Ser
              35                  40                  45

Val Thr Leu Pro Ala Gly Thr Thr Phe Glu Tyr Lys Tyr Ile Arg Lys
        50                  55                  60

Glu Ser Asp Gly Ser Ile Val Trp Glu Ser Asp Pro Asn Arg Ser Tyr
65                  70                  75                  80

Thr Val Pro Ala Ala Cys Gly Val Ser Thr Ala Thr Glu Asn Asp Thr
                    85                  90                  95

Trp

<210> SEQ ID NO 8
<211> LENGTH: 2060
<212> TYPE: DNA
<213> ORGANISM: Aspergillus fumigatus
<220> FEATURE:
<221> NAME/KEY: misc_feature
<222> LOCATION: (1)..(2060)
<223> OTHER INFORMATION: AfGA1 gene of pTrex3gM-AfGA1

<400> SEQUENCE: 8

```
atgcctcgcc tttcctacgc gctctgtgcg ctgtctctcg ggcatgctgc tattgcagct    60
cctcagttat ccgctcgtgc taccggcagc ttggactcct ggttgggtac tgagaccacc   120
gttgcgctca atggtattct ggccaacatc ggtgccgacg tgcttatgc gaagagcgct   180
aagcctggca taatcattgc cagtccgagc accagcgaac cagactgtga gaaccttcct   240
gaactggccc tgtccggcag tcattgacct cggtagacta ctatacctgg acgagagatg   300
ctgctctcgt cacgaaagtc ctggtcgacc tcttccgcaa cggcaacctg gtctgcaga   360
aagtcattac cgaatacgtc aactctcagg cgtacttgca gaccgtgtct aatccgtcgg   420
gtggtcttgc gagcggaggt ctcgcggagc taagtacaa cgtcgacatg acggccttta   480
ccggagcctg gggtcgtcct cagcgtgatg gtccggctct gcgggccacc gccctcatcg   540
actttggcaa ctggctgatt gtatgttctc catacgagcc ccaggaagcg ttgctgacgt   600
ctacaggaca acggctactc cagctatgct gtcaacaaca tctggcccat tgtgcgcaac   660
gacttgtcct acgtttctca gtactggagc cagagtggct ttggtgagtc ccgactctct   720
ggaagtttac aacgtgcatc gattactgac aattgagatt ctacgtgaca gatctctggg   780
aagaagtcaa ctccatgtcc ttcttcaccg tcgctgtcca gcaccgtgcc ctcgtggagg   840
gaagcacgtt cgctaaacgg gtgggagcgt cgtgctcgtg gtgtgactcg caggcccccc   900
agatcctctg ctacatgcag agtttctgga ctggctcgta tatcaacgcc aacaccggtg   960
gtggccggtc cggcaaggat gccaacaccg tcctcgccag catccatacc ttcgaccccg  1020
aagccggctg cgacgatact actttccagc cctgctctcc tcgggccctt gccaaccaca  1080
aggtgtacac cgattcgttc cgctcggtct acgcgatcaa ctccggcatc ccacagggcg  1140
ctgccgtttc cgctggccgc tacccctgagg acgtctacta caacggcaac ccttggttcc  1200
tcaccaccct cgccgctgcc gagcagctct acgacgctat ctaccagtgg aagaagatcg  1260
gttccatcag catcaccagc aacctccctcg ccttcttcaa ggacatctac agctccgccg  1320
cggtcggcac ctacgcctct agcacctcca ccttcacgga catcatcaac gcggtcaaga  1380
cctacgcaga cggctacgtg agcatcgtcc aggcacacgc catgaacaac ggctcccttt  1440
```

```
cggagcaatt cgacaagtcc tctgggctgt ccctctccgc ccgcgatctg acctggtcct   1500
acgccgcttt cctcaccgcc aacatgcgtc gtaacggcgt ggtgcctgcc ccctggggcg   1560
ccgcctccgc caactccgtc ccctcgtctt gctccatggg ctcggccacg ggcacctaca   1620
gcaccgcgac agccacctcc tggcccagca cgctgaccag cggctcgcca ggcagcacca   1680
ccaccgtggg caccacgacc agtaccacct ctggcaccgc cgccgagacc gcctgtgcga   1740
cccctaccgc cgtggccgtc acctttaacg agatcgccac caccacctac ggcgagaatg   1800
tttacattgt tgggtccatc tccgagctcg ggaactggga taccagcaaa gcagtggccc   1860
tgagtgcgtc caagtatacc tccagcaata acctctggta cgtgtccgtc accctgccgg   1920
ctggcacgac attcgagtac aagtatatcc gcaaggaaag cgatggctcg atcgtgtggg   1980
agagtgaccc caaccgctcg tatacggtgc cggcagcttg tggagtgtct actgcgaccg   2040
agaatgatac ttggcagtga                                                2060
```

<210> SEQ ID NO 9
<211> LENGTH: 34
<212> TYPE: DNA
<213> ORGANISM: Artificial Sequence
<220> FEATURE:
<223> OTHER INFORMATION: Synthetic primer AfGA1-Fw

<400> SEQUENCE: 9
gcggcggccg caccatgcct cgcctttcct acgc                                 34

<210> SEQ ID NO 10
<211> LENGTH: 36
<212> TYPE: DNA
<213> ORGANISM: Artificial Sequence
<220> FEATURE:
<223> OTHER INFORMATION: Synthetic primer AfGA1-Rv

<400> SEQUENCE: 10
ccggcgcgcc cttatcactg ccaagtatca ttctcg                               36

<210> SEQ ID NO 11
<211> LENGTH: 19
<212> TYPE: PRT
<213> ORGANISM: Aspergillus fumigatus
<220> FEATURE:
<221> NAME/KEY: misc_feature
<222> LOCATION: (1)..(19)
<223> OTHER INFORMATION: AfGA1 and AfGA2 signal peptide

<400> SEQUENCE: 11

Met Pro Arg Leu Ser Tyr Ala Leu Cys Ala Leu Ser Leu Gly His Ala
1               5                   10                  15

Ala Ile Ala

<210> SEQ ID NO 12
<211> LENGTH: 612
<212> TYPE: PRT
<213> ORGANISM: Aspergillus fumigatus
<220> FEATURE:
<221> NAME/KEY: misc_feature
<222> LOCATION: (1)..(612)
<223> OTHER INFORMATION: AfGA1 Mature form

<400> SEQUENCE: 12

Ala Pro Gln Leu Ser Ala Arg Ala Thr Gly Ser Leu Asp Ser Trp Leu
1               5                   10                  15

Gly Thr Glu Thr Thr Val Ala Leu Asn Gly Ile Leu Ala Asn Ile Gly

-continued

```
                    20                  25                  30
Ala Asp Gly Ala Tyr Ala Lys Ser Ala Lys Pro Gly Ile Ile Ala
                35                  40                  45
Ser Pro Ser Thr Ser Glu Pro Asp Tyr Tyr Thr Trp Thr Arg Asp
    50                  55                  60
Ala Ala Leu Val Thr Lys Val Leu Val Asp Leu Phe Arg Asn Gly Asn
65                  70                  75                  80
Leu Gly Leu Gln Lys Val Ile Thr Glu Tyr Val Asn Ser Gln Ala Tyr
                85                  90                  95
Leu Gln Thr Val Ser Asn Pro Ser Gly Gly Leu Ala Ser Gly Gly Leu
                100                 105                 110
Ala Glu Pro Lys Tyr Asn Val Asp Met Thr Ala Phe Thr Gly Ala Trp
            115                 120                 125
Gly Arg Pro Gln Arg Asp Gly Pro Ala Leu Arg Ala Thr Ala Leu Ile
        130                 135                 140
Asp Phe Gly Asn Trp Leu Ile Asp Asn Gly Tyr Ser Ser Tyr Ala Val
145                 150                 155                 160
Asn Asn Ile Trp Pro Ile Val Arg Asn Asp Leu Ser Tyr Val Ser Gln
                165                 170                 175
Tyr Trp Ser Gln Ser Gly Phe Asp Leu Trp Glu Glu Val Asn Ser Met
                180                 185                 190
Ser Phe Phe Thr Val Ala Val Gln His Arg Ala Leu Val Glu Gly Ser
            195                 200                 205
Thr Phe Ala Lys Arg Val Gly Ala Ser Cys Ser Trp Cys Asp Ser Gln
        210                 215                 220
Ala Pro Gln Ile Leu Cys Tyr Met Gln Ser Phe Trp Thr Gly Ser Tyr
225                 230                 235                 240
Ile Asn Ala Asn Thr Gly Gly Arg Ser Gly Lys Asp Ala Asn Thr
                245                 250                 255
Val Leu Ala Ser Ile His Thr Phe Asp Pro Glu Ala Gly Cys Asp Asp
                260                 265                 270
Thr Thr Phe Gln Pro Cys Ser Pro Arg Ala Leu Ala Asn His Lys Val
        275                 280                 285
Tyr Thr Asp Ser Phe Arg Ser Val Tyr Ala Ile Asn Ser Gly Ile Pro
    290                 295                 300
Gln Gly Ala Ala Val Ser Ala Gly Arg Tyr Pro Glu Asp Val Tyr Tyr
305                 310                 315                 320
Asn Gly Asn Pro Trp Phe Leu Thr Thr Leu Ala Ala Ala Glu Gln Leu
                325                 330                 335
Tyr Asp Ala Ile Tyr Gln Trp Lys Lys Ile Gly Ser Ile Ser Ile Thr
            340                 345                 350
Ser Thr Ser Leu Ala Phe Phe Lys Asp Ile Tyr Ser Ser Ala Ala Val
        355                 360                 365
Gly Thr Tyr Ala Ser Ser Thr Ser Thr Phe Thr Asp Ile Ile Asn Ala
    370                 375                 380
Val Lys Thr Tyr Ala Asp Gly Tyr Val Ser Ile Val Gln Ala His Ala
385                 390                 395                 400
Met Asn Asn Gly Ser Leu Ser Glu Gln Phe Asp Lys Ser Ser Gly Leu
                405                 410                 415
Ser Leu Ser Ala Arg Asp Leu Thr Trp Ser Tyr Ala Ala Phe Leu Thr
            420                 425                 430
Ala Asn Met Arg Arg Asn Gly Val Val Pro Ala Pro Trp Gly Ala Ala
        435                 440                 445
```

```
Ser Ala Asn Ser Val Pro Ser Cys Ser Met Gly Ser Ala Thr Gly
    450                 455                 460

Thr Tyr Ser Thr Ala Thr Ala Thr Ser Trp Pro Ser Thr Leu Thr Ser
465                 470                 475                 480

Gly Ser Pro Gly Ser Thr Thr Val Gly Thr Thr Ser Thr Thr
                485                 490                 495

Ser Gly Thr Ala Ala Glu Thr Ala Cys Ala Thr Pro Thr Ala Val Ala
                500                 505                 510

Val Thr Phe Asn Glu Ile Ala Thr Thr Tyr Gly Glu Asn Val Tyr
            515                 520                 525

Ile Val Gly Ser Ile Ser Glu Leu Gly Asn Trp Asp Thr Ser Lys Ala
    530                 535                 540

Val Ala Leu Ser Ala Ser Lys Tyr Thr Ser Ser Asn Leu Trp Tyr
545                 550                 555                 560

Val Ser Val Thr Leu Pro Ala Gly Thr Thr Phe Glu Tyr Lys Tyr Ile
                565                 570                 575

Arg Lys Glu Ser Asp Gly Ser Ile Val Trp Glu Ser Asp Pro Asn Arg
                580                 585                 590

Ser Tyr Thr Val Pro Ala Ala Cys Gly Val Ser Thr Ala Thr Glu Asn
                595                 600                 605

Asp Thr Trp Gln
    610

<210> SEQ ID NO 13
<211> LENGTH: 612
<212> TYPE: PRT
<213> ORGANISM: Aspergillus fumigatus
<220> FEATURE:
<221> NAME/KEY: misc_feature
<222> LOCATION: (1)..(612)
<223> OTHER INFORMATION: AfGA2 Mature form

<400> SEQUENCE: 13

Ala Pro Gln Leu Ser Ala Arg Ala Thr Gly Ser Leu Asp Ser Trp Leu
1               5                   10                  15

Gly Thr Glu Thr Thr Val Ala Leu Asn Gly Ile Leu Ala Asn Ile Gly
                20                  25                  30

Ala Asp Gly Ala Tyr Ala Lys Ser Ala Lys Pro Gly Ile Ile Ile Ala
            35                  40                  45

Ser Pro Ser Thr Ser Glu Pro Asp Tyr Tyr Thr Trp Thr Arg Asp
    50                  55                  60

Ala Ala Leu Val Thr Lys Val Leu Val Asp Leu Phe Arg Asn Gly Asn
65                  70                  75                  80

Leu Gly Leu Gln Lys Val Ile Thr Glu Tyr Val Asn Ser Gln Ala Tyr
                85                  90                  95

Leu Gln Thr Val Ser Asn Pro Ser Gly Gly Leu Ala Ser Gly Gly Leu
            100                 105                 110

Ala Glu Pro Lys Tyr Asn Val Asp Met Thr Ala Phe Thr Gly Ala Trp
        115                 120                 125

Gly Arg Pro Gln Arg Asp Gly Pro Ala Leu Arg Ala Thr Ala Leu Ile
    130                 135                 140

Asp Phe Gly Asn Trp Leu Ile Asp Asn Gly Tyr Ser Ser Tyr Ala Val
145                 150                 155                 160

Asn Asn Ile Trp Pro Ile Val Arg Asn Asp Leu Ser Tyr Val Ser Gln
                165                 170                 175
```

```
Tyr Trp Ser Gln Ser Gly Phe Asp Leu Trp Glu Glu Val Asn Ser Met
            180                 185                 190

Ser Phe Phe Thr Val Ala Val Gln His Arg Ala Leu Val Glu Gly Ser
        195                 200                 205

Thr Phe Ala Lys Arg Val Gly Ala Ser Cys Ser Trp Cys Asp Ser Gln
    210                 215                 220

Ala Pro Gln Ile Leu Cys Tyr Met Gln Ser Phe Trp Thr Gly Ser Tyr
225                 230                 235                 240

Ile Asn Ala Asn Thr Gly Gly Arg Ser Gly Lys Asp Ala Asn Thr
                245                 250                 255

Val Leu Ala Ser Ile His Thr Phe Asp Pro Glu Ala Gly Cys Asp Asp
            260                 265                 270

Thr Thr Phe Gln Pro Cys Ser Pro Arg Ala Leu Ala Asn His Lys Val
        275                 280                 285

Tyr Thr Asp Ser Phe Arg Ser Val Tyr Ala Ile Asn Ser Gly Ile Pro
    290                 295                 300

Gln Gly Ala Ala Val Ser Ala Gly Arg Tyr Pro Glu Asp Val Tyr Tyr
305                 310                 315                 320

Asn Gly Asn Pro Trp Phe Leu Thr Thr Leu Ala Ala Ala Glu Gln Leu
                325                 330                 335

Tyr Asp Ala Ile Tyr Gln Trp Lys Lys Ile Gly Ser Ile Ser Ile Thr
            340                 345                 350

Ser Thr Ser Leu Ala Phe Phe Lys Asp Ile Tyr Ser Ala Ala Val
        355                 360                 365

Gly Thr Tyr Ala Ser Ser Thr Ser Thr Phe Thr Asp Ile Ile Asn Ala
370                 375                 380

Val Lys Thr Tyr Ala Asp Gly Tyr Val Ser Ile Val Gln Ala His Ala
385                 390                 395                 400

Met Asn Asn Gly Ser Leu Ser Glu Gln Phe Asp Lys Ser Ser Gly Leu
                405                 410                 415

Ser Leu Ser Ala Arg Asp Leu Thr Trp Ser Tyr Ala Ala Phe Leu Thr
            420                 425                 430

Ala Asn Met Arg Arg Asn Gly Val Val Pro Ala Pro Trp Gly Ala Ala
        435                 440                 445

Ser Ala Asn Ser Val Pro Ser Ser Cys Ser Met Gly Ser Ala Thr Gly
450                 455                 460

Thr Tyr Ser Thr Ala Thr Ala Thr Ser Trp Pro Ser Thr Leu Thr Ser
465                 470                 475                 480

Gly Ser Pro Gly Ser Thr Thr Val Gly Thr Thr Thr Ser Thr Thr
                485                 490                 495

Ser Gly Thr Ala Thr Glu Thr Ala Cys Ala Thr Pro Thr Ala Val Ala
            500                 505                 510

Val Thr Phe Asn Glu Ile Ala Thr Thr Thr Tyr Gly Glu Asn Val Tyr
        515                 520                 525

Ile Val Gly Ser Ile Ser Glu Leu Gly Asn Trp Asp Thr Ser Lys Ala
    530                 535                 540

Val Ala Leu Ser Ala Ser Lys Tyr Thr Ser Ser Asn Asn Leu Trp Tyr
545                 550                 555                 560

Val Ser Val Thr Leu Pro Ala Gly Thr Thr Phe Glu Tyr Lys Tyr Ile
                565                 570                 575

Arg Lys Glu Ser Asp Gly Ser Ile Val Trp Glu Ser Asp Pro Asn Arg
            580                 585                 590

Ser Tyr Thr Val Pro Ala Ala Cys Gly Val Ser Thr Ala Thr Glu Asn
```

Asp Thr Trp Arg
    610

<210> SEQ ID NO 14
<211> LENGTH: 1896
<212> TYPE: DNA
<213> ORGANISM: Aspergillus fumigatus
<220> FEATURE:
<221> NAME/KEY: misc_feature
<222> LOCATION: (1)..(1896)
<223> OTHER INFORMATION: AfGA2 gene of pTrex3gM-AfGA2

<400> SEQUENCE: 14

```
atgcctcgac tgagctacgc tctctgcgct ctgtccctgg gtcacgctgc catcgccgct      60
ccccaactga gcgcccgagc tactggcagc ctcgattcct ggctgggcac tgagaccacc     120
gttgctctga acggcatcct cgctaacatc ggcgctgatg gtgcctatgc aagagcgct      180 aaacctggca tcatcatcgc cagccctagc accagcgagc ctgattacta ctatacttgg     240
acccgcgacg ctgctctggt caccaaggtc ctcgttgacc tgttccgcaa tggtaacctg     300
ggcctccaga aagtcattac cgagtacgtc aacagccaag cttatctgca aaccgttagc     360
aatccctccg gtggcctcgc ttccggcggc ctggccgagc caaatacaaa cgtcgacatg     420
accgccttta ccggtgcctg gggtcgcccc cagcgagatg gccctgccct gcgcgccacc     480
gctctcatcg acttcggcaa ctggctgatc gacaacggct attccagcta tgctgtcaac     540
aacatttggc ccatcgtccg caacgacctg tcctatgttt cccaatactg gtcccagtcc     600
ggtttcgacc tctgggagga ggttaattcc atgagctttt tcaccgtcgc tgtccaacat     660
cgagctctcg tcgagggctc cactttcgct aagcgcgtcg cgccagctg ttcctggtgc     720 gattcccagg cccctcagat tctgtgctac atgcagtcct tttggaccgg tagctatatc     780
aatgccaata ccggcggtgg tcgaagcggc aaggacgcta atactgttct ggcttccatc     840
cacaccttcg atcccgaggc cggctgtgat gatactacct tcagccctg ctcccctcgc     900 gctctcgcca accataaagt ttacaccgac agctttcgca gcgtttacgc catcaactcc     960
ggcattcctc aaggcgctgc tgtttccgct ggtcgctacc ccgaggacgt ttactataat    1020 ggcaaccccct ggttcctcac tactctggct gctgctgagc agctctatga cgctatctac    1080
caatggaaga aaatcggcag catcagcatt acttccacct ccctcgcctt cttcaaagac    1140
atctatagct ccgctgccgt tggcacttat gcttcctcca ctagcacttt cactgatatt    1200
atcaacgctg ttaaaaccta cgctgacggc tacgtcagca tcgttcaagc ccacgctatg    1260
aacaacggtt ccctctccga gcagttcgac aagtccagcg tctgagcct cagcgctcgc    1320 gacctcacct ggtcctacgc cgccttcctg actgccaaca tgcgccgaaa cggcgtcgtt    1380 cctgccccctt ggggtgccgc cagcgccaat tccgtcccca gcagctgtag catgggctcc    1440
gccactggta cctacagcac cgctaccgct actagctggc cagcacccct gactagcggc    1500
tcccccggtt ccactactac cgtcggcacc actacctcca ccacttccgg tactgccacc    1560
gagactgcct gtgccacccc taccgccgtc gccgtcacct taacgagat tgctaccacc    1620 acctacggcg agaacgtcta catcgtcggt agcatctccg agctcggcaa ttgggacact    1680
tccaaggctg tcgccctgtc cgcctccaaa tatactagca gcaacaacct gtggtatgtc    1740
```

```
tccgttaccc tgcctgctgg tactactttt gagtacaagt acattcgcaa agagtccgat    1800
ggctccatcg tttgggagtc cgatcccaac cgaagctaca ccgttcccgc tgcttgtggc    1860
gtctccactg ctactgagaa tgacacctgg cgctaa                              1896
```